United States Patent [19]
Seilhamer et al.

[11] Patent Number: 5,840,484
[45] Date of Patent: Nov. 24, 1998

[54] COMPARATIVE GENE TRANSCRIPT ANALYSIS

[75] Inventors: Jeffrey J. Seilhamer, Los Altos Hills; Randal W. Scott, Mountain View, both of Calif.

[73] Assignee: Incyte Pharmaceuticals, Inc., Palo Alto, Calif.

[21] Appl. No.: 187,530

[22] Filed: Jan. 27, 1994

Related U.S. Application Data

[63] Continuation-in-part of Ser. No. 179,873, Jan. 11, 1994, and a continuation-in-part of Ser. No. 137,951, Oct. 14, 1993, and a continuation-in-part of Ser. No. 100,523, Aug. 3, 1993, which is a continuation-in-part of Ser. No. 977,780, Nov. 19, 1992, abandoned, which is a continuation-in-part of Ser. No. 916,491, Jul. 17, 1992, abandoned.

[51] Int. Cl.$^6$ .................................................... C12Q 1/68
[52] U.S. Cl. ................................................................ 435/6
[58] Field of Search ........................... 435/6; 364/413.02

[56] References Cited

U.S. PATENT DOCUMENTS

| | | | |
|---|---|---|---|
| 5,270,170 | 12/1993 | Schutz et al. | 435/7.37 |
| 5,364,759 | 11/1994 | Caskey et al. | 435/6 |
| 5,371,671 | 12/1994 | Anderson et al. | 364/413.01 |

FOREIGN PATENT DOCUMENTS

| | | |
|---|---|---|
| 91/19818 | 12/1991 | WIPO . |
| 93/06121 | 4/1993 | WIPO . |
| 93/22684 | 11/1993 | WIPO . |

OTHER PUBLICATIONS

Hara, Eiji et al. "Substractive cDNA cloning using oligo(dT)$_{30}$–latex and PCR: isolation of cDNA clones specific to undifferentiated human embryonal carcinoma cells". *Nucleic Acids Research*, vol. 19, No. 25.: 7097–7104 (1991).

Rubenstein, John L.R. et al. "Substractive hybridization system using single–stranded phagemids with directional inserts", *Nucleic Acids Research*, vol. 18, No. 16.: 4833–4842 (1990).

Rhyner, Thomas A. et al. "Molecular Cloning of Forebrain mRNAs which are Modulated by Sleep Deprivation", *European Journal of Neuroscience.* vol. 2: 1063–1073 (1990).

Fargnoil, Joseph et al. "Low–Ratio Hybridization Subtraction". *Analytical Biochemistry* 187: 364–372 (1990).

Schweinfest, Clfford W. et al. "Substraction Hybridization cDNA Libraries From Colon Carcinoma and Hepatic Cancer". *Genet Annal Tech Appl* 7: 64–70 (1990).

Travis, Gabriel H. et al. "Pheno emulsion–enhanced DNA–driven substractive cDNA cloning: Isolation of low–abundance monkey cortex–specific mRNAs". *Proceedings of the National Academy of Sciences, USA.* vol. 85: 1696–1700 (1988).

Batra, Surinder K. et al. "A Simple, Effective method for the Construction of Substracted cDNA Libraries". *GATA* 8(4):129–133 (1991).

Swaroop, Anand et al. "A simple and efficient cDNA library substraction procedure: isolation of human retina–specific cDNA clones". *Nucleic Acids Research* vol. 19, No.8: 1954 (1991).

Patanjali, Sankhavaram R. "Construction of a uniform–abundance (normalized) cDNA library". *Proceedings National Academy Sciences, USA,* vol. 88: 1943–1947 (1991).

Hoog, Christer. "Isolation of a large number of novel mamalian genes by a differential cDNA library screening strategy". *Nucleic Acids Research,* vol. 19, No.22: 6123–6127 (1991).

Duguid, John R. "Isolation of cDNA of scrapie–modulated RNAs by substractive hybridization of a cDNAs library". *Proceedings of the National Academy of Sciences, USA,* vol. 85:5738–2742. (1988).

Duguid, John R. et al. "Library substraction of in vitro cDNA libraries to indentify differentially expressed genes in scrapie infection". *Nucleic Acids Research,* vol. 18, No. 9: 2789–2792 (1989).

Sive, Hazel L. et al. "A simple substractive hybridization techique employing photoactivatable biotin and phenol extraction". *Necleic Acids Research,* vol. 16 No. 22: 10937 (1988).

IntelliGenetics Suite, Release 5.4, Advanced Training Manual, issued Jan. 1993 by IntelliGenetics, Inc. 700 East El Camino Real, Mountain View, California 94040, U.S.A. pp. (1–6)–(1–19) and (2–9)–(2–14).

Science, vol. 252, issued 21 Jun. 1991, M.D. Adams et al., "Complementary DNA sequencing: Expressed sequence tags and human genome project", pp. 1651–1656, see entire document.

Nature Genetics, vol. 2, No. 3, issued Nov. 1992, K. Okubo et al. "Large scale DNA sequencing for analysis for analysis of quantitative and qualitative aspects of gene expression", pp. 173–179, see narrative text portion of entire document.

(List continued on next page.)

*Primary Examiner*—James Martinell
*Attorney, Agent, or Firm*—Carol L. Francis; Bozicevic & Reed LLP

[57] ABSTRACT

A method and system for quantifying the relative abundance of gene transcripts in a biological sample. One embodiment of the method generates high-throughput sequence-specific analysis of multiple RNAs or their corresponding cDNAs (gene transcript imaging analysis). Another embodiment of the method produces a gene transcript imaging analysis by the use of high-throughput cDNA sequence analysis. In addition, the gene transcript imaging can be used to detect or diagnose a particular biological state, disease, or condition which is correlated to the relative abundance of gene transcripts in a given cell or population of cells. The invention provides a method for comparing the gene transcript image analysis from two or more different biological samples in order to distinguish between the two samples and identify one or more genes which are differentially expressed between the two samples.

11 Claims, 2 Drawing Sheets

OTHER PUBLICATIONS

Date, C.J., 1990, "An Introduction to Database Systems, "Fifth Edition, Addison–Wesley Publishing Company, Reading, MA, pp. 22–25, 42–45, and 111–117.

Davidson, D., (ed), "Introduction to Molecular Biology Information Servers," *SIGBIO Newsletter,* May 1991, vol. 11, No. 1 and 2, pp. 1–6.

Frenkel, K.A., Nov. 1991, "The Human Genome Project and Informatics: A Monumental Scientific Adventure," *Communications of the ACM,* 34(11) pp. 41–51.

Frickett, J.W., et al., "Development of a Database for Nucleotide Sequences," in: *Mathematical Methods for DNA Sequences,* M.S. Waterman (ed.), CRC Press, Florida, 1989 pp.1–15, 17–19, 21–31, and 34.

Khan, A.S., et al., 1992, "Single Pass Sequencing and Physical and Genetic Mapping of Human Brain cDNA," *Nature Genetics* 2:180–5.

Matsubara, K., et al., 1993, "Indentification of New Genes by Systemic Analysis of cDNA and Database Construction," *Current Biology Ldt.* 4 pp. 672–677.

COMPARATIVE GENE TRANSCRIPT ANALYSIS

CROSS-REFERENCE TO RELATED APPLICATIONS

This is a continuation-in-part application of co-pending U.S. patent application Ser. No. 08/179,873 filed Jan. 11, 1994, U.S. patent application Ser. No. 08/137,951 filed Oct. 14, 1993 and U.S. patent application Ser. No. 08/100,523 filed Aug. 3, 1993 which is a continuation-in-part application of U.S. patent application Ser. No. 07/977,780 filed Nov. 19, 1992 now abandoned, which is a continuation-in-part application of U.S. patent application Ser. No. 07/916,491 filed Jul. 17, 1992, now abandoned.

FIELD OF INVENTION

The present invention is in the field of molecular biology; more particularly, the present invention describes methods of high-throughput cDNA sequencing and transcript analysis.

BACKGROUND OF THE INVENTION

For the convenience of the reader, the references referred to in the text are listed numerically in parentheses. These numbers correspond to the numerical references listed in the appended bibliography. By these references, they are hereby expressly incorporated by reference herein.

Nucleic acids (DNA and RNA) carry within their structure the hereditary information and are therefore the prime molecules of life. Nucleic acids are found in all living organisms including bacteria, fungi, viruses, plants and animals. It is of interest to determine the relative abundance of nucleic acids in different cells, tissues and organisms over time under various conditions, treatments and regimes.

It is estimated that the 23 pairs of human chromosomes encode approximately 100,000 genes. All dividing cells in the body contain the same set of 23 pairs of chromosomes. The differences between different types of cells can be accounted for by the differential expression of the 100,000 or so genes found on the same 23 chromosomes. Many of the most fundamental questions of biology could be answered by a simple understanding of which genes are expressed and at what relative abundance in different cells.

Previously, the art has only provided for the analysis of a few known genes at a time by standard molecular biology techniques such as PCR, northern blot analysis, or other types of DNA probe analysis such as in situ hybridization. Each of these methods allows one to analyze the expression of only known genes or small numbers of genes at a time. (1–12)

Studies of the number and types of genes whose synthesis is induced or otherwise regulated during developmental processes such as cell activation, differentiation, aging, viral transformation, morphogenesis, and division have been pursued for many years, using a variety of methodologies. One of the earliest methods was to compare the proteins made in a given cell, tissue, organ system, or even organism both prior to and subsequent to the differentiation process of interest. Such comparisons were typically made using 2-dimensional gel electrophoresis, wherein each protein could be, in principle, identified and quantified as a discrete signal. In order to positively identify each signal, each discrete signal must be excised from the membrane and subjected to protein sequence analysis using Edman degradation. Unfortunately, most of the signals were present in quantities too small to obtain a reliable sequence, and many of those signals contained more than one discrete protein. An additional difficulty is that many of the proteins were blocked at the amino-terminus, further complicating the sequencing process.

Analyzing differentiation at the gene transcription level has overcome many of these disadvantages and drawbacks, since the power of recombinant DNA technology allows amplification of signals containing very small amounts of material. The most common method, called "hybridization subtraction", involves preparation of mRNA from the biological sample before (B) and after (A) the developmental process of interest, subtracting sample B from sample A by hybridization, and construction of a cDNA library from the non-hybridizing mRNA fraction of sample A. Many different groups have used this strategy successfully, and a variety of procedures have been published and improved upon using this same basic scheme (1–12).

All of these techniques have particular strengths and weaknesses, however there are still some limitations and undesirable aspects of these methods: First, the time and effort required to construct such libraries is quite large. Typically, a trained molecular biologist might expect construction and characterization of such a library to require 3 to 6 months, depending on his level of skill, experience, and luck. Second, the resulting subtraction libraries are typically inferior to the libraries constructed by standard methodology. A typical conventional cDNA library should have a clone complexity of at least $10^6$ clones, and an average insert size of 1–3 kB. In contrast, subtracted libraries can have complexities of $10^2$ or $10^3$ and average insert sizes of 0.2 kBp. Therefore, there can be a significant loss of clone and sequence information associated with such libraries. Third, this approach allows the researcher to capture only the genes induced in sample A relative to sample B; not vice-versa, nor does it easily allow comparison to a third sample of interest (C). Fourth, this approach requires very large amounts (hundreds of micrograms) of "driver" mRNA (sample A), which significantly limits the number and type of subtractions that are possible since many tissues and cells are very difficult to obtain in large quantities.

Fifth, the resolution of the subtraction is dependent upon the physical properties of DNA:DNA or RNA:DNA hybridization. The ability of a given sequence to find a hybridization match is dependent on its unique CoT value, which is in turn a function of the number of copies (concentration) of the particular sequence, multiplied by the time of hybridization. It follows that for sequences which are abundant, hybridization events will occur very rapidly (low CoT value), while rare sequences will form duplexes at very high CoT values. Unfortunately, the rare genes, or those present at abundances of $10^4$–$10^7$, tend to be the most interesting sequences, and those in which an investigator would likely be most interested. CoT values which allow such rare sequences to form duplexes are difficult to achieve in a convenient time frame, therefore hybridization subtraction is simply not a useful technique with which to study relative levels of rare mRNA species. Sixth, this problem is further complicated by the fact that duplex formation is also dependent on the nucleotide base composition for a given sequence. Those sequences rich in G+C form stronger duplexes than those with high contents of A+T, therefore the former sequences will tend to be removed selectively by hybridization subtraction. Seventh, it is possible that hybridization between nonexact matches can occur. When this happens, the expression of a homologous gene may "mask" expression of a gene of interest, artificially skewing the results for that particular gene.

The present invention has none of the drawbacks of the prior art. The present invention avoids these problems by providing a method to quantify the relative abundance of multiple gene transcripts in a given biological sample by the use of high-throughput sequence-specific analysis of individual RNA's or their corresponding cDNAs.

The present invention offers several advantages over current protein discovery methods which attempt to isolate individual proteins based upon biological effects. The method of the instant invention provides for detailed comparisons of cell profiles revealing numerous changes in the expression of individual transcripts.

The instant invention provides several advantages over previous subtraction methods including a more complete library analysis ($10^6$ to $10^7$ clones as compared to $10^3$ clones) which allows identification of low abundance messages as well as enabling the identification of messages which either decrease or decrease in abundance. These large libraries are very routine to make in contrast to the libraries of previous methods. In addition homologues can easily be distinguished with the method of the instant invention.

High resolution maps of gene expression can be used directly as a diagnostic profile or to identify disease-specific genes for the development of more classic diagnostic approaches.

This process is defined as gene transcript frequency analysis. The resulting quantitative analysis of the gene transcripts is defined as comparative gene transcript analysis.

SUMMARY OF THE INVENTION

The method is a method of analyzing a library of biological sequences comprising the steps of (a) producing a library of biological sequences; (b) generating a set of data values, where each of the data values in said set is indicative of a different one of the biological sequences of the library; (c) processing the data values in a programmed computer in which a data base of reference data values indicative of reference sequences is stored, to generate an identified sequence value for each of the data values, where each said identified sequence value is indicative of a degree of match between a different one of the biological sequences of the library and at least one of the reference sequences; and (d) processing each said identified sequence value to generate final data values indicative of the number of matches between the biological sequences of the library and ones of the reference sequences.

In a further embodiment, the method includes producing a gene transcript image analysis, by (a) isolating an mRNA population from a biological sample; (b) identifying genes from which the mRNA was transcribed by a sequence-specific method; (c) determining the numbers of mRNA transcripts corresponding to each of the genes; and (d) using the mRNA transcript numbers to determine the relative abundance of mRNA transcripts within the population of mRNA transcripts, where data determining the relative abundance values of mRNA transcripts is the gene transcript image analysis.

In a further embodiment, the relative abundance of the gene transcripts is determined by comparing the gene transcript numbers of genes in a single cell type or alternatively in different cell types.

In a further embodiment, the method includes a system for analyzing a library of biological sequences including a means for receiving a set of data values, where each of the data values is indicative of a different one of the biological sequences of the library; and a means for processing the data values in a computer system in which a data base of reference data values indicative of reference sequences is stored, wherein the computer is programmed with software for generating generate an identified sequence value for each of the data values, where each said identified sequence value is indicative of a degree of match between a different one of the biological sequences of the library and at least one of the reference sequences, and for processing each said identified sequence value to generate final data values indicative of number of matches between the biological sequences of the library and ones of the reference sequences.

In a further embodiment, a first value of the degree of match is indicative of an exact match, and a second value of said degree of match is indicative of a non-exact match.

In essence, the invention is a method and system for quantifying the relative abundance of gene transcripts in a biological sample. The invention provides a method for comparing the gene transcript image analysis from two or more different biological samples in order to distinguish between the two samples and identify one or more genes which are differentially expressed between the two samples. One embodiment of the method generates high-throughput sequence-specific analysis of multiple RNAs or their corresponding cDNAs: gene transcript imaging analysis. Another embodiment of the method produces the gene transcript imaging analysis by the use of high-throughput cDNA sequence analysis. In addition, the gene transcript imaging can be used to detect or diagnose a particular biological state, disease, or condition which is correlated to the relative abundance of gene transcripts in a given cell or population of cells.

In a class of embodiments, the invention is a method for producing a set ("library") of biological sequences. Biological sequences herein defined include: DNA, RNA, cDNA, proteins, amino acids, carbohydrates and the like. The method includes generating a set of data values, each of said data values indicative of a different one of the biological sequences of the library; processing the data values in a programmed computer, in which a data base of reference data values (indicative of reference sequences) is stored, to identify each sequence (i.e., generate an identified sequence value for each of the data values, where each identified sequence value is indicative of a degree of match between a different one of the biological sequences of the library and at least one of the reference sequences); and processing the identified sequence values to generate final data values (typically, a sorted list of identified sequences and corresponding abundance values) indicative of the number of matches between the sequences of the library and ones of the reference sequences.

Description of the Tables

Table 1 presents a detailed explanation of the letter codes utilized in Tables 2–5.

Table 2 is a list of isolates from the HUVEC cDNA library arranged according to abundance from U.S. patent application Ser. No. 08/137,951 filed Oct. 14, 1993 which is hereby incorporated by reference. The column labeled "number" refers to the sequence number in the Sequence Listing, i.e., the HUVEC sequence identification number. Isolates that have not been sequenced are not present in the Sequence Listing but are indicated in Table 2. The column labeled "1" refers to the library from which the cDNA clone was isolated: "H" for HUVEC cells. The column labeled "d" (an abbreviation for designation) contains a letter code indicating the general class of the sequence. The letter code, as presented in Table 1, is as follows: N-no homology to previously identified nucleotide sequences, E-exact match to a previously identified nucleotide sequence, U-the sequence of the isolate has not been determined, M-mitochondrial DNA sequence, O-homologous, but not identical to a previously identified nucleotide sequence, H-homologous, but not identical to a previously identified human gene, R-Repetitive DNA sequence, V-vector sequence, only, S-sequence not yet determined, I-matches an Incyte clone (part of an assemblage), X-matches an EST, and A-a poly A tract. The column labeled "f" refers to the distribution of the gene product encoded by the cDNA. The letter code as presented in Table 1 is as follows: C-non-specific, P-cell/tissue specific and U-unknown. The column labeled "z" refers to the cellular localization of the gene product encoded by the cDNA. The letter code is indicated in Table 1. The column labeled "r" refers to function of the gene product encoded by the cDNA. The letter code for the "r" column is presented in Table 1. The column labeled "c" refers to the certainty of the identification of the clone. The column labeled "entry" gives the NIH GENBANK locus name, identifying a nucleotide sequence homologous to the indicated sequence number. The column labeled "descriptor" provides a plain English explanation of the identity of the sequence corresponding to the NIH GENBANK locus name in the "entry" column. The "descriptor" column also indicates when unreadable sequence was present or when templates were skipped.

Table 3 is a comparison of the top 15 most abundant gene transcripts in normal and activated macrophage cells.

Table 4 is a list of the top 15 activated cDNAs activated macrophage cells compared to normal cells as determined by library subtraction.

Table 5 is a library subtraction analysis summary comparing THP-1 and HMC cDNA sequences.

DETAILED DESCRIPTION OF THE PREFERRED EMBODIMENTS

Figure 1:
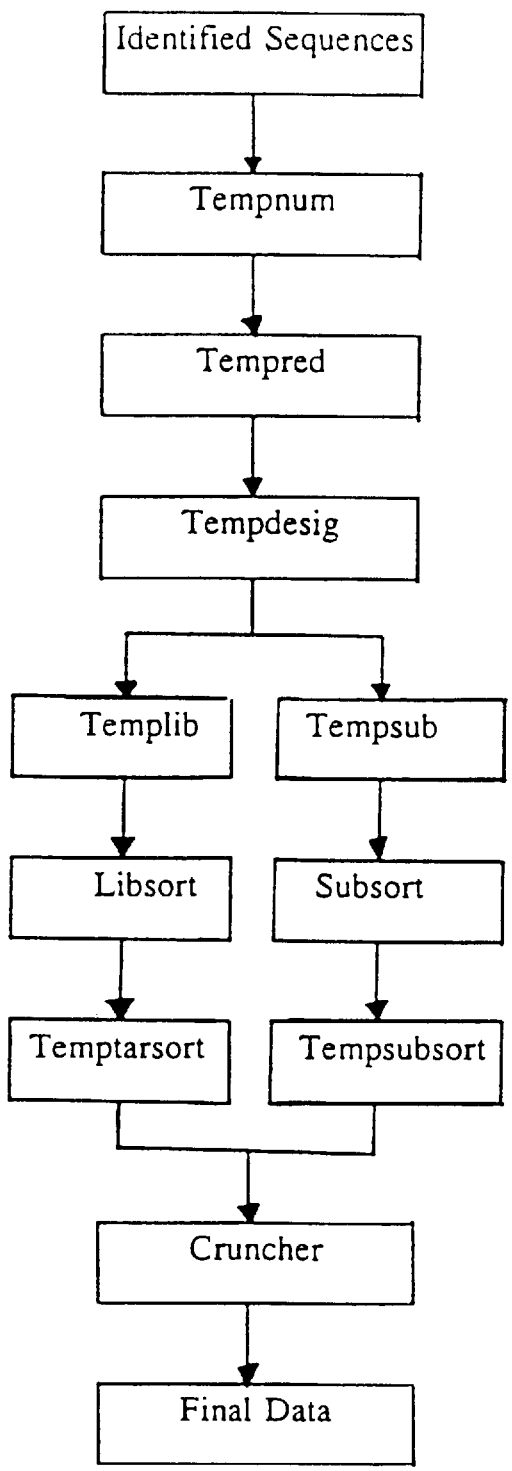
FIG. 1 is a diagram representing the sequence of operations performed by "abundance sort" software in a class of preferred embodiments of the inventive method.

The present invention provides a method to quantify the relative abundance of gene transcripts in a given biological sample by the use of high-throughput sequence-specific analysis of individual RNAs or their corresponding cDNAs (or alternatively, of data representing other biological sequences). This process is denoted herein as gene transcript imaging. The quantitative analysis of the relative abundance for a given gene transcript or set of gene transcripts is denoted herein as "gene transcript analysis" (or "gene transcript imaging analysis" or "gene transcript frequency analysis"). The present invention allows one to obtain a profile for gene transcription in any given population of cells or tissue from any type of organism. The invention can be applied to obtain a profile of a sample consisting of a single cell (or clones of a single cell), or of many cells, or of tissue more complex than a single cell.

For example gene transcript frequency analysis can be used to differentiate tumor cells from normal cells or activated macrophages from inactivated macrophages.

In an alternative embodiment, gene transcript frequency analysis is used to differentiate between cancer cells which respond to anti-cancer agents and those which do not respond. Potential anti-cancer agents include tamoxifen, vincristine, vinblastine, podophyllotoxins, etoposide, tenisposide, cisplatin, biologic response modifiers such as interferon, Il-2 GM-CSF, enzymes, hormones and the like.

In yet another embodiment, gene transcript frequency analysis is used to differentiate between liver cells isolated from patients treated and untreated with FIAU.

In yet another embodiment, gene transcript frequency analysis is used to differentiate between brain tissue from patients treated and untreated with lithium.

In a further embodiment, gene transcript frequency analysis is used to differentiate between cyclosporin and/or FK506 treated cells.

In a further embodiment, gene transcript frequency analysis is used to differentiate between viral infected, including HIV, human cells and uninfected human cells. Gene transcript frequency analysis is also used to compare HIV resistant cells to infected or HIV sensitive cells.

In a further embodiment, gene transcript frequency analysis is used to differentiate between bronchial lavage fluids from healthy and unhealthy patients.

In a further embodiment, gene transcript frequency analysis is used to differentiate between cell, plant, microbial and animal mutants and wild-type species. Such mutants could be deletion mutants which do not produce a gene product and/or point mutants which produce a less abundant message and could include mineral nutrition, metabolism, biochemical and pharmacological mutants isolated by means known to those skilled in the art.

In a further embodiment, gene transcript frequency analysis is used for an interspecies comparative analysis which would allow for the selection of better animal models. In this embodiment, human and animal (such as a mouse) cells are treated with a specific test agent. The relative sequence abundance of each cDNA population is determined. If the animal test system is a good model, the homologous genes should change expression similarly. If side effects are detected with the drug, a detailed transcript abundance analysis will be performed. Models will be selected by basic physiological changes.

In a further embodiment, gene transcript frequency analysis is used in a clinical setting to give a specific gene transcript profile of a patient from a patient sample (for example, where the patient sample is a blood sample). In particular, gene transcript frequency analysis is used to give a high resolution gene expression profile of a diseased state or condition.

In a further embodiment, gene transcript frequency analysis is used in a motif analysis to look for specific regions of proteins of interest. Such proteins include specific cell surface or membrane receptors, transcription factors and the like.

In essence, the method utilizes high-throughput cDNA sequencing to identify specific transcripts of interest. The generated cDNA and deduced amino acid sequences are then extensively compared with GENBANK and other sequence data banks as described below. The method offers several advantages over current protein discovery methods which try to isolate individual proteins based on biological effect. Here, detailed comparisons of activated and inactivated cell profiles reveal numerous changes in the expression of individual transcripts. After it is determined if the sequence is an exact match, a similar sequence or entirely dissimilar, the sequence is entered into a data base. Next, the numbers of copies of cDNA corresponding to a particular genes are tabulated. Although this can be done by human hand from a printout of all entries, a computer program is a useful way to tabulate this information The numbers of copies are divided by the total number of sequences in the data set, to obtain a relative abundance of transcripts for each corresponding gene. The list of represented genes can then be sorted by abundance in the cDNA population. A multitude of additional types of comparisons or dimensions are possible and described below in detail.

An alternate method of producing a gene transcript image includes the steps of obtaining a mixture of test mRNA and providing a representative array of unique probes whose sequences are complementary to at least some of the test mRNAs. Next, a fixed amount of the test mRNA is added to the arrayed probes. The test mRNA is incubated with the probes for a sufficient time to allow hybrids of the test mRNA and probes to form. The mRNA-probe hybrids are detected and the quantity determined. The hybrids are identified by their location in the probe array. The quantity of each hybrid is summed to give a population number. Each hybrid quantity is divided by the population number to provide a set of relative abundance data termed a gene transcript image analysis.

I CONSTRUCTION OF cDNA LIBRARIES

The human lymphoma U-937 cDNA library is commercially available from Stratagene (catalogue #937207. Stratagene, 11099 M. Torrey Pines Rd., La Jolla, Calif. 92037). The Stratagene library was prepared by Stratagene essentially as described. It was prepared by purifying poly (A+)RNA (mRNA) from U-937 cells and then enzymaticly synthesizing double stranded complementary DNA (cDNA) copies of the mRNA by priming with oligo dT. Synthetic adapter oligonucleotides were ligated onto the ends of the cDNA enabling its insertion into the lambda vector. The U-937 library was constructed using the Uni-ZAP™ vector system (Stratagene), allowing high efficiency unidirectional (sense orientation) lambda library construction and the convenience of a plasmid system with blue/white color selection to detect clones with cDNA insertions.

The human monocyte THP-1 cDNA library was custom constructed by Stratagene (Stratagene, 11099 M. Torrey Pines Rd., La Jolla, Calif. 92037). Poly(A+)RNA (mRNA) was purified from THP-1 cells (cultured 48 hr with 100 nm TPA and 4 hr with 1 μg/ml LPS). cDNA synthesis was primed separately with both oligo dT and random hexamers and the two cDNA copies were treated separately. Synthetic adapter oligonucleotides were ligated onto cDNA ends enabling its insertion into Uni-ZAP™ vector system (Stratagene), allowing high efficiency unidirectional (sense orientation) lambda library construction and the convenience of a plasmid system with blue/white color selection to detect clones with cDNA insertions. Finally, the two libraries were combined into a single library by mixing equal numbers of bacteriophage.

The human endothelial cell, HUVEC, cDNA library was custom constructed by Stratagene (Stratagene, 11099 M. Torrey Pines Rd., La Jolla, Calif. 92037). Poly(A+)RNA (mRNA) was purified separately from the two batches of induced HUVEC cells. cDNA synthesis was also separated into the two batches, primed separately with both oligo dT and random hexamers. Synthetic adaptor oligonucleotides were ligated onto cDNA ends enabling its insertion into Uni-ZAP™ vector system (Stratagene), allowing high efficiency unidirectional (sense orientation) lambda library construction and the convenience of a plasmid system with blue/white color selection to detect clones with cDNA insertions.

The human mast cell HMC-1 cDNA library was custom constructed by Stratagene (Stratagene, 11099 N. Torrey Pines Rd., La Jolla, Calif. 92037) using mRNA purified from cultured HMC-1 cells. The library was prepared by Stratagene essentially as described. The human mast cell (HMC-1) cDNA library was prepared by purifying poly(A+)RNA (mRNA) from human mast cells and then enzymaticly synthesizing double stranded complementary DNA (cDNA) copies of the mRNA. Synthetic adaptor oligonucleotides were ligated onto the ends of the cDNA enabling its insertion into the lambda vector. The HMC-1 library was constructed using the Uni-ZAP™ vector system (Stratagene), allowing high efficiency unidirectional (sense orientation) lambda library construction and the convenience of a plasmid system with blue/white color selection to detect clones with cDNA insertions.

The THP-1, U-937 cDNA, HUVEC and HMC-1 libraries can be screened with either DNA probes or antibody probes and the pBluescript® phagemid (Stratagene) can be rapidly excised in vivo. The phagemid allows the use of a plasmid system for: easy insert characterization, sequencing, site-directed mutagenesis, the creation of unidirectional deletions and expression of fusion proteins. The custom-constructed library phage particles-were infected into E. coli host strain XL1-Blue® (Stratagene), which has a high transformation efficiency, increasing the probability of obtaining rare, under-represented clones in the cDNA library.

Besides the Uni-ZAP™ vector system by Stratagene disclosed therein, it is now believed that other similarly unidirectional vectors also can be used. For example, it is believed that such vectors include but are not limited to DR2 (clontech), HXLOX (U.S. Biochemical)

For inter-library comparisons, the libraries must be prepared in similar manners. Certain parameters appear to be particularly important to control for. One such parameter is the method of isolating mRNA. It is important to remove DNA and heterogeneous nuclear RNA under the same conditions. Size fractionation of cDNA must be carefully controlled. The same vector preferably should be used for preparing libraries to be compared. At the very least, the same type of vector (e.g., unidirectional vector) should be used to assure a valid comparison. A unidirectional vector may be preferred because it is easier to analyze the output. However, with a unidirectional vector, there is dropout from the wrong direction ligations.

It is preferred to prime only with oligo dT unidirectional primer in order to obtain one only clone per mRNA transcript when obtaining transcript. However, it is recognized that employing a mixture of dT and random primers can also be advantageous because such a mixture affords more freedom when gene discovery also is a goal. Experiments have indicated that no obvious bias is introduced when random primers are employed. Similar effects can be obtained with DR2 from Clontech, HXLOX (US Biochemical) and also from Invitrogen and Novagen. These vectors have two requirements. First, there must be primer sites for commercially available primers such as T3 or M13 reverse primers. Second, the vector must accept inserts up to 10 kb.

It also is important to sample randomly a significant population of clones. Data has been generated with 5,000 clones; however, if very rare genes are to be obtained and/or their relative abundance determined, as many as 100,000 clones may need to be sampled. Size fractionation of cDNA must be carefully controlled.

The examples below are provided to illustrate the subject invention. These examples are provided by way of illustration and are not included for the purpose of limiting the invention.

II ISOLATION OF cDNA CLONES

The phagemid forms of individual cDNA clones were obtained by the in vivo excision process, in which the host bacterial strain was coinfected with both the lambda library phage and an f1 helper phage. Proteins derived from both the library-containing phage and the helper phage nicked the lambda DNA, initiated new DNA synthesis from defined sequences on the lambda target DNA and created a smaller, single stranded circular phagemid DNA molecule that included all DNA sequences of the pBluescript® plasmid and the cDNA insert. The phagemid DNA was secreted from the cells and purified, then used to re-infect fresh host cells, where the double stranded phagemid DNA was produced. Because the phagemid carries the gene for B-lactamase, the newly-transformed bacteria are selected on medium containing ampicillin.

Phagemid DNA was purified using the Magic Minipreps™ DNA Purification System (Promega catalogue #A7100. Promega Corp., 2800 Woods Hollow Rd., Madison, Wis. 53711). This small-scale process provides a simple and reliable method for lysing the bacterial cells and rapidly isolating purified phagemid DNA using a proprietary DNA-binding resin. The DNA was eluted from the purification resin already prepared for DNA sequencing and other analytical manipulations.

Phagemid DNA was also purified using the QIAwell-8 Plasmid Purification System from QIAGEN® DNA Purification System (QIAGEN Inc., 9259 Eton Ave., Chattsworth, Calif. 91311). This product line provides a convenient, rapid and reliable high-throughput method for lysing the bacterial cells and isolating highly purified phagemid DNA using QIAGEN anion-exchange resin particles with EMPORE™ membrane technology from 3M in a multiwell format. The DNA was eluted from the purification resin already prepared for DNA sequencing and other analytical manipulations.

III SEQUENCING OF cDNA CLONES

The cDNA inserts from random isolates of the U-937 and THP-1 libraries were sequenced in part. Methods for DNA sequencing are well known in the art. Conventional enzymatic methods employ DNA polymerase Klenow fragment, Sequenase™ or Taq polymerase to extend DNA chains from an oligonucleotide primer annealed to the DNA template of interest. Methods have been developed for the use of both single- and double stranded templates. The chain termination reaction products are usually electrophoresed on urea-acrylamide gels and are detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (such as the Applied Biosystems 373 DNA sequencer and Catalyst 800). Currently constructing 5000 clone libraries and randomly selecting about 2,000–2,500 clones with 30–50% usable, V HOMOLOGY SEARCHING OF cDNA CLONE AND DEDUCED PROTEIN (and Subsequent Steps)

Using the nucleotide sequences derived from the cDNA clones as query sequences (sequences of a Sequence Listing), databases containing previously identified sequences are searched for areas of homology (similarity). Examples of such databases include Genbank and EMBL. We next describe examples of two homology search algorithms that can be used, and then describe the subsequent computer-implemented steps to be performed in accordance with preferred embodiments of the invention.

In the following description of the computer-implemented steps of the invention, the word "library" denotes a set (or population) of biological sample sequences. A "library" can consist of cDNA sequences, RNA sequences, protein sequences, or the like, which characterize a biological sample. The biological sample can consist of cells of a single human cell type (or can be any of the other above-mentioned types of samples). We contemplate that the sequences in a library have been determined so as to accurately represent or characterize a biological sample (for example, they can consist of representative cDNA sequences from clones of a single human cell).

In the following description of the computer-implemented steps of the invention, the expression "data base" denotes a set of stored data which represent a collection of sequences, which in turn represent a collection of biological reference materials. For example, a data base can consist of data representing many stored cDNA sequences which are in turn representative of human cells infected with various viruses, human cells of various ages, cells from various species of mammals, and so on. For another example, a data base can consist of data representing many stored protein sequences which are representative of human cells infected with various viruses, human cells of various ages, cells from various species of mammals, and so on.

In preferred embodiments, the invention employs a computer programmed with software (to be described) for performing the following steps:

(a) processing data indicative of a library of cDNA sequences (generated as a result of high-throughput cDNA sequencing) to determine whether each sequence in the library matches a cDNA sequence of a data base of cDNA sequences (and if so, identifying the data base entry which matches the sequence);

(b) for some or all entries of the data base, tabulating the number of sequences of the library which match each such entry (although this can be done by human hand from a printout of all entries, we prefer to perform this step using computer software to be described below), thereby generating a set of "abundance numbers"; and (c) dividing each abundance number by the total number of sequences in the library, to obtain a relative abundance number for each data base entry.

The list of represented data base entries (or genes corresponding thereto) can then be sorted by abundance in the cDNA population. A multitude of additional types of comparisons or dimensions are possible.

For example (to be described below in greater detail), steps (a) and (b) can be repeated for two different libraries (sometimes referred to as a "target" library and a "subtractant" library). Then, for each data base entry, a "ratio" value is generated by dividing the abundance number (for that entry) for the target library, by the abundance number (for that entry) for the subtractant library. Each ratio value can then be divided by the total number of sequences in one or both libraries, to obtain a relative ratio value for each data base entry.

In variations on step (a), the library consists of nucleotide sequences derived from cDNA clones. Examples of data bases which can be searched for areas of homology (similarity) in step (a) include the commercially available data bases known as Genbank and EMBL.

One homology search algorithm which could be used to implement step (a) is the algorithm described in the paper by D. J. Lipman and W. R. Pearson, entitled "Rapid and Sensitive Protein Similarity Searches", *Science,* 227, 1435 (1985). In this algorithm, the homologous regions are searched in a two step manner. In the first step, the highest homologous regions are determined by calculating a matching score using a homology score table. The parameter "Ktup" is used in this step to establish the minimum window size to be shifted for comparing two sequences. Ktup also sets the number of bases that must match to extract the highest homologous region among the sequences. In this step, no insertions or deletions are applied and the homology is displayed as an initial (INIT) value.

In the second step, the homologous regions are aligned to obtain the highest matching score by inserting a gap in order to add a probable deleted portion. The matching score obtained in the first step is recalculated using the homology score Table and the insertion score Table to an optimized (OPT) value in the final output.

DNA homologies between two sequences can be examined graphically using the Harr method of constructing dot matrix homology plots (Needleman, S. B. and Wunsch, C. O., J. Mol. Biol 48:443 (1970)). This method produces a two-dimensional plot which can be useful in determining regions of homology versus regions of repetition.

However, in a class of preferred embodiments, step (a) is implemented by processing the library data in the commercially available computer program known as the Inherit 670 Sequence Analysis System, available from Applied Biosystems Inc. (of Foster City, Calif.), including the software known as the Factura software (also available from Applied Biosystems Inc.). The Factura program preprocesses each library sequence to "edit out" portions thereof which are not likely to be of interest.

In the algorithm implemented by the Inherit 670 Sequence Analysis System, the Pattern Specification Language (developed by TRW Inc.) is used to determine regions of homology. There are three parameters that determine how the sequence comparisons are run: window size, window offset, and error tolerance. Using a combination of these three parameters, a data base (such as a DNA data base) can be searched for sequences containing regions of homology and the appropriate sequences are scored with an initial value. Subsequently, these homologous regions are examined using dot matrix homology plots to determine regions of homology versus regions of repetition. Smith-Waterman alignments can be used to display the results of the homology search.

The Inherit software can be executed by a Sun computer system programmed with the UNIX operating system.

In preferred embodiments, the processed data generated by the Inherit software (representing identified sequences) are input into, and further processed by, a Macintosh personal computer (available from Apple) programmed with an "abundance sort and subtraction analysis" computer program (to be described below).

The abundance sort and subtraction analysis program (also denoted as the "abundance sort" program) classifies identified sequences from the cDNA clones as to whether they are exact matches (regions of exact homology), homologous human matches (regions of high similarity, but not exact matches), homologous non-human matches (regions of high similarity present in species other than human), or non matches (no significant regions of homology to previously identified nucleotide sequences stored in the form of the data base).

With reference again to the step of identifying matches between library sequences and data base entries, in cases where the library consists of deduced protein and peptide sequences, the match identification can be performed in a manner analogous to that done with cDNA sequences. A protein sequence is used as a query sequence and compared to the previously identified sequences contained in a data base such as the Swiss/Prot data base or the NBRF Protein database to find homologous proteins. These proteins are initially scored for homology using a homology score Table (Orcutt, B. C. and Dayoff, M. O. Scoring Matrices, PIR Report MAT-0285 (February 1985)) resulting in an INIT score. The homologous regions are aligned to obtain the highest matching scores by inserting a gap which adds a probable deleted portion. The matching score is recalculated using the homology score Table and the insertion score Table resulting in an optimized (OPT) score. Even in the absence of knowledge of the proper reading frame of an isolated sequence, the above-described protein homology search may be performed by searching all 3 reading frames.

Peptide and protein sequence homologies can also be ascertained using the Inherit 670 Sequence Analysis System in an analogous way to that used in DNA sequence homologies. Pattern Specification Language and parameter windows are used to search protein databases for sequences containing regions of homology which are scored with an initial value. Subsequent examination with a dot-matrix homology plot determines regions of homology versus regions of repetition.

The ABI Assembler application software, part of the INHERITS DNA analysis system (available from Applied Biosystems, Inc., Foster City, Calif.), can be employed to create and manage sequence assembly projects by assembling data from selected sequence fragments into a larger sequence. The Assembler software combines two advanced computer technologies which maximize the ability to assemble sequenced DNA fragments into Assemblages, a special grouping of data where the relationships between sequences are shown by graphic overlap, alignment and statistical views. The process is based on the Meyers-Kececioglu model of fragment assembly (INHERITS™ Assembler User's Manual, Applied Biosystems, Inc., Foster City, Calif.), and uses graph theory as the foundation of a very rigorous multiple sequence alignment engine for assembling DNA sequence fragments.

Next, with reference to FIG. 1, we describe in more detail the "abundance sort" program which implements above-mentioned "step (b)" to tabulate the number of sequences of the library which match each data base entry (the "abundance number" for each data base entry).

FIG. 1 is a flow chart of a preferred embodiment of the abundance sort program. A source code listing of this embodiment of the abundance sort program is set forth below as Appendix A. In the Appendix A implementation, the abundance sort program is written using the FoxBASE programming language commercially available from Microsoft Corporation. The subroutine names specified in FIG. 1 correspond to subroutines listed in Appendix A.

With reference again to FIG. 1, the "Identified Sequences" are data values representing each sequence of the library and a corresponding identification of the data base entry (if any) which it matches. In other words, the "Identified Sequences" are data values representing the output of above-discussed "step (a)."

Figure 2:
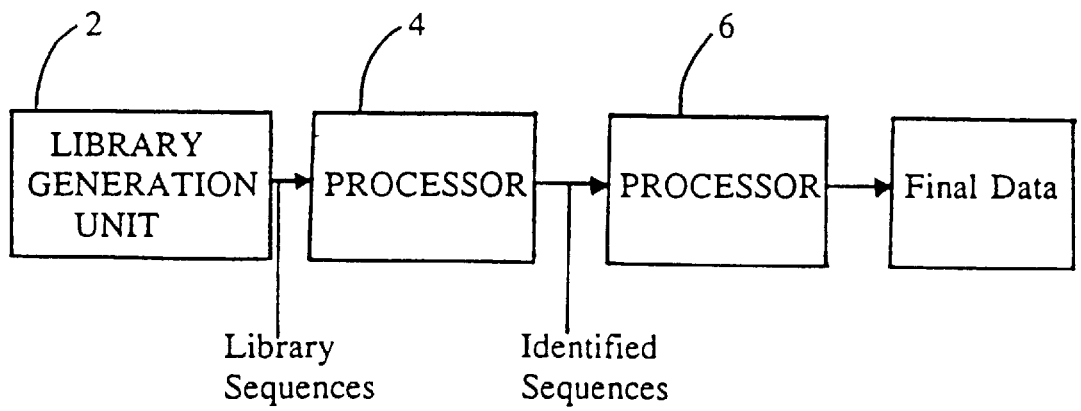
FIG. 2 is a block diagram of a preferred embodiment of the system of the invention.

FIG. 2 is a block diagram of a system for implementing the invention. The FIG. 2 system includes library generation unit 2 which generates a library and asserts an output stream of data values indicative of the sequences comprising the library. Programmed processor 4 receives the data stream output from unit 2, and processes this data in accordance with above-discussed "step (a)" to generate the Identified Sequences. Processor 4 can be a processor programmed with the commercially available computer program known as the Inherit 670 Sequence Analysis System and the commercially available computer program known as the Factura program (both available from Applied Biosystems Inc.) and with the UNIX operating system.

Still with reference to FIG. 2, the Identified Sequences are loaded into processor 6 which is programmed with the abundance sort program. Processor 6 generates the Final Data values indicated in both FIGS. 1 and 2.

With reference to FIG. 1, the abundance sort program first performs an operation known as "Tempnum" on the Identified Sequences, to discard all of the Identified Sequences except those which match data base entries of selected types. For example, the Tempnum process can select Identified Sequences which represent matches of the following types with data base entries: "exact" matches (exact matches with data base entries representing human genes); "homologous" matches (approximate, but not exact, matches with data base entries representing human genes), "other species" matches (exact and/or approximate matches with data base entries representing genes present in species other than human), or "no" matches (no significant regions of homology with data base entries representing previously identified nucleotide sequences).

The data values selected during the "Tempnum" process then undergo a further selection (weeding out) operation known as "Tempred." This operation can, for example, discard all data values representing matches with selected data base entries.

The data values selected during the "Tempred" process are then classified according to library, during the "Tempdesig" operation. It is contemplated that the Identified Sequences can represent sequences from a single library, or from two or more libraries.

Consider first the case that they represent sequences from a single library. In this case, all the data values determined during "Tempred" undergo sorting in the "Templib" operation, further sorting in the "Libsort" operation, and finally additional sorting in the "Temptarsort" operation. For example, these three sorting operations can sort the identified sequences in order of decreasing "abundance number" (to generate a list of decreasing abundance numbers, each abundance number corresponding to a data base entry, or several lists of decreasing abundance numbers, with the abundance numbers in each list corresponding to data base entries of a selected type) with redundancies eliminated from each sorted list. In this case, the operation identified as "Cruncher" can be bypassed, so that the "Final Data" values are the organized data values produced during the "Temptarsort" operation.

We next consider the case that the data values produced during the "Tempred" operation represent sequences from two libraries (which we will denote the "target" library and the "subtractant" library). For example, the target library may consist of cDNA sequences from clones of a diseased cell, while the subtractant library may consist of cDNA sequences from clones of the diseased cell after treatment by exposure to a drug. For another example, the target library may consist of cDNA sequences from clones of a cell from a young human, while the subtractant library may consist of cDNA sequences from clones of a cell from the same human (after he or she has aged).

In this case, the "Tempdesig" operation routes all data values representing the target library for processing in accordance with "Templib" (and then "Libsort" and "Temptarsort"), and routes all data values representing the subtractant library for processing in accordance with "Tempsub" (and then "Subsort" and "Tempsubsort"). For example, the consecutive "Templib," "Libsort," and "Temptarsort" sorting operations can sort identified sequences from the target library in order of decreasing abundance number (to generate a list of decreasing abundance numbers, each abundance number corresponding to a data base entry, or several lists of decreasing abundance numbers, with the abundance numbers in each list corresponding to data base entries of a selected type) with redundancies eliminated from each sorted list. The consecutive "Tempsub," "Subsort," and "Tempsubsort" sorting operations would sort identified sequences from the subtractant library in order of decreasing abundance number (to generate a list of decreasing abundance numbers, each abundance number corresponding to a data base entry, or several lists of decreasing abundance numbers, with the abundance numbers in each list corresponding to data base entries of a selected type) with redundancies eliminated from each sorted list. The data values output from the "Temptarsort" operation typically represent sorted lists from which a histogram could be generated in which position along one (e.g., horizontal) axis indicates abundance number (of target library sequences), and position along another (e.g., vertical) axis indicates data base entry (e.g., human or non-human gene type). Similarly, the data values output from the "Tempsubsort" operation typically represent sorted lists from which a histogram could be generated in which position along one (e.g., horizontal) axis indicates abundance number (of subtractant library sequences), and position along another (e.g., vertical) axis indicates data base entry (e.g., human or non-human gene type).

The data values (sorted lists) output from the Tempsubsort and Temptarsort sorting operations are combined during the operation identified as "Cruncher." The "Cruncher" process identifies pairs of corresponding target and subtractant abundance numbers (both representing the same data base entry), and divides one by the other to generate a "ratio" value for each pair of corresponding abundance numbers, and then sorts the ratio values in order of decreasing ratio value. The data values output from the "Cruncher" operation (the Final Data values in FIG. 1) typically determine a sorted list from which a histogram could be generated in which position along one axis indicates a ratio of abundance numbers (for corresponding sequences from target and subtractant libraries), and position along another axis indicates data base entry (e.g., gene type).

Preferably, the Cruncher operation also divides each ratio value by the total number of sequences in one or both of the target and subtractant libraries. The resulting lists of "relative" ratio values generated by the Cruncher operation would be useful for many medical, scientific, and industrial applications. Also preferably, the output of the Cruncher operation is a set of lists, each list representing a decreasing sequence of ratio values for a different selected subset of data base entries.

In one example, the abundance sort program of the invention tabulates the numbers of mRNA transcripts corresponding to each gene identified in a data base. These numbers are divided by the total number of clones sampled. The results of the division reflect the relative abundance of the mRNA transcripts in the cell type or tissue from which they were obtained. Obtaining this final data set is referred to herein as "gene transcript image analysis."

The resulting relative abundance data shows exactly what proteins are upregulated and downregulated. Table 5 shows a comparison of the most common mRNA transcripts between the cell types. Gene transcript image analysis can be done for different cell types and for the same cell type at different stages of development or activation (for example, to compare common mRNA transcripts in one cell type. (See Tables 3–5). Also, such abundance data can be obtained on a patient sample and used to diagnose conditions associated with macrophage activation.

A gene transcript imaging analysis (or multiple gene transcript imaging analyses) can be used in toxicological studies. For example, the differences in gene transcript imaging analyses before and after treatment can be assessed for patients on placebo and drug treatment. This method effectively screens for markers to follow in clinical use of the drug. Often clinicians have difficulty ascertaining the difference between pathology caused by the disease being treated and by the drug being administered. A gene transcript imaging analysis before treatment can be compared with a gene transcript imaging analysis after treatment to isolate new, unwanted pathology caused by the drug. Such a detailed analysis of patients having hepatitis can help distinguish new hepatic injury caused by drug treatment.

More detailed comparisons can be easily prepared. Actual relative abundances for different samples can be reported in separate columns, or one group of numbers can be divided by the other group to highlight the most extreme changes in relative abundance. Such computations can be performed by humans but are more efficiently performed by computer.

Additional types of comparisons can be made. Cells from different species can be compared by comparative gene transcript analysis to screen for specific differences. Such testing aids in the selection and validation of an animal model for the commercial purpose of drug screening or toxicological testing of drugs intended for human or animal use. When the comparison between animals of different species is shown in columns for each species, we refer to this as a interspecies comparison.

This invention employs data bases of co-pending U.S. patent application Ser. No. 08/179,873 filed Jan. 11, 1994, U.S. patent application Ser. No. 08/137,951 filed Oct. 14, 1993 and U.S. patent application Ser. No. 08/100,523 filed Aug. 3, 1993 which is a continuation-in-part application of co-pending U.S. patent application Ser. No. 07/977,780 filed Nov. 19, 1992 which is a continuation-in-part application of co-pending U.S. patent application Ser. No. 07/916,491 filed Jul. 17, 1992. These five patent applications (whose text is incorporated herein by reference) include teaching which may be applied in implementing such other embodiments of the present invention.

Other embodiments of the invention employ other data bases, such as a random peptide data base, a polymer data base, a synthetic oligomer data base, or a oligonucleotide data base of the type described in U.S. Pat. No. 5,270,170, issued Dec. 14, 1993 to Cull, et al., PCT International Application Publication No. WO 9322684, published Nov. 11, 1993, PCT International Application Publication No. WO 9306121, published Apr. 1, 1993, or PCT International Application Publication No. WO 9119818, published Dec. 26, 1991. These four references (whose text is incorporated herein by reference) include teaching which may be applied in implementing such other embodiments of the present invention.

REFERENCES

1. Nucleic Acids Research 19:7097–7104 (1991)
2. Nucleic Acids Research 18:4833–4842 (1990)
3. Nucleic Acids Research 18:2789–2792 (1989)
4. European Journal of Neuroscience 2:1063–1073 (1990)
5. Analytical Biochemistry 187:364–373 (1990)
6. Genet Annal Techn Appl 7:64–70 (1990)
7. GATA 8(4): 129–133 (1991)
8. Proc. Natl. Acad. Sci. USA 85:1696–1700 (1988)
9. Nucleic Acids Research 19:1954 (1991)
10. Proc. Natl. Acad. Sci. USA 88:1943–1947 (1991)
11. Nucleic Acids Research 19:6123–6127 (1991)
12. Proc. Natl. Acad. Sci. USA 85:5738–5742 (1988)
13. Nucleic Acids Research 16:10937 (1988)

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments.

APPENDIX A

```
* Master menu for SUBTRACTION output
SET TALK OFF
SET SAFETY OFF
SET EXACT ON
SET TYPEAHEAD TO 0
CLEAR ALL
CLEAR
SET DEVICE TO SCREEN
USE "SmartGuy:FoxBASE+/Mac: fox files:Clones.dbf"
GO TOP
STORE NUMBER TO INITIATE
GO BOTTOM
STORE NUMBER TO TERMINATE
STORE 0 TO UON
STORE 0 TO MON
STORE 0 TO TON
STORE 0 TO HON
STORE 0 TO AON
STORE 0 TO SON
STORE 0 TO PON
STORE 0 TO CON
STORE 0 TO ION
STORE 0 TO YGN
STORE 0 TO LON
STORE 0 TO FON
```

APPENDIX A-continued

```
STORE 0 TO USUB
STORE 0 TO MSUB
STORE 0 TO TSUB
STORE 0 TO HSUB
STORE 0 TO ASUB
STORE 0 TO SSUB
STORE 0 TO PSUB
STORE 0 TO CSUB
STORE 0 TO ISUB
STORE 0 TO YSUB
STORE 0 TO LSUB
STORE 0 TO FSUB
STORE 0 TD ANAL
STORE 0 TO EMATCH
STORE 0 TO HMATCH
STORE 0 TO OMATCH
STORE 0 TO IMATCH
STORE 0 TO PTF
Do WHILE .T.
* Program.: Subtraction.frnt
* Date ...: 1/13/94
* Version.: FoxBASE+/Mac, revision 1.10
* Notes......:Format file Subtraction
*
SCREEN 1 TYPE 0 HEADING "Screen 1" AT 40,2 SIZE 286,492 PIXELS FONT "Geneva",9 COLOR 0,0,0,
@PIXELS 75,120 TO 178,241 STYLE 799 COLOR 0,0,0,0,0,0
@PIXELS 27,134 SAY "Subtraction Menu"STYLE 65536 FONT "Geneva",274 COLOR 0,0,0,-1,-1,-1
@PIXELS 117,126 GET EMATCH STYLE 65536 FONT "Chicago",12 PICTURE "@*C Exact" SIZE 15,62 CO
@PIXELS 135,126 GET HMATCH STYLE 65536 FONT "Chicago",12 PICTURE "@*C Homologous" SIZE 15,1
@PIXELS 153,126 GET OMATCH STYLE 65536 FONT "Chicago",12 PICTURE "@*C Other spc" SIZE 15,84
@PIXELS 90,152 SAY "Matches:"STYLE 65536 FONT "Geneva",12 COLOR 0,0,0,-1,-1,-1
@PIXELS 171,126 GET Imatch STYLE 65536 FONT "Chicago",12 ;PICTURE "@*C Incyte" SIZE 15,65 CO
@PIXELS 252,146 GET initiate STYLE 0 FONT "Geneva",12 SIZE* 15,70 COLOR 0,0,0,-1,-1,-1
@PIXELS 270,146 GET terminate STYLE 0 FONT "Geneva",12 SIZE 15,70 COLOR 0,0,0,-1,-1,-1
@PIXELS 234,134 SAY "Include clones" STYLE 65536 FONT "Geneva",12 COLOR 0,0,0,-1,-1,-1
@PIXELS 270,125 SAY "->" STYLE 65536 FONT "Geneva",14 COLOR 0,0,0,-1,-1,-1
@PIXELS 198,126 GET PTF STYLE 65536 FONT "Chicago",12 PICTURE "@*C Print to file" SIZE 15,9
@PIXELS 72,9 TO 277,115 STYLE 799 COLOR 0,0,0,0,0,0
@PIXELS 90,18 GET UON STYLE 65536 FONT "Chicago",10 PICTURE "@*C U937" SIZE 13,49 COLOR 0,0
@PIXELS 99,18 GET MON STYLE 65536 FONT "Chicago",10 PICTURE "@*C HMC" SIZE 13,45 COLOR 0,0,
@PIXELS 108,18 GET TON STYLE 65536 FONT "Chicago",10 PICTURE "@'C THP-1" SIZE 13,54 COLOR 0
@PIXELS 117,18 GET HON STYLE 65536 FONT "Chicago",10 PICTURE "@*C HUVEC" SIZE 13,55 COLOR 0
@PIXELS 126,18 GET AON STYLE 65536 FONT "Chicago",10 PICTURE "@#C Adenoid" SIZE 13,67 COLOR
@PIXELS 135,18 GET SON STYLE 65536 FONT "Chicago",10 PICTURE "@#C Spleen" SIZE 13,59 COLOR
@PIXELS 144,18 GET PON STYLE 65536 FONT "Chicago",10 PICTURE "@*C Con THP" SIZE 13,65 COLOR
@PIXELS 153,18 GET CON STYLE 65536 FONT "Chicago",10 PICTURE "@*C Con HUVEC" SIZE 13,79 COLOR
@PIXELS 162,18 GET YON STYLE 65536 FONT "Chicago",10 PICTURE "@*C T + B cell" SIZE 13,70 COLOR
@PIXELS 171,18 GET ION STYLE 65536 FONT "Chicago",10 PICTURE "@*C Cornea" SIZE 13,61 COLOR
@PIXELS 180,18 GET LON STYLE 65536 FONT "Chicago",10 PICTURE "@*C. Liver" SIZE 13,50 COLOR 0
@PIXELS 189,18 GET FON STYLE 65536 FONT "Chicago",10 PICTURE "@*C Fibroblast" SIZE 13,80 COLOR
@PIXELS 72,288 TO 277,394 STYLE 799 COLOR 0,0,0,0,0,0
@PIXELS 90,297 GET USUB STYLE 65536 FONT "Chicago",10 PICTURE "@*C U937" SIZE 13,49 COLOR 0
@PIXELS 99,297 GET MSUB STYLE 65536 FONT "Chicago",10 PICTURE "@*C HMC" SIZE 13,45 COLOR 0,
@PIXELS 108,297 GET TSUB STYLE 65536 FONT "Chicago",10 PICTURE "@*C THP-1" SIZE 13,54 COLOR
@PIXELS 117,297 GET HSUB STYLE 65536 FONT "Chicago",10 PICTURE "@*C HUVEC" SIZE 13,55 COLOR
@PIXELS 126,297 GET ASUB STYLE 65536 FONT "Chicago",10 PICTURE "@*C Adenoid" SIZE 13,67 COLOR
@PIXELS 135,297 GET SSUB STYLE 65536 FONT "Chicago",10 PICTURE "@*C Spleen" SIZE 13,59 COLOR
@PIXELS 144,297 GET PSUB STYLE 65536 FONT "Chicago",10 PICTURE "@*C Con THP" SIZE 13,65 COLOR
@PIXELS 153,297 GET CSUB STYLE 65536 FONT "Chicago",10 PICTURE "@*C Con HUVEC" SIZE 13,79 COLOR
@PIXELS 162,297 GET YSUB STYLE 65536 FONT "Chicago",10 PICTURE "@*C T + B cell" SIZE 13,70
@PIXELS 171,297 GET ISUB STYLE 65536 FONT "Chicago",10 PICTURE "@*C Cornea" SIZE 13,61 COLOR
@PIXELS 180,297 GET LSUB STYLE 65536 FONT "Chicago",10 PICTURE "@*C Liver" SIZE 13,50 COLOR
@PIXELS 189,297 GET FSUB STYLE 65536 FONT "Chicago",10 PICTURE "@*C Fibroblast" SIZE 13,80
@PIXELS 63,314 SAY "Subtract:" STYLE 65536 FONT "Geneva",14 COLOR 0,0,0,-1,-1,-1
@PIXELS 54,72 GET ANAL STYLE 65536 FONT "Chicago",12 PICTURE "@*R Overall;Function"SIZE 41
*
* EOF: Subtraction.fmt
READ
IF TERMINATE=0
CLEAR
CLOSE DATABASES
USE "SmartGuy:FoxBASE+/Mac: fox files:clones.dbf"
SET SAFETY ON
SCREEN 1 OFF
RETURN
ENDIF
STORE VAL(SYS(2)) TO STARTIME
clear
SET TALK ON
```

APPENDIX A-continued

```
GAP = TERMINATE-INITIATE+1
GO INITIATE
COPY NEXT GAP FIELDS NUMBER,L,D,F,Z,R,ENTRY,S,DESCRIPTOR,START,RFEND, 1 TO TEMPNUM
USE TEMPNUM
COUNT TO TOT
COPY TO TEMPRED FOR D='E'.OR.D='O'.OR.D='H'.OR.D='N'.OR.D='I'
USE TEMPRED
IF Ematch=0 .AND. Hmatch=0.AND. Omatch=0 .AND. IMATCH=0
COPY TO TEMPDESIG
ELSE
COPY STRUCTURE TO TEMPDESIG
USE TEMPDESIG
IF Ematch=1
APPEND FROM TEMFNUM FOR D='E'
ENDIF
IF Hmatch=1
APPEND FROM TEMPNUM FOR D='H'
ENDIF
IF Omatch=1
APPEND FROM TEMPNUM FOR D='O'
ENDIF
IF Imatch=1
APPEND FROM TEMPNUM FOR D='I'.OR.D='X'
*.OR.D='N'
ENDIF
ENDIF
COUNT TO STARTOT
COPY STRUCTURE TO TEMPLIB
USE TEMPLIB
IF UON=0 .AND. MON=0 .AND. TON=0 .AND. AON=0 .AND. SON=0.AND.PON=0.AND.CON=0.AND
APPEND FROM TEMPDESIG
ENDIF
IF UCN=1
APPEND FROM TEMPDESIG FOR L='U'
ENDIF
IF MON=1
APPEND FROM TEMPDESIG FOR L='M'
EMDIF
IF TON=1
APPEND FROM TEMPDESIG FOR L='T'
ENDIF
IF HON=1
APPEND FROM TEMPDESIG FOR L='H'
ENDIF
IF AON=1
APPEND FROM TEMPDESIG FOR L='A'
ENDIF
IF SON=1.
APPEND FROM TEMPDESIG FOR L='S'
ENDIF
IF PON=1
APPEND FRGM TEMPDESIG FOR L='P'
ENDIF
IF CON=1
APPEND FROM TEMPDESIG FOR L='C'
ENDIF
IF ION=1
APPEND FROM TEMPDESIG FOR L='I'
ENDIF
IF YON=1
APPEND FROM TEMPDESIG FOR L='Y'
ENDIF
IF LON=1
APPEND FROM TEMPDESIG FOR L='L'
ENDIF
IF FON=1
APPEND FROM TEMPDESIG FOR L='F'
ENDIF
COUNT TO ANALTOT
USE TEMPDESIG
COPY STRUCTURE TO TEMPSUB
USE TEMPSUB
IF USUB=0 .AND. MSUB=0 .AND. TSUB=0 .AND. HSUB=0 .AND. ASUB=0.AND.SSUB=0.AND.PSUB=0.AND.CS
APPEND FROM TEMPDESIG
ENDIF
IF USUB=1
APPEND FROM TEMPDESIG FOR L='U'
ENDIF
IF MSUB=1
```

APPENDIX A-continued

```
APPEND FROM TEMPDESIG FOR L=.'M'
ENDIF
IF TSUB=1
APPEND FROM TEMPDESIG FOR L='T'
ENDIF
IF HSUB=1
APPEND FROM TEMPDESIG FOR L='H'
ENDIF
IF ASUB=1
APPEND FROM TEMPDESIG FOR L='A'
ENDIF
IF SSUB=1
APPEND FROM TEMPDESIG FOR L='S'
ENDIF
IF PSUB=1
APPEND FROM TEMPDESIG FOR L='P'
ENDIF
IF CSUB=1
APPEND FROM TEMPDESIG FOR L='C'
ENDIF
IF ISUB=1
APPEND FRCM TEMPDESIG FOR L='I'
ENDIF
IF YSUB=1
APPEND FROM TEMPDESIG FOR L='Y'
ENDIF
IF LSUB=1
APPEND FROM TEMPDESIG FOR L='L'
ENDIF
IF FSUB=1
APPEND FROM TEMPDESIG FOR L='F'
ENDIF
COUNT TO SUBTRACTOT
SET TALK OFF
****************************************************
* COMPRESSION SUBROUTINE A
? 'COMPRESSING QUERY LIBRARY'
USE TEMPLIB
SORT ON ENTRY,NUMBER TO LIBSORT
USE LIBSDRT
COUNT TO IDGENE
REPLACE ALL RFEND WITH 1
MARK1 = 1
SW2=0
DO WHILE SW2=0 ROLL
IF MARK1 >= IDGENE
PACK
COUNT TO AUNIQUE
SW2=1
LOOP
ENDIF
GO MARK1
DUP = 1
STORE ENTRY TO TESTA
STORE D TO DESIGA
SW = 0
DD WHILE SW=0 TEST
SKIP
STORE ENTRY TO TESTB
STORE D TO DESIGB
IF TESTA = TESTB.AND.DESIGA=DESIGB
DELETE
DUP = DUP+1
LCDP
ENDIF
GO MARK1
REPLACE RFEND WITH DUP
MARK1 = MARK1+DUP
SW=1
WOP
ENDDO TEST
WOP
ENDDO ROLL
SORT ON RFEND/D,NUMBER TG TEMPTARSORT
USE TEMPTARSORT
*REPLACE ALL START WITH RFEND/IDGENE*10000
COUNT TO TEMPTARCO
****************************************************
* COMPRESSION SUBROUTINE B
```

APPENDIX A-continued

```
? 'COMPRESSING TARGET LIBRARY'
*USE TEMPSUB
SORT ON ENTRY,NUMBER TO SUBSORT
USE SUBSORT
COUNT TO SUBGENE
REPLACE ALL RFEND WITH 1
MARK1 = 1
SW2=0
DO WHILE SW2=0 ROLL
IF MARK1 >= SUBGENE
PACK
COUNT TO BUNIQUE
SW2=1
LOOP
ENDIF
GO MARK1
DUP = 1
STORE ENTRY TO TESTA
STORE D TO DESICA
SW = 0
DO WHILE SW=0 TEST
SKIP
STORE ENTRY TO TESTB
STORE D TO DESIGB
IF TESTA = TESTB.AND.DESIGA=DESIGB
DELETE
DUP = DUP+1
LOOP
ENDIF
GO MARK1
REPLACE RFEND WITH DUP
MARK1 = MARK1+DUP
SW=1
WOP
ENDDO TEST
WOP
ENDDO ROLL
SORT ON RFEND/D,NUMBER TO TEMPSUBSORT
USE TEMPSUBSORT
*REPLACE ALL START WITH RFEND/IDGENE*10000
COUNT TO TEMPSUBCO
***********************************************
*FUSION ROUTINE
? 'SUBTRACTING LIBRARIES'
USE SUBTRACTION
COPY STRUCTURE TO CRUNCHER
SELECT 2
USE TEMPSUBSORT
SELECT 1
USE CRUNCHER
APPEND FROM TEMPTARSORT
COUNT TO BAILOUT
MARK = 0
DO WHILE .T.
SELECT 1
MARK = MARK+1
IF MARK>BAILOUT
EXIT
ENDIF
GO MARK
STORE ENTRY TO SCANNER
SELECT 2
LCCATE FOR ENTRY=SCANNER
IF FOUND()
STORE RFEND TO BIT1
STORE RFEND TO BIT2
ELSE
STORE ½ TO BIT1
STORE 0 TO BIT2
ENDIF
SELECT 1
REPLACE BGFREQ WITH BIT2
REPLACE ACTUAL WITH BIT1
LOOP
ENDDO
SELECT 1
REPLACE ALL RATIO WITH RFEND/ACTUAL
? 'DOING FINAL SORT BY RATIO'
SORT ON RATIO/D,BGFREQ/D,DESCRIPTOR TO FINAL
```

APPENDIX A-continued

```
USE FINAL
set talk off
DO CASE
CASE PTF=0
SET DEVICE TO PRINT
SET PRINT ON
CASE PTF= 1
SET ALTERNATE TO "INCT 20011:Subtraction 1"
SET ALTERNATE ON
ENDCASE
STORE VAL(SYS(2)) TO FINTIME
IF FINTIME<STARTIME
STORE FINTIME+86400 TO FINTIME
ENDIF
STORE FINTIME - STARTIME TO COMPSEC
STORE COMPSEC/60 TO COMPMIN
***************************
SET MARGIN TO 10
SAY "Library Subtraction Analysis"STYLE 65536 FONT "Geneva",274 COLOR 0,0,0,-1,-1,-1
?
?
?
?
? date()
??' '
?? TIME()
? 'Clone numbers'
?? STR(INITIATE,5,0)
??'through'
?? STR(TERMINATE,6,0)
? 'Libraries:'
IF UON=0 .AND. MON=0 .AND. TON=0.AND.HON=0.AND.AON=0.AND.SON=0.AND.PON=0.AND.CON=0.AND.YON=0
?? 'All'
ENDIF
IF UON=1
?? 'U937,'
ENDIF
IF MON=1
?? 'HMC,'
ENDIF
IF TON=1
?? 'THP-1'
ENDIF
IF HON=1
?? 'HUVEC'
ENDIF
IF AON=1
?? 'Adenoid'
ENDIF
IF SON=1
?? 'Spleen'
ENDIF
IF PON=1
?? 'Control THP'
ENDIF
IF CON=1
?? 'Control HUVEC'
ENDIF
IF YON=1
?? 'T + B lymphoblast'
ENDIF
IF ION=1
?? 'Corneal stroma'
ENDIF
IF LON=1
??'Liver'
ENDIF
IF FON=1
?? 'Fibroblast'
ENDIF
? 'Subtracting:'
IF USUB=0 .AND. MSUB=0 .AND. TSUB=0.AND.HSUB=0.AND.ASUB=C.AND.SSUB=0.AND.PSUB=0.AND.CSUB=0.A
?? 'All'
ENDIF
IF USUB=1
?? 'U937,'
ENDIF
IF MSUB=1
?? 'HMC,'
```

APPENDIX A-continued

```
ENDIF
IF TSUB=1
??'THP-1'
ENDIF
IF HSUB=1
?? 'HUVEC'
ENDIF
IF ASUB=1
??'Adenoid'
ENDIF
IF SSUB=1
?? 'Spleen'
ENDIF
IF PSUB=1
?? 'Control THP'
ENDIF
IF CSUB=1
?? 'Control HUVEC'
ENDIF
IF YSUB=1
?? 'T + B lymphoblast'
ENDIF
IF ISUB=1
?? 'Corneal stroma'
ENDIF
IF LSUB=1
?? 'Liver'
ENDIF
IF FSUB=1
?? 'Fibroblast'
ENDIF
? 'Designations:'
IF ETatch=0 .AND. Hmatch=0 .AND. Omatch=0 .AND. IMATCH=0
?? All'
ENDIF
IF Ematch=1
?? 'Exact,'
ENDIF
IF Hmatch=1
?? 'Human,
ENDIF
IF Qmatch=1
?? 'Other sp.'
ENDIF
IF Imatch=1
?? 'INCYTE'
ENDIF
IF ANAL=1
? 'Sorted by ABUNDANCE'
ENDIF
IF ANAL=2
? 'Arranged by FUNCTION'
ENDIF
? 'Total clones represented:'
?? STR(TCT,5,0)
? 'Total clones analyzed:'
?? STR(STARTOT,5,0)
? 'Total computation time ='
?? STR(COMPMIN,5,2)
?? 'minutes'
? 'd = designation f = distribution z = location r = function s = species i = inte
?
**************************************
SCREEN 1 TYPE 0 HEADING "Screen 1" AT 40,2 SIZE 286,492 PIXELS FONT "Geneva",9 COLOR 0,0,0,
DO CASE
CASE ANAL=1
?? STR(AUNIQUE,4,0)
'genes, for a total of'
?? STR(ANALTOT,4,0)
?? 'clones'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I
SET PRINT OFF
*CLOSE DATABASES
USE "SmartGuy:FoxBASE+/Mac: fox files:clones.dbf"
CASE ANAL=2
* arrange/function
SET PRINT CN
*SET HEADING ON
```

APPENDIX A-continued

```
SCREEN 1 TYPE 0 HEADING "Screen 1"AT 40,2 SIZE 286,492 PIXELS FONT "Helvitica",268 COLOR 0
?
?'BINDING PROTEINS'
?
SCREEN 1 TYPE 0 HEADING "Screen 1"AT 40,2 SIZE 286,492 PIXELS FONT "Helvitica",265 COLOR 0
? 'Surface molecules and receptors:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTGR,BGFREQ,RFEND,RATIO,I FOR R='B'
SCREEN 1 TYPE 0 HEADING "Screen 1"AT 40,2 SIZE 286,492 PIXELS FONT "Helvitica",265 COLOR 0
? 'Calcium-binding proteins:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='C'
SCREEN 1 TYPE 0 HEADING "Screen 1"AT 40,2 SIZE 286,492 PIXELS FONT "Helvitica",265 COLOR 0
? 'Ligands and effectors:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFFEQ,RFEND,RATIO,I FOR R='S'
SCREEN 1 TYPE 0 HEADING "Screen 1"AT 40,2 SIZE 286,492 PIXELS FONT "Helvitica",265 COLOR C
? 'Other binding proteins:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='I'
SCREEN 1 TYPE 0 HEADING "Screen 1"AT 40,2 SIZE 286,492 PIXELS FONT "Helvitica",268 COLOR 0
?'ONCOGENES'
?
SCREEN 1 TYPE 0 HEADING "Screen 1"AT 40,2 SIZE 286,492 PIXELS FONT "Helvitica",265 COLOR 0
? 'General oncogenes:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='O'
SCREEN 1 TYPE 0 HEADING "Screen 1"AT 40,2 SIZE 286,492 PIXELS FONT "Helvitica",265 COLOR 0
? 'GTP-binding proteins:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='G'
SCREEN 1 TYPE 0 HEADING "Screen 1"AT 40,2 SIZE 286,492 PIXELS FONT "Helvitica",265 COLOR 0
? 'Viral elements:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='V'
SCREEN 1 TYPE 0 HEADING "Screen 1"AT 40,2 SIZE 286,492 PIXELS FONT "Helvitica",265 COLOR 0
? 'Kinases and Phosphatases:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='Y'
SCREEN 1 TYPE 0 HEADING "Screen 1"AT 40,2 SIZE 286,492 PIXELS FONT "Helvitica",265 COLOR 0
?'Tumor-related antigens:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='A'
?
SCREEN 1 TYPE 0 HEADING "Screen 1"AT 40,2 SIZE 286,492 PIXELS FONT "Helvitica",268 COLOR 0
? 'PROTEIN SYNTHETIC MACHINERY PROTEINS'
?
SCREEN 1 TYPE 0 HEADING "Screen 1"AT 40,2 SIZE 286,492 PIXELS FONT "Helvitica",265 COLOR 0
? 'Transcription and Nucleic Acid-binding proteins:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='D'
SCREEN 1 TYPE 0 HEADING "Screen 1"AT 40,2 SIZE 286,492 PIXELS FONT "Helvitica",265 COLOR 0
? 'Translation:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='T'
SCREEN 1 TYPE 0 HEADING "Screen 1"AT 40,2 SIZE 286,492 PIXELS FONT "Helvitica",265 COLOR 0
? 'Ribosomal proteins:'
SCREEN 1 TYPE 0 HEADING "Screen 1"AT 40,2 SIZE 286,492 PIXELS *FONT "Geneva",7 COLOR 0,0,0,
list OFF fields number,D,F,Z,R,ENTRY,S,DESCRIPTOR,BGFREQ,RFEND,RATIO,I FOR R='R'
SCREEN 1 TYPE 0 HEADING "Screen 1"AT 40,2 SIZE 286,492 PIXELS FONT "Helvitica",265 COLOR 0
? 'Protein processing:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='L'
?
SCREEN 1 TYPE 0 HEADING "Screen 1"AT 40,2 SIZE 286,492 PIXELS FONT "Helvitica",268 COLOR 0
?
? 'ENZYMES'
?
SCREEN 1 TYPE 0 HEADING "Screen 1"AT 40,2 SIZE 286,492 PIXELS FONT "Helvitica",265 COLOR 0
? 'Ferroproteins:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='F'
SCREEN 1 TYPE 0 HEADING "Screen 1"AT 40,2 SIZE 286,492 PIXELS FONT "Helvitica",265 COLOR 0
? 'Proteases and inhibitors:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='P'
SCREEN 1 TYPE 0 HEADING "Screen 1"AT 40,2 SIZE 286,492 PIXELS FONT "Helvitica",265 COLOR 0
? 'Oxidative phosphorylation:'
SCREEN 1 TYPE 0 HEADING "Screen 1"AT 40,2 SIZE 286,492 PIXELS FONT "Geneva",7 COLOR 0,0,0,
```

APPENDIX A-continued

```
list OFF fields number,D,F,Z,R,ENTRY,S,DESCRIPTOR,BGFREQ,RFEND,RATIO,I FOR R='Z'
SCREEN 1 TYPE 0 HEADING "Screen 1"AT 40,2 SIZE 286,492 PIXELS FONT "Helvitica",265 COLOR 0
? 'Sugar metabolism:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='Q'
SCREEN 1 TYPE 0 HEADING "Screen 1"AT 40,2 SIZE 286,492 PIXELS FONT "Helvitica",265 COLOR 0
? 'Amino acid metabolism:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='M'
SCREEN 1 TYPE 0 HEADING "Screen 1"AT 40,2 SIZE 286,492 PIXELS FONT "Helvitica",265 COLOR 0
? 'Nucleic acid metabolism:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='N'
SCREEN 1 TYPE 0 HEADING "Screen 1"AT 40,2 SIZE 286,492 PIXELS FONT "Helvitical",265 COLOR 0
? 'Lipid metabolism:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='W'
SCREEN 1 TYPE 0 HEADING "Screen 1"AT 40,2 SIZE 286,492 PIXELS FONT "Helvitica",265 COLOR 0
? 'Other enzymes:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='E'
SCREEN 1 TYPE 0 HEADING "Screen 1"AT 40,2 SIZE 286,492 PIXELS FONT "Helvitica",268 COLOR 0
?
? 'MISCELLANEOUS CATEGORIES'
?
SCREEN 1 TYPE 0 HEADING "Screen 1"AT 40,2 SIZE 286,492 PIXELS FONT "Helvitica",265 COLOR 0
? 'Stress response:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='H'
SCREEN 1 TYPE 0 HEADING "Screen 1"AT 40,2 SIZE 286,492 PIXELS FONT "Helvitica",265 COLOR 0
? 'Structural:'
SCREEN 1 TYPE 0 HEADING "Screen 1"AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='K'
SCREEN 1 TYPE 0 HEADING "Screen 1"AT 40,2 SIZE 286,492 PIXELS FONT "Helvitica",265 COLOR 0
? 'Other clones:'
SCREEN 1 TYPE 0 HEADING "Screen 1"AT 40,2 SIZE 286,492 PIXELS FONT "Geneva",7 COLOR 0,0,0,
list OFF fields nubher,D,F,Z,R,ENTRY,S,DESCRIPTOR,BGFREQ,RFEND,RATIO,I FOR R='X'
SCREEN 1 TYPE 0 HEADING "Screen 1"AT 40,2 SIZE 286,492 PIXELS FONT "Helvitica",265 COLOR 0
? 'Clones of unknown function:'
SCREEN 1 TYPE 0 HEADING "Screen 1"AT 40,2 SIZE 286,492 PIXELS FONT "Geneva",7 COLOR. 0,0,0,
list OFF fields number,D,F,Z,R,ENTRY,S,DESCRIPTOR,BGFREQ,RFEND,RATIO,I FOR R='U'
ENDCASE
DO "Test print.prg"
SET PRINT OFF
SET DEVICE TO SCREEN
CLOSE DATABASES
ERASE TEMPLIB.DBF
ERASE TEMPNUM.DBF
ERASE TEMPDESIG.DBF
SET MARGIN TO 0
CLEAR
LOOP
ENDDO
```

TABLE 1

NSEC Clone Descriptors

The following are the current descriptors used to describe each clone in the NSEC database (where information is available):

| | |
|---|---|
| Library (L): | Denotes the cDNA library of clone origin |
| Designation (D): | Describes general category of the clone (e.g. match to a prior sequence, new clone, or non-useable clone) |
| Certainty (C): | Denotes clones where the designataion is ambiguous and further work is required to establish true identity |
| Species (S): | Indicates species from which database match was derived |
| Orientation (O): | A (<) indicates match was found in the opposite orientation (limited to certain analyses) |
| Distribution (F): | Describes whether the clone is found in all tissues and cells, or whether its expression is limited its occurrence |
| Localization (Z): | Describes where in the cell the protein is normally found |
| Function (R): | Describes the functional class of the protein |

TABLE 1

| Designations (D) | Distribution (F) | Localization (Z) | Function (R) |
|---|---|---|---|
| E = Exact | C = Non-specific | N = Nuclear | T = Translation |
| H = Homologous | P = Cell/tissue specific | C = Cytoplasmic | L = Protein processing |
| O = Other species | U = Unknown | K = Cytoskeleton | R = Ribosomal protein |
| N = No match | | E = Cell surface | O = Oncogene |
| D = Noncoding gene | | Z = Intracellular memb | G = GTP binding ptn |
| U = Nonreadable | | M = Mitochondrial | V = Viral element |
| R = Repetitive DNA | | S = Secreted | Y = Kinase/phosphatase |
| A = Poly-A only | Species | U = Unknown | A = Tumor antigen related |
| V = Vector only | (S) | X = Other | I = Binding proteins |
| M = Mitochondrial DNA | | | D = NA-binding /transcription |
| S = Skip | H = Human | | B = Surface molecule/receptor |
| I = Match Incyte clone | A = Ape | | C = $Ca^{++}$ binding protein |
| X = EST match | P = Pig | | S = Ligands/effectors |
| | D = DOg | | H = Stress response protein |
| Library | V = Bovine | Status | E = Enzyme |
| (L) | B = Rabbit | (I) | F = Ferroprotein |
| | R = Rat | | P = Protease/inhibitor |
| U = U937 | M = Mouse | 0 = No current interest | Z = Oxidative phosphorylation |
| M = HMC | S = Hamster | 1 = DO primary analysis | Q = Sugar metabolism |
| T = THP-1 | C = Chicken | 2 = Primary analysis done | M = Amino acid metabolism |
| H = HUVEC | F = Amphibian | 3 = Full length sequence | N = Nucleic acid metabolism |
| S = Spleen | I = Invertebrate | 4 = Secondary analysis | W = Lipid metabolism |
| L = Lung | Z = Protozoan | 5 = Tissue northern | K = Structural |
| Y = T & B cell | G = Fungi | 6 = Obtain full length | X = Other |
| A = Adenoid | | | U = unknown |

TABLE 2

Clone numbers 15000 through 20000
Libraries: HUVEC
Designations: All
Condensed format analysis
Arranged by ABUNDANCE
Total clones represented: 5000
Total clones analyzed: 5000
l = library d = designation f = distribution z = location r = function c = certain? s = species
319 genes, for a total of 1713 clones

| Coincidence number | V N | V Clones/10000 % | l | d | f | z | r | c | entry | s descriptor | length | init | i |
|---|---|---|---|---|---|---|---|---|---|---|---|---|---|
| 1 | 15365 | 67 867 | H | E | C | C | R | | HSRPL41 | Ribosomal protein L41 | 91 | 0 | |
| 2 | 15004 | 65 841 | H | I | U | U | U | | NCY015004 | INCYTE clone 015004 | 0 | 2 | |
| 3 | 15638 | 63 815 | H | I | U | U | U | | NCY015638 | INCYTE clone 015638 | 0 | 0 | |
| 4 | 15390 | 50 647 | H | I | U | U | U | | NCY015390 | INCYTE clone 015390 | 0 | 0 | |
| 5 | 15193 | 47 608 | H | E | C | S | I | | HSFIB1 | Fibronectin | 829 | 0 | |
| 6 | 15220 | 47 608 | H | O | C | C | R | | RRRPL9 | R Ribosomal protein L9 | 547 | 0 | |
| 7 | 15280 | 47 608 | H | I | U | U | U | | NCY015280 | INCYTE clone 015280 | 0 | 0 | |
| 8 | 15583 | 33 427 | H | X | U | U | U | | M62060 | EST HHCH09 (IGR) | -60 | 0 | |
| 9 | 15662 | 31 401 | H | E | C | K | K | | HSACTCGR | Actin, cytoskeletal gamma | 41 | 0 | |
| 10 | 15026 | 29 375 | H | I | U | U | U | | NCY015026 | INCYTE clone 015026 | 0 | 0 | |
| 11 | 15279 | 24 310 | H | E | C | C | T | | HSEF1AR | Elongation factor 1-alpha | 871 | 0 | |
| 12 | 15027 | 23 298 | H | I | U | U | U | | NCYO15027 | INCYTE clone 015027 | 0 | 0 | |
| 13 | 15033 | 20 259 | H | I | U | U | U | | NCY015033 | INCYTE clone 015033 | 0 | 0 | |
| 14 | 15198 | 20 259 | H | I | U | U | U | | NCYO15198 | INCYTE clone 015198 | 0 | 0 | |
| 15 | 15809 | 20 259 | H | E | P | S | P | | HSCOLL1 | Collagenase | 1228 | 0 | |
| 16 | 15221 | 19 246 | H | I | U | U | U | | NCY015221 | INCYTE clone 015221 | 0 | 0 | |
| 17 | 15263 | 19 246 | H | I | U | U | U | | NCY015263 | INCYTE clone 015263 | 0 | 0 | |
| 18 | 15290 | 19 246 | H | I | U | U | U | | NCY015290 | INCYTE clone 015290 | 0 | 0 | |
| 19 | 15350 | 18 233 | H | I | U | U | U | | NCY015350 | INCYTE clone 015350 | 0 | 0 | |
| 20 | 15030 | 17 220 | H | I | U | U | U | | NCY015030 | INCYTE clone 015030 | 0 | 0 | |
| 21 | 15234 | 17 220 | H | I | U | U | U | | NCY015234 | INCYTE clone 015234 | 0 | 0 | |

TABLE 2

| 22 | 15459 | 16 207 | H I U U U | NCY015459 | INCYTE clone 015459 | 0 | 0 |
|---|---|---|---|---|---|---|---|
| 23 | 15353 | 15 194 | H I U U U | NCY015353 | INCYTE clone 015353 | 0 | 0 |
| 24 | 15378 | 15 194 | H E P C Y | S76965 | Protein kinase inhibitor | -571 | 0 |
| 25 | 15255 | 14 181 | H E P U U | HUMTHYB4 | Thyrnosin beta-4 | 168 | 0 |
| 26 | 15401 | 14 181 | H E P Z C | HSLIPCR | Lipocortin I | 394 | 0 |
| 27 | 15425 | 14 181 | H E C C T | HSPOLYAB | Poly-A binding protein | 1583 | 0 |
| 28 | 18212 | 14 181 | H E P U U | HUMTHYMA | Thyrnosin, alpha | -120 | 0 |
| 29 | 18216 | 14 181 | H E P E X | HSMRP1 | Motility related protein; MRP-1; CD-9 | 80 | 0 |

TABLE 2-continued

| | | | | | | | | |
|---|---|---|---|---|---|---|---|---|
| 30 | 15189 | 13 | 168 | H E P U H | HS18D | Interferon inducible protein 1-8D | 356 | 0 |
| 31 | 15031 | 12 | 155 | H E P C I | HUMFKBP | FK506 binding protein | −65 | 0 |
| 32 | 15306 | 12 | 155 | H E C N D | HSH2AZ | Histone H2A | −32 | 0 |
| 33 | 15621 | 12 | 155 | H E P E B | HUMLEC | Lectin, B-galactosidase binding, 14 kDa | 428 | 0 |
| 34 | 15789 | 11 | 142 | H I U U U | NCY015789 | INCYTE clone 015789 | 0 | 0 |
| 35 | 16578 | 11 | 142 | H E C C R | HSRPS11 | Ribosomal protein S11 | 424 | 0 |
| 36 | 16632 | 11 | 142 | H X U U U | M61984 | EST HHCA13 (IGR) | 0 | 0 |
| 37 | 18314 | 11 | 142 | H I U U U | NCY018314 | INCYTE clone 018314 | 0 | 0 |
| 38 | 15367 | 10 | 129 | H I U U U | NCY015367 | INCYTE clone 015367 | 0 | 0 |
| 39 | 15415 | 10 | 129 | H E U U H | HSIFNIN1 | interferon inducible mRNA 1-18D | 457 | 0 |
| 40 | 15633 | 10 | 129 | H E C C Q | HSLDHAR | Lactate dehydrogenase | 228 | 0 |
| 41 | 15813 | 10 | 129 | H O P K K | CHKNMHCB C | Myosin heavy chain B, nonmuscle | −1017 | 0 |
| 42 | 18210 | 10 | 129 | H I U U U | NCY018210 | INCYTE clone 018210 | 0 | 2 |
| 43 | 18233 | 10 | 129 | H E C N D | HSRPII140 | RNA polymerase II, 140 kDa subunit | 442 | 0 |
| 44 | 18996 | 10 | 129 | H I U U U | NCY018996 | INCYTE clone 018996 | 0 | 0 |
| 45 | 15088 | 9 | 116 | H E C C F | HUMFERL | Ferritin, light chain | −271 | 0 |
| 46 | 15714 | 9 | 116 | H I U U U | NCY015714 | INCYTE clone 015714 | 0 | 0 |
| 47 | 15720 | 9 | 116 | H I U U U | NCY015720 | INCYTE clone 015720 | 0 | 0 |
| 48 | 15863 | 9 | 116 | H I U U U | NCY015863 | INCYTE clone 015863 | 0 | 0 |
| 49 | 16121 | 9 | 116 | H E P S S | HSET | Endothelin; vasoconstrictor peptide | 878 | 0 |
| 50 | 18252 | 9 | 116 | H I U U U | NCY0182S2 | INCYTE clone 018252 | 0 | 0 |
| 51 | 15351 | 8 | 103 | H E P C I | HUMALBP | Lipid binding protein, adipocyte | 441 | 0 |
| 52 | 15370 | 8 | 103 | H I U U U | NCY015370 | INCYTE clone 015370 | 0 | 0 |
| 53 | 15670 | 8 | 103 | H O C M Z | BTCIASHI V | NADH-ubiquinone oxidoreductase CI-ASHI | 555 | 0 |
| 54 | 15795 | 8 | 103 | H I U U U | NCY015795 | INCYTE clone 015795 | 0 | 0 |
| 55 | 16245 | 8 | 103 | H I U U U | NCY016245 | INCYTE clone 016245 | 0 | 0 |
| 56 | 18262 | 8 | 103 | H I U U U | NCY018262 | INCYTE clone 018262 | 0 | 0 |
| 57 | 18321 | 8 | 103 | H E C C R | HSRPL17 | Ribosomal protein L17 | 425 | 0 |
| 58 | 15126 | 7 | 91 | H O C C R | XLRPL1BR F | Ribosomal protein L1 | −72 | 0 |
| 59 | 15133 | 7 | 91 | H E C K K | HSAC07 | Actin, beta- | 2236 | 0 |
| 60 | 15245 | 7 | 91 | H I U U U | NCY015245 | INCYTE clone 015245 | 0 | 0 |
| 61 | 15288 | 7 | 91 | H I U U U | NCY015288 | INCYTE clone 015288 | 0 | 0 |
| 62 | 15294 | 7 | 91 | H E C C Q | HSGAPDR | Glyceraldehyde 3-PO4 dehydrogenase | 763 | 0 |
| 63 | 15442 | 7 | 91 | H E P E B | HUMLAMB | Laminin receptor, 54kDa | 902 | 0 |
| 64 | 15485 | 7 | 91 | H E C C N | HSNGMRNA | Uracil DNA glycosylase | 747 | 0 |
| 65 | 16646 | 7 | 91 | H I U U U | NCY016646 | INCYTE clone 016646 | 0 | 0 |
| 66 | 18003 | 7 | 91 | H E P S S | HUMPAIA | Plsmnogen activator gene (5'-upstrm) | −1465 | 0 |
| 67 | 15032 | 6 | 78 | H E C C L | HUMUB | Ubiquitin | 458 | 0 |
| 68 | 15267 | 6 | 78 | H E C C R | HSRPS8 | Ribosomal protein S8 | −2004 | 0 |
| 69 | 15295 | 6 | 78 | H I U U U | NCY015295 | INCYTE clone 015295 | 0 | 0 |
| 70 | 15458 | 6 | 78 | H O C C R | RNRPS10R R | Ribosomal protein S10 | 497 | 0 |
| 71 | 15832 | 6 | 78 | H O C C Q | RSGALEM R | UDP-galactose epimerase | 888 | 2 |
| 72 | 15928 | 6 | 78 | H E P S I | HUMAPOJ | Apolipoprotein J | 202 | 0 |
| 73 | 16598 | 6 | 78 | H E C K K | HUMT-BBM40 | Tubulin, beta | −705 | 0 |
| 74 | 18218 | 6 | 78 | H I U U U | NCY018218 | INCYTE clone 018218 | 0 | 0 |
| 75 | 18499 | 6 | 78 | H E P U X | HSP27 | Hydrophobic protein p27; IFN inducible | 395 | 0 |
| 76 | 18963 | 6 | 78 | H I U U U | NCY018963 | INCYTE clone 018963 | 0 | 0 |
| 77 | 18997 | 6 | 78 | H I U U U | NCY018997 | INCYTE clone 018997 | 0 | 0 |
| 78 | 15432 | 5 | 65 | H E C C Q | HSAGALAR | Galactosidase A, alpha | 1004 | 0 |
| 79 | 15475 | 5 | 65 | H I U U U | NCY015475 | INCYTE clone 015475 | 0 | 0 |
| 80 | 15721 | 5 | 65 | H I U U U | NCY0T5721 | INCYTE clone 015721 | 0 | 0 |
| 81 | 15865 | 5 | 65 | H I U U U | NCY015865 | INCYTE clone 015865 | 0 | 0 |
| 82 | 16270 | 5 | 65 | H I U U U | NCY016270 | INCYTE clone 016270 | 0 | 0 |
| 83 | 16886 | 5 | 65 | H I U U U | NCY016886 | INCYTE clone 016886 | 0 | 2 |
| 84 | 18500 | 5 | 65 | H I U U U | NCY018500 | INCYTE clone 018500 | 0 | 0 |
| 85 | 18503 | 5 | 65 | H I U U U | NCY018503 | INCYTE clone 018503 | 0 | 0 |
| 86 | 19672 | 5 | 65 | H O C C R | RRRPL34 R | ribosomal protein L34 | 323 | 0 |
| 87 | 15086 | 4 | 52 | H O C C R | XLRPL1AR F | Ribosomal protein L1a | 913 | 0 |
| 88 | 15113 | 4 | 52 | H E C C T | HUMIFN-WRS | tRNA synthetase, tryptophanyl; IFN-ind | −112 | 0 |
| 89 | 15242 | 4 | 52 | H I U U U | NCY015242 | INCYTE clone 015242 | 0 | 0 |
| 90 | 15249 | 4 | 52 | H I U U U | NCY015249 | INCYTE clone 015249 | 0 | 0 |
| 91 | 15377 | 4 | 52 | H I U U U | NCY015377 | INCYTE clone 015377 | 0 | 0 |
| 92 | 15407 | 4 | 52 | H I U U U | NCY015407 | INCYTE clone 015407 | 0 | 0 |
| 93 | 15473 | 4 | 52 | H I U U U | NCY015473 | INCYTE clone 015473 | 0 | 0 |
| 94 | 15588 | 4 | 52 | H E C C R | HSRPS12 | Ribosomal protein S12 | 218 | 0 |
| 95 | 15684 | 4 | 52 | H E C C T | HSEF1G | Elongation factor 1-gamma | 378 | 0 |
| 96 | 15782 | 4 | 52 | H I U U U | NCY015782 | INCYTE clone 015782 | 0 | 0 |
| 97 | 15916 | 4 | 52 | H E C C R | HSRPS18 | Ribosomal protein S18 | 522 | 0 |
| 98 | 15930 | 4 | 52 | H I U U U | NCY015930 | INCYTE clone 015930 | 0 | 0 |
| 99 | 16108 | 4 | 52 | H I U U U | NCY016108 | INCYTE clone 016108 | 0 | 0 |
| 100 | 16133 | 4 | 52 | H I U U U | NCY016133 | INCYTE clone 016133 | 0 | 0 |
| 101 | 16211 | 4 | 52 | H X U UU | M85502 | EST HFBCJ05 (IGR) | 0 | 0 |
| 102 | 16301 | 4 | 52 | H X U UU | M78204 | EST 01797 (IGR) | 0 | 0 |
| 103 | 16412 | 4 | 52 | H E C C R | HUMRPS7A | Ribosomal protein S7a | 472 | 0 |
| 104 | 16413 | 4 | 52 | H I U U U | NCY016413 | INCYTE clone 016413 | 0 | 0 |
| 105 | 16651 | 4 | 52 | H I U U U | NCY016651 | INCYTE clone 016651 | 0 | 0 |

TABLE 2-continued

| | | | | | | | | | |
|---|---|---|---|---|---|---|---|---|---|
| 106 | 16668 | 4 | 52 | H E P S S | | HSEPIT1 | Growth factor, epithelial cell (EGF) | 132 | 0 |
| 107 | 17645 | 4 | 52 | H X U U U | | M62279 | EST HHCC14 (IGR) | 0 | 0 |
| 108 | 19175 | 4 | 52 | H X U U U | R | HSAAABTZR | EST AAABTZR (UK-HGMP) | 0 | 0 |
| 109 | 15028 | 3 | 39 | H E C C R | | HUMSRAA | Ribosomal protein S16 | 343 | 0 |
| 110 | 15047 | 3 | 39 | H E C C O | | HSTUMP | Translation controlled tumor protein | 593 | 0 |
| 111 | 15061 | 3 | 39 | H E P E B | | HSFNRB | Fibronectin receptor beta subunit | 227 | 0 |
| 112 | 15079 | 3 | 39 | H X U U U | | M79268 | EST 01423 (Venter) | 0 | 0 |
| 113 | 15104 | 3 | 39 | H I U U U | | NCY015T04 | INCYTE clone 015104 | 0 | 0 |
| 114 | 15123 | 3 | 39 | H E C C R | | HUMRPL18A | Ribosomal protein L18 | 560 | 0 |
| 115 | 15190 | 3 | 39 | H E P S S | | HUMMCAF | Chemotactic protein MCP-1, monocyte | 330 | 0 |
| 116 | 15299 | 3 | 39 | H E C C Q | | HUMTPI | Triosephosphate isomerase | 9 | 0 |
| 117 | 15357 | 3 | 39 | H I U U U | | NCY015357 | INCYTE clone 015357 | 0 | 0 |
| 118 | 15368 | 3 | 39 | H I U U U | | NCY015368 | INCYTE clone 015368 | 0 | 0 |
| 119 | 15454 | 3 | 39 | H I U U U | | NCY015454 | INCYTE clone 015454 | 0 | 0 |
| 120 | 15506 | 3 | 39 | H I U U U | | NCY015506 | INCYTE clone 015506 | 0 | 0 |
| 121 | 15507 | 3 | 39 | H I U U U | | NCY015507 | INCYTE clone 015507 | 0 | 0 |
| 122 | 15510 | 3 | 39 | H I U U U | | NCY015510 | INCYTE clone 015510 | 0 | 0 |
| 123 | 15517 | 3 | 39 | H I U U U | | NCY0T5517 | INCYTE clone 015517 | 0 | 0 |
| 124 | 15774 | 3 | 39 | H O C C R | | RNRPL37 R | Ribosomal protein L37 | 3223 | 0 |
| 125 | 15785 | 3 | 39 | H E P K K | | HSMRLCM | Myosin regulatory L chain | 440 | 0 |
| 126 | 15919 | 3 | 39 | H I U U U | | NCY015919 | INCYTE clone 015919 | 0 | 0 |
| 127 | 15936 | 3 | 39 | H I U U U | | NCY015936 | INCYTE clone 015936 | 0 | 0 |
| 128 | 15937 | 3 | 39 | H I U U U | | NCY015937 | INCYTE clone 015937 | 0 | 0 |
| 129 | 15955 | 3 | 39 | H I U U U | | NCY015955 | INCYTE clone 015955 | 0 | 0 |
| 130 | 16071 | 3 | 39 | H I U U U | | NCY016071 | INCYTE clone 016071 | 0 | 0 |
| 131 | 16868 | 3 | 39 | H I U U U | | NCY016868 | INCYTE clone 016868 | 0 | 0 |
| 132 | 16923 | 3 | 39 | H E C M Z | | HUMTLCA | ADP/ATP translocase | 289 | 0 |
| 133 | 17097 | 3 | 39 | H I U U U | | NCY017097 | INCYTE clone 017097 | 0 | 0 |
| 134 | 17114 | 3 | 39 | H E C C R | | HUMRRL3A | Ribosomal protein L3 | 303 | 0 |
| 135 | 17160 | 3 | 39 | H I U U U | | NCY017160 | INCYTE clone 017160 | 0 | 0 |
| 136 | 17530 | 3 | 39 | H I U U U | | NCY017530 | INCYTE clone 017530 | 0 | 0 |
| 137 | 17543 | 3 | 39 | H E P E B | | HSLAMBR | laminin binding protein | 0 | 0 |
| 138 | 17599 | 3 | 39 | H X U U U | | T02946 | EST FB17B2 (Sikela) | 0 | 0 |
| 139 | 17602 | 3 | 39 | H I U U U | | NCY017602 | INCYTE clone 017602 | 0 | 0 |
| 140 | 17700 | 3 | 39 | H E C N D | | HUMBTFC | BTF3 tcr factor; Fc gamma receptor IIB | −36 | 0 |
| 141 | 18085 | 3 | 39 | H I U U U | | NCY018085 | INCYTE clone 018085 | 0 | 0 |
| 142 | 18086 | 3 | 39 | H E C C R | | HUMRPS4X | Ribosomal protein S4 | 742 | 0 |
| 143 | 18258 | 3 | 39 | H I U U U | | NCY018258 | INCYTE clone 018258 | 0 | 0 |
| 144 | 18259 | 3 | 39 | H X U U U | | M62278 | EST HHCJ64 (IGR) | 0 | 0 |
| 145 | 18306 | 3 | 39 | H I U U U | | NCY018306 | INCYTE clone 018306 | 0 | 0 |
| 146 | 18324 | 3 | 39 | H E C N D | | HUMHMG14 | Non-histone DNA-binding protein | −156 | 0 |
| 147 | 18512 | 3 | 39 | H I U U U | | NCY018512 | INCYTE clone 018512 | 0 | 0 |
| 148 | 18635 | 3 | 39 | H I U U U | | NCY018635 | INCYTE clone 018635 | 0 | 0 |
| 149 | 18870 | 3 | 39 | H E P C Y | | HSCL100 | Tyrosine phosphatase CL 100 | −107 | 0 |
| 150 | 18968 | 3 | 39 | H I U U U | | NCY018968 | INCYTE clone 018968 | 0 | 0 |
| 151 | 19143 | 3 | 39 | H I U U U | | NCY019143 | INCYTE clone 019143 | 0 | 0 |
| 152 | 19186 | 3 | 39 | H I U U U | | NCY019186 | INCYTE clone 019186 | 0 | 0 |
| 153 | 19358 | 3 | 39 | H H U U P | | SYNSTFBFP | MS-2; homologous to cystatin beta | 148 | 3 |
| 154 | 19760 | 3 | 39 | H I U U U | | NCY019760 | INCYTE clone 019760 | 0 | 0 |
| 155 | 19783 | 3 | 39 | H O U C W | | S80257 P | Phospholipid H-peroxide GT peroxidase | 436 | 1 |
| 156 | 15029 | 2 | 26 | H X U U U | | HUMXT01423 | EST 01423 | 0 | 0 |
| 157 | 15044 | 2 | 26 | H I U U U | | NCY015044 | INCYTE clone 015044 | 0 | 0 |
| 158 | 15092 | 2 | 26 | H I U U U | | NCY015092 | INCYTE clone 015092 | 0 | 0 |
| 159 | 15093 | 2 | 26 | H I U U U | | NCY015093 | INCYTE clone 015093 | 0 | 0 |
| 160 | 15136 | 2 | 26 | H O C C R | | RNRIPRL38 R | Ribosomal protein L38 | 0 | 0 |
| 161 | 15191 | 2 | 26 | H E C C I | | HSTHIO | Metallothionein | 0 | 0 |
| 162 | 15203 | 2 | 26 | H I U U U | | NCY015203 | INCYTE clone 015203 | 0 | 0 |
| 163 | 15272 | 2 | 26 | H E C N V | | HUMRIRT | Retinoic acid inducible retrovirus | 0 | 0 |
| 164 | 15297 | 2 | 26 | H I U U U | | NCY015297 | INCYTE clone 015297 | 0 | 0 |
| 165 | 15303 | 2 | 26 | H I U U U | | NCY015303 | INCYTE clone 015303 | 0 | 0 |
| 166 | 15356 | 2 | 26 | H O C C R | | RRRPL21 R | Ribosomal protein L21 | 508 | 0 |
| 167 | 15366 | 2 | 26 | H I U U U | | NCY015366 | INCYTE clone 015366 | 0 | 0 |
| 168 | 15371 | 2 | 26 | H E C N D | | HUMH2AZ | Histone H2A.Z | 188 | 0 |
| 169 | 15381 | 2 | 26 | H E C K K | | HUMPROF | Profilin | 214 | 0 |
| 170 | 15570 | 2 | 26 | H I U U U | | NCY015570 | INCYTE clone 015570 | 0 | 0 |
| 171 | 15643 | 2 | 26 | H E U E B | | HUMQM | Laminin rcptr homolog; Wilm's tmr rel | 629 | 0 |
| 172 | 15652 | 2 | 26 | H I U U U | | NCY0156S2 | INCYTE clone 015652 | 0 | 0 |
| 173 | 15711 | 2 | 26 | H E U U Q | | HUML6A | Tumor antigen L6 | 367 | 0 |
| 174 | 15776 | 2 | 26 | H E U U U | | HS23KDHBP | Highly basic protein, 23 kDa | 594 | 0 |
| 175 | 15788 | 2 | 26 | H E P S P | | HUM4COLA | Collagenase, type IV | −291 | 0 |
| 176 | 15817 | 2 | 26 | H I U U U | | NCY015817 | INCYTE clone 015817 | 0 | 0 |
| 177 | 15833 | 2 | 26 | H E U U U | | HSPGP95 | Neuroendocrine protein PGP 9,5 | −113 | 0 |
| 178 | 15834 | 2 | 26 | H I U U U | | NCY015834 | INCYTE clone 015834 | 0 | 0 |
| 179 | 15848 | 2 | 26 | H I U U U | | NCY015848 | INCYTE clone 015848 | 0 | 0 |
| 180 | 15854 | 2 | 26 | H I U U U | | NCY015854 | INCYTE clone 015854 | 0 | 0 |
| 181 | 15858 | 2 | 26 | H I U U U | | NCY015858 | INCYTE clone 015858 | 0 | 0 |
| 182 | 15866 | 2 | 26 | H I U U U | | NCY015866 | INCYTE clone 015866 | 0 | 0 |
| 183 | 15868 | 2 | 26 | H E C C W | | HUMSAP1 | Saposin B; sphingolipid activator ptn | −492 | 0 |
| 184 | 15887 | 2 | 26 | H E C C T | | HSWRSX11 | tRNA synthetase, tryptophanyl | 414 | 0 |

TABLE 2-continued

| | | | | | | | | | |
|---|---|---|---|---|---|---|---|---|---|
| 185 | 15920 | 2 | 26 | H I U U U | NCY015920 | INCYTE clone 015920 | | 0 | 0 |
| 186 | 15932 | 2 | 26 | H I U U U | NCY015932 | INCYTE clone 015932 | | 0 | 0 |
| 187 | 16004 | 2 | 26 | H I U U U | NCY016004 | INCYTE clone 016004 | | 0 | 0 |
| 188 | 16188 | 2 | 26 | H I U U U | NCY016188 | INCYTE clone 016188 | | 0 | 0 |
| 189 | 16210 | 2 | 26 | H I U U U | NCY016210 | INCYTE clone 016210 | | 0 | 0 |
| 190 | 16401 | 2 | 26 | H I U U U | NCY016401 | INCYTE clone 016401 | | 0 | 0 |
| 191 | 16554 | 2 | 26 | H I U U U | NCY016554 | INCYTE clone 016554 | | 0 | 0 |
| 192 | 16572 | 2 | 26 | H I U U U | NCY016572 | INCYTE clone 016572 | | 0 | 0 |
| 193 | 16625 | 2 | 26 | H E P S P | HUMPAI | Plastminogen activator inhibitor 1 | | −880 | 0 |
| 194 | 16635 | 2 | 26 | H E U U U | HSPLAX | PLA-X | | 412 | 0 |
| 195 | 16777 | 2 | 26 | H E C C Y | HUM-CAMPPK | Protein kinase, cAMP-dependent,type 1a | | −1172 | 0 |
| 196 | 16951 | 2 | 26 | H X U U U | HUM000S3l7 | EST s317 (Okubo) | | −150 | 0 |
| 197 | 17024 | 2 | 26 | H E P C F | HUMFERH | Ferritin, heavy chain | | 376 | 0 |
| 198 | 17051 | 2 | 26 | H I U U U | NCY0l7O5l | INCYTE clone 017051 | | 0 | 0 |
| 199 | 17169 | 2 | 26 | H I U U U | NCY017169 | INCYTE clone 017169 | | 0 | 0 |
| 200 | 17728 | 2 | 26 | H E C C R | HSHUMS3 | Ribosomal protein S3 | | 721 | 0 |
| 201 | 17949 | 2 | 26 | H I U U U | NCY017949 | INCYTE clone 017949 | | 0 | 0 |
| 202 | 18000 | 2 | 26 | H E P S S | HUMCONGRO | Growth factor, connective tissue | | −55 | 0 |
| 203 | 18035 | 2 | 26 | H E C K K | HUMTUBAK | Tubulin, alpha | | 947 | 0 |
| 204 | 18230 | 2 | 26 | H I U U U | NCY018230 | INCYTE clone 018230 | | 0 | 0 |
| 205 | 18261 | 2 | 26 | H E C C R | HSRPL6AA | Ribosomal protein L6 | | 481 | 0 |
| 206 | 18309 | 2 | 26 | H E C K K | HUMTRO | Tropomyosin | | 73 | 0 |
| 207 | 18579 | 2 | 26 | H O C C M | RATODCAC | R | Ornithine decarboxylase antizyme | 1999 | 0 |
| 208 | 18696 | 2 | 26 | H E P C I | HSCYCR | Cyclophilin, T-cell | | 292 | 0 |
| 209 | 18810 | 2 | 26 | H O U U U | MUSTUM-SEQC | M | TNF-induced gene; poly A site | 867 | 0 |
| 210 | 18964 | 2 | 26 | H I U U U | NCY018964 | INCYTE clone 018964 | | 0 | 0 |
| 211 | 19169 | 2 | 26 | H I U U U | NCY019169 | INCYTE clone 019169 | | 0 | 0 |
| 212 | 19308 | 2 | 26 | H E C N D | HUMHISH3B | Histone H3.3 | | 58 | 0 |
| 213 | 19309 | 2 | 26 | H E P K K | HUMMYLCB | Non-muscle myosin alkali lt. chain 3'e | | 330 | 0 |
| 214 | 19362 | 2 | 26 | H I U U U | NCY019362 | INCYTE clone 019362 | | 0 | 0 |
| 215 | 19712 | 2 | 26 | H I U U U | NCY019712 | INCYTE clone 019712 | | 0 | 0 |
| 216 | 19787 | 2 | 26 | H I U U U | NCY019787 | INCYTE clone 019787 | | 0 | 0 |
| 217 | 19901 | 2 | 26 | H X U U U | HSAFICOO9 | EST FIc009 (Genexpress) | | 0 | 0 |
| 218 | 15042 | 1 | 13 | H O C C R | XELRPL1BR | F | Ribosomal protein L1b | 931 | 0 |
| 219 | 15138 | 1 | 13 | H E P S S | 571513 | Chemotactic fctr MCAF, monocyte; MCP1 | | 352 | 0 |
| 220 | 15160 | 1 | 13 | H E P S S | HUMIL1 | Interleukin-1 beta | | 855 | 0 |
| 221 | 15168 | 1 | 13 | H O P C C | RABPCALG | B | Calgizzarin, lung | 290 | 0 |
| 222 | 15173 | 1 | 13 | H E C N T | HSRNPA1 | hnRNP core protein A1 | | 470 | 0 |
| 223 | 15237 | 1 | 13 | H E U E B | HSKDEL | KDEL receptor | | 265 | 0 |
| 224 | 15239 | 1 | 13 | H X U U U | M78695 | EST HHCMC28 (IGR) | | 0 | 0 |
| 225 | 15320 | 1 | 13 | H E P S P | HUMCTSB | Cathepsin B | | 829 | 0 |
| 226 | 15403 | 1 | 13 | H X U U U | HSAFIAO44 | EST FIa044 (Genethon) | | 0 | 0 |
| 227 | 15460 | 1 | 13 | H E C C E | HUMARF1BA | ADP-ribosylation factor 1 (ARF1) | | 528 | 0 |
| 228 | 15512 | 1 | 13 | H E C C R | HUMS19RP | Ribosomal protein S19 | | 440 | 0 |
| 229 | 15601 | 1 | 13 | H X U U U | HSAAACJWX | EST aaacjwx (UK-HGMP) | | 0 | 0 |
| 230 | 15658 | 1 | 13 | H E C C R | HUMRPS6A | Ribosomal protein S6 | | 767 | 0 |
| 231 | 15683 | 1 | 13 | H E C E B | HUMLCTHB | Clathrin, light chain-B | | 239 | 0 |
| 232 | 15688 | 1 | 13 | H O C M Z | BOVATPS | V | ATP synthase gamma subunit | 2117 | 0 |
| 233 | 15753 | 1 | 13 | H E P E B | HUMCAM1V | Adhesion molecule VCAM1, vascular cell | | 160 | 0 |
| 234 | 15771 | 1 | 13 | H E P E B | HUMLB2A26 | Laminin B2 chain | | 0 | 0 |
| 235 | 15839 | 1 | 13 | H E U U S | S94424 | Cell adhesion regulator; CAR | | 428 | 0 |
| 236 | 15853 | 1 | 13 | H O C C R | RNRPL28 | R | Ribosomal protein L28 | 407 | 0 |
| 237 | 15954 | 1 | 13 | H E P Z B | HSHPCP | Serglycin; sec granule proteoglycan cor | | 463 | 0 |
| 238 | 15980 | 1 | 13 | H E C C Q | HUMBHAB | N-acetyl-beta-glucosaminidase | | 1009 | 0 |
| 239 | 16123 | 1 | 13 | H I U U U | NCY015583 | INCYTE clone 015583 | | 0 | 0 |
| 240 | 16136 | 1 | 13 | H X U U U | M78527 | EST 00675 (IGR) | | 0 | 0 |
| 241 | 16170 | 1 | 13 | H E P E B | HUMHLAC | Human Leukocyte Antigen-C, class I | | 235 | 0 |
| 242 | 16222 | 1 | 13 | H E C U Y | HUMCSISA | Oncogene cis | | 0 | 0 |
| 243 | 16241 | 1 | 13 | H E C C E | HUMSAMS | S-adenosylmethionine synthetase | | 1455 | 0 |
| 244 | 16299 | 1 | 13 | H O P E B | RATADRB | R | Adrenergic receptor; BTF protein | −774 | 0 |
| 245 | 16421 | 1 | 13 | H X U U U | M78858 | EST 01006 (IGR) | | 0 | 0 |
| 246 | 16425 | 1 | 13 | H E U U H | HSDINFIG | Interferon inducible protein | | −128 | 0 |
| 247 | 16498 | 1 | 13 | H E U C G | HUMRASAC | Oncogene ras-like protein | | 433 | 2 |
| 248 | 16542 | 1 | 13 | H X U U U | HSAFICO82 | EST FIc082 (Genethon) | | 0 | 0 |
| 249 | 16595 | 1 | 13 | H O P Z B | CFGPCR1 | D | G protein-coupled receptor | −314 | 1 |
| 250 | 16613 | 1 | 13 | H E C C N | HUMHPRTB | Hypoxanthine P-ribosyltransferase | | 0 | 0 |
| 251 | 16622 | 1 | 13 | H X U U U | T03027 | EST FB20G3 (Sikela) | | 0 | 0 |
| 252 | 16636 | 1 | 13 | H E P U Q | HUMSA | co-beta glucosidase, sulfatide activat | | −478 | 0 |
| 253 | 16639 | 1 | 13 | H E C C U | HUMHLGP85 | Lysosomal sialoglycoprotein | | 1198 | 0 |
| 254 | 16669 | 1 | 13 | H E C C T | HUM4AI | initiation factor 4AI | | 387 | 0 |
| 255 | 16884 | 1 | 13 | H E C E Q | HUMGLBA | co-beta glucosidase | | −502 | 0 |
| 256 | 16892 | 1 | 13 | H O C E E | BOVIOPPP | V | Inorganic pyrophosphatase | 0 | 1 |
| 257 | 16897 | 1 | 13 | H E U U U | HSVIMENT | Vimentin; intermediate filament ptn | | 31 | 0 |
| 258 | 16974 | 1 | 13 | H E C C R | HUMRPS14 | Ribosomal protein S14 | | 3437 | 0 |
| 259 | 16983 | 1 | 13 | H E C U U | HUMGRP78 | Glucose-regulated protein, 78 kDa | | 2213 | 0 |
| 260 | 16988 | 1 | 13 | H E U U U | HUMEMS | Amplaxin, EMS1 gene | | 487 | 0 |

TABLE 2-continued

| | | | | | | | | | |
|---|---|---|---|---|---|---|---|---|---|
| 261 | 17019 | 1 | 13 | H E C C R | | HUMRGM | Ribosomal RNA, 28S | 3695 | 0 |
| 262 | 17151 | 1 | 13 | H X U U U | | M77972 | EST HFBCF64 | 0 | 0 |
| 263 | 17159 | 1 | 13 | H E P S P | | HUMCLI | Complement cytolysis inhibitor; apo J | 201 | 0 |
| 264 | 17175 | 1 | 13 | H O C ME | | PIGACON P | Aconitase, mitochondrial | 996 | 1 |
| 265 | 17175 | 1 | 13 | H E U U H | | HUMIFN1SK | Interferon-induced 17kD/15kD protein | 560 | 0 |
| 266 | 17184 | 1 | 13 | H E U U E | | HSDHPR | Dihydropteridine reductase | 717 | 0 |
| 267 | 17254 | 1 | 13 | H E P E B | | HUMB2M2 | Microglobulin, beta-2 | 0 | 0 |
| 268 | 17278 | 1 | 13 | H E P E | | HSCD59A | lymphocytic antigen CD59 | 268 | 0 |
| 269 | 17408 | 1 | 13 | H H U U D | ? | HSPHL1 | Oncogene myc; cytochrome c oxidase | 0 | 0 |
| 270 | 17438 | 1 | 13 | H E C C R | | HUMRPSA3A | Ribosomal protein S3a; v-fos tf effect | 706 | 0 |
| 271 | 17459 | 1 | 13 | H E | R | HSTRA1 | homologue of murine tumor rejection at | −15 | 0 |
| 272 | 17572 | 1 | 13 | H E P S S | | HUMGRANUL | Granulin | 129 | 0 |
| 273 | 17642 | 1 | 13 | H O C K K | | MMTALINR M | Talin (cytoskeletal protein) | 180 | 0 |
| 274 | 17800 | 1 | 13 | H E C N D | | HUMNSEP | Nuclease-sensitive element | −85 | 0 |
| 275 | 17871 | 1 | 13 | H E C C R | | HSRPL32 | Ribosomal protein L32 | 299 | 0 |
| 276 | 18001 | 1 | 13 | H E C U 0 | | HSRAPB1 | Rap 1B; ras-related oncogene | −88 | 0 |
| 277 | 18008 | 1 | 13 | H E P C I | | HUMFAB-PHA | Fatty acid binding protein homologue | 439 | 0 |
| 278 | 18040 | 1 | 13 | H E C E C | | HUM1P90 | Calnexin, integral membrane ptn IP90 | 143 | 0 |
| 279 | 18049 | 1 | 13 | H E P E B | | HUMENDO | Endoglin, endothelial RGD-glycoprotein | 82 | 0 |
| 280 | 18214 | 1 | 13 | H E C C R | | HSRP26AA | Ribosomal protein L26 | 437 | 0 |
| 281 | 18217 | 1 | 13 | H X U U U | | M78700 | EST HHCMC44 (IGR) | 0 | 0 |
| 282 | 18220 | 1 | 13 | H E C N D | | HSBTF3B | BTF 3B; transcription factor | 522 | 0 |
| 283 | 18311 | 1 | 13 | H E C N D | | HUMNAP | Nucleosome assembly protein | 426 | 0 |
| 284 | 18313 | 1 | 13 | H X U U U | | HSAAABQCB | EST AAABQCB (UK-HGMP) | 0 | 0 |
| 285 | 18414 | 1 | 13 | H X U U U | | M78415 | EST HFBCB73 (Kerlavage) | 0 | 0 |
| 286 | 18446 | 1 | 13 | H E P S S | | HSCSP40 | Complement cytolysis inhibitor SP40-40 | 198 | 0 |
| 287 | 18518 | 1 | 13 | H E C C E | | HSGSTPI | Glutathione S-transferase | 633 | 0 |
| 288 | 18528 | 1 | 13 | H E C C L | | HUMUBI13 | Ubiquitin | 1777 | 0 |
| 289 | 18532 | 1 | 13 | H E C N N | | HUMAPE | Endonuclease, apurinic (APEX) | 621 | 0 |
| 290 | 18538 | 1 | 13 | H E C U U | | HUMTHD | Thioredoxin | 353 | 0 |
| 291 | 18542 | 1 | 13 | H E P U H | ? | HUMIEF | Transformation-sens ptn IEF-SSP-3521 | 534 | 0 |
| 292 | 18630 | 1 | 13 | H E C C Z | | HUMATPC | ADP/ATP carrier ptn | 400 | 0 |
| 293 | 18699 | 1 | 13 | H E C U D | | HSRD | RD protein, RNA-binding, MHC class III | 481 | 0 |
| 294 | 18812 | 1 | 13 | H X U U U | | M85505 | EST HFBCJ11 (Kerlavage) | 0 | 0 |
| 295 | 18899 | 1 | 13 | H E P E B | ? | HUMMUC18B | Glycoprotein MUC18; adhesion molecule | −596 | 0 |
| 296 | 18927 | 1 | 13 | H E U U H | | HUMIFI16A | Interferon-gamma induced protein | −16 | 0 |
| 297 | 18985 | 1 | 13 | H E P C I | | HUMCYCLO | Cyclophillin | 337 | 0 |
| 298 | 19003 | 1 | 13 | H X U U U | | HSB20H022 | EST 20H02 (Genethon) | 0 | 0 |
| 299 | 19007 | 1 | 13 | H E C C R | | HUMRPS17 | Ribosomal protein S17 | 287 | 0 |
| 300 | 19088 | 1 | 13 | H E C C R | | HUMPPARP1 | Acidic ribosomal phosphoprotein P1 | 452 | 0 |
| 301 | 19145 | 1 | 13 | H O U C Y | | RATERK3 R | Kinase, extracellular signal-related | 0 | 0 |
| 302 | 19152 | 1 | 13 | H X C C R | | M78040 | EST HHCMG86; ribosomal ptn L1a | 0 | 0 |
| 303 | 19188 | 1 | 13 | H E P E B | | HUMM-HBA123 | HLA protein, chicken B complex homolog | 1006 | 0 |
| 304 | 19195 | 1 | 13 | H E C U H | | HUMHSP90 | Heat shock protein, 90-kDa | 916 | 0 |
| 305 | 19440 | 1 | 13 | H E P S E | | HUMCN2 | Collagenase, skin | 1224 | 0 |
| 306 | 19459 | 1 | 13 | H E | | HUMGAPDR | Glyceraldehyde-3-phosphate dehydrogena | 760 | 0 |
| 307 | 19520 | 1 | 13 | H X U U U | R | HSAFIF047 | EST FIf047 (Genexpress) | 0 | 0 |
| 308 | 19542 | 1 | 13 | H X U U U | | HSAAABIRO | EST AAABIRO (UK-HGMP) | 0 | 0 |
| 309 | 19614 | 1 | 13 | H E C C R | | HUMPPARP0 | Acidic ribosomal phosphoprotein P0 | 733 | 0 |
| 310 | 19719 | 1 | 13 | H O U C C | | MMCABIN M | Calcium-binding protein | 337 | 1 |
| 311 | 19731 | 1 | 13 | H O U U U | | MMI3RNA M | I3 gene; specific expression pattern | 165 | 1 |
| 312 | 19738 | 1 | 13 | H I U U U | | NCY018313 | INCYTE clone 018313 | 0 | 0 |
| 313 | 19811 | 1 | 13 | H O C MZ | | BTNADH-DUA V | NADH dehydrogenase; ubiquinone | 309 | 0 |
| 314 | 19813 | 1 | 13 | H X U U U | | H5B07A082 | EST 07A08 (Genexpress) | 0 | 0 |
| 315 | 19834 | 1 | 13 | H E C C R | | HUMRPL7A | Ribosomal protein L7A; PLA-X; surf3 | 422 | 0 |
| 316 | 19918 | 1 | 13 | H H U C Y | | HUMFAK | Kinase, focal adhesion;tyrosine kinase | −45 | 0 |
| 317 | 19953 | 1 | 13 | H E U C G | | HSGIR | G (i) protein alpha-subunit | −37 | 0 |
| 318 | 19955 | 1 | 13 | H E U U U | | HSLLREP3 | LLrep3; repetitive DNA | 530 | 0 |
| 319 | 19963 | 1 | 13 | H E P S S | | HUMVMFM | Von Willebrand factor, glycoprotein | 1008 | 0˜˜Z |

TABLE 3

NORMAL MONOCYTE VERSUS
ACTIVATED MACROPHAGE
Top 15 Most Abundant Genes

| Normal | Activated |
|---|---|
| 1 Elongation factor-1 alpha | Interleukin-1 beta |
| 2 Ribosomal phosphoprotein | Macrophage inflammatory protein-1 |
| 3 Ribosomal protein S8 homolog | Interleukin-8 |
| 4 Beta-Globin | Lymphocyte activation gene |
| 5 Ferritin H chain | Elongation factor-1 alpha |
| 6 Ribosomal protein L7 | Beta actin |

TABLE 3-continued

NORMAL MONOCYTE VERSUS ACTIVATED MACROPHAGE
Top 15 Most Abundant Genes

| Normal | Activated |
| --- | --- |
| 7 Nucleoplasmin | Rantes T-cell specific protein |
| 8 Ribosomal protein S20 homolqg | Poly A binding protein |
| 9 Transferrin receptor | Osteopontin; nephropontin |
| 10 Poly-A binding protein | Tumor Necrosis Factor-alpha |
| 11 Translationally controlled tumor ptn | INCYTE clone 011050 |
| 12 Ribosomal protein S25 | Cu/Zn superoxide dismutase |
| 13 Signal recognition particle SRP9 | Adenylate cyclase (yeast homolog) |
| 14 Histone H2A.Z | NGF-related B cell activation molecule |
| 15 Ribosomal protein Ke-3 | Protease Nexin-1, glial-derived |

TABLE 4

MONOCYTE VERSUS ACTIVATED MACROPHAGE: ELECTRONIC SUBTRACTION
Top 15 Activated cDNAs

| Activated cDNA | Fold Activation |
| --- | --- |
| 1 Interleukin-1 beta | 131 |
| 2 Macrophage inflammatory protein-1 | 121 |
| 3 Interleukin-8 | 119 |
| 4 Lymphocyte activation gene | 71 |
| 5 Rantes T-cell specific protein | 23 |
| 6 Osteopontin; nephropontin | 20 |
| 7 INCYTE clone 011050 | 17 |
| 8 Tumor Necrosis Factor-alpha | 17 |
| 9 Cu/Zn superoxide dismutase | 14 |
| 10 NGF-related B cell activation molecule | 10 |
| 11 Immediate early response PMA-ind gene | 9 |
| 12 Protease Nexin-1, glial-derived | 9 |
| 13 Incyte clone 011353 | 8 |
| 14 Incyte clone 010298 | 7 |
| 15 Incyte clone 011138 | 7 |

TABLE 5

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
| --- | --- | --- | --- | --- | --- | --- | --- | --- | --- | --- | --- |
| 10022 | E | P | S | S | HUMIL1 | | Interleukin 1-beta | 0 | 131 | 262.00 | 0 |
| 10036 | E | P | S | S | HSMDNCF | | Interleukin-8; neutrophil activat ptn | 0 | 119 | 238.00 | 0 |
| 10089 | E | P | S | S | HSLAG1CDN | | Lymphocyte activation gene LAG1; Act-2 | 0 | 71 | 142.00 | 0 |
| 10060 | E | P | S | S | HUMTCSM | | T-cell specific chemokine RANTES | 0 | 23 | 46.000 | 0 |
| 10003 | E | P | S | S | HUMMIP1A | | Macrophage inflammatory protein-1 | 3 | 121 | 40.333 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
|---|---|---|---|---|---|---|---|---|---|---|---|
| 10689 | E | P | C | C | HSOP | | Osteopontin; nephropontin | 0 | 20 | 40.000 | 0 |
| 11050 | I | U | U | U | NCY011050 | | INCYTE clone 011050 | 0 | 17 | 34.000 | 0 |
| 10937 | E | P | S | S | HSTNFR | | TNF-alpha | 0 | 17 | 34.000 | 0 |
| 10176 | E | P | C | E | HSSOD | | Superoxide dismutase, Cu/Zn | 0 | 14 | 28.000 | 0 |
| 10886 | E | P | E | B | HSCDW40 | | B-cell activation molecule, NGF-relate | 0 | 10 | 20.000 | 0 |
| 10186 | E | P | U | H | HUMAPR | | Immediate early response PMA-ind gene | 0 | 9 | 18.000 | 0 |
| 10967 | E | P | S | P | HUMGDN | | Protease nexin-1, glial-derived | 0 | 9 | 18.000 | 0 |
| 11353 | I | U | U | U | NCY011353 | | INCYTE clone 011353 | 0 | 8 | 16.000 | 0 |
| 10298 | I | U | U | U | NCY010298 | | INCYTE clone 010298 | 0 | 7 | 14.000 | 0 |
| 10215 | E | P | S | P | HUM4COLA | | Collagenase, type IV | 0 | 6 | 12.000 | 0 |
| 10276 | I | U | U | U | NCY010276 | | INCYTE clone 010276 | 0 | 6 | 12.000 | 0 |
| 10488 | I | U | U | U | NCY010488 | | INCYTE clone 010488 | 0 | 6 | 12.000 | 0 |
| 11138 | I | U | U | U | NCY011138 | | INCYTE clone 011138 | 0 | 6 | 12.000 | 2 |
| 10037 | E | P | C | E | HUMCAPPRO | | Adenylate cyclase-assoc ptn (CAP) | 1 | 10 | 10.000 | 0 |
| 10840 | E | C | C | E | HUMADCY | | Adenylyl cyclase-assoc protein | 0 | 5 | 10.000 | 0 |
| 10672 | E | P | E | B | HSCD44E | | Cell adhesion glycoprotein CD44 | 0 | 5 | 10.000 | 0 |
| 12837 | E | P | C | W | HUMCYCLOX | | Cyclooxygenase-2 | 0 | 5 | 10.000 | 0 |
| 10001 | I | U | U | U | NCY010001 | | INCYTE clone 010001 | 0 | 5 | 10.000 | 0 |
| 10005 | I | U | U | U | NCY010005 | | INCYTE clone 010005 | 0 | 5 | 10.000 | 0 |
| 10294 | I | U | U | U | NCY010294 | | INCYTE clone 010294 | 0 | 5 | 10.000 | 0 |
| 10297 | I | U | U | U | NCY010297 | | INCYTE clone 010297 | 0 | 5 | 10.000 | 0 |
| 10403 | I | U | U | U | NCY010403 | | INCYTE clone 010403 | 0 | 5 | 10.000 | 0 |
| 10699 | I | U | U | U | NCY010699 | | INCYTE clone 010699 | 0 | 5 | 10.000 | 0 |
| 10966 | I | U | U | U | NCY010966 | | INCYTE clone 010966 | 0 | 5 | 10.000 | 0 |
| 12092 | I | U | U | U | NCY012092 | | INCYTE clone 012092 | 0 | 5 | 10.000 | 0 |
| 12549 | E | C | N | O | HSRHOB | | Oncogene rho | 0 | 5 | 10.000 | 0 |
| 10691 | E | C | C | E | HUMARF1BA | | ADP-ribosylation factor 1 (ARF1) | 0 | 4 | 8.000 | 0 |
| 12106 | E | C | C | E | HSADSS | | Adenylosuccinate synthetase | 0 | 4 | 8.000 | 0 |
| 10194 | E | P | S | P | HSCATHL | | Cathepsin L (Major Excreted Protein) | 0 | 4 | 8.000 | 0 |
| 10479 | O | C | C | S | CLMCYCA | I | Cyclin A (cell cycle inducer) | 0 | 4 | 8.000 | 1 |
| 10031 | I | U | U | U | NCY010031 | | INCYTE clone 010031 | 0 | 4 | 8.000 | 0 |
| 10203 | I | U | U | U | NCY010203 | | INCYTE clone 010203 | 0 | 4 | 8.000 | 0 |
| 10288 | I | U | U | U | NCY010288 | | INCYTE clone 010288 | 0 | 4 | 8.000 | 0 |
| 10372 | I | U | U | U | NCY010372 | | INCYTE clone 010372 | 0 | 4 | 8.000 | 0 |
| 10471 | I | U | U | U | NCY010471 | | INCYTE clone 010471 | 0 | 4 | 8.000 | 0 |
| 10484 | I | U | U | U | NCY010484 | | INCYTE clone 010484 | 0 | 4 | 8.000 | 0 |
| 10859 | I | U | U | U | NCY010859 | | INCYTE clone 010859 | 0 | 4 | 8.000 | 0 |
| 10890 | I | U | U | U | NCY010890 | | INCYTE clone 010890 | 0 | 4 | 8.000 | 0 |
| 11511 | I | U | U | U | NCY011511 | | INCYTE clone 011511 | 0 | 4 | 8.000 | 0 |
| 11868 | I | U | U | U | NCY011868 | | INCYTE clone 011868 | 0 | 4 | 8.000 | 0 |
| 12820 | I | U | U | U | NCY012820 | | INCYTE clone 012820 | 0 | 4 | 8.000 | 0 |
| 10133 | E | P | S | S | HSI1RAP | | Interleukin-1 antagonist, IRAP | 0 | 4 | 8.000 | 0 |
| 10516 | E | P | C | Y | HUMP2A | | Phosphatase, regulatory subunit 2A | 0 | 4 | 8.000 | 0 |
| 11063 | E | P | U | H | HUMB94 | | TNF-inducible primary response gene | 0 | 4 | 8.000 | 0 |
| 11140 | E | P | E | B | HSHB15RNA | | HB15 gene; new Ig superfamily member | 0 | 3 | 6.000 | 0 |
| 10788 | I | U | U | U | NCY001713 | | INCYTE clone 001713 | 0 | 3 | 6.000 | 0 |
| 10033 | I | U | U | U | NCY010033 | | INCYTE clone 010033 | 0 | 3 | 6.000 | 0 |
| 10035 | I | U | U | U | NCY010035 | | INCYTE clone 010035 | 0 | 3 | 6.000 | 0 |
| 10084 | I | U | U | U | NCY010084 | | INCYTE clone 010084 | 0 | 3 | 6.000 | 0 |
| 10236 | I | U | U | U | NCY010236 | | INCYTE clone 010236 | 0 | 3 | 6.000 | 0 |
| 10383 | I | U | U | U | NCY010383 | | INCYTE clone 010383 | 0 | 3 | 6.000 | 0 |
| 10450 | I | U | U | U | NCY010450 | | INCYTE clone 010450 | 0 | 3 | 6.000 | 0 |
| 10470 | I | U | U | U | NCY010470 | | INCYTE clone 010470 | 0 | 3 | 6.000 | 0 |
| 10504 | I | U | U | U | NCY010504 | | INCYTE clone 010504 | 0 | 3 | 6.000 | 0 |
| 10507 | I | U | U | U | NCY010507 | | INCYTE clone 010507 | 0 | 3 | 6.000 | 0 |
| 10598 | I | U | U | U | NCY010598 | | INCYTE clone 010598 | 0 | 3 | 6.000 | 0 |
| 10779 | I | U | U | U | NCY010779 | | INCYTE clone 010779 | 0 | 3 | 6.000 | 0 |
| 10909 | I | U | U | U | NCY010909 | | INCYTE clone 010909 | 0 | 3 | 6.000 | 0 |
| 10976 | I | U | U | U | NCY010976 | | INCYTE clone 010976 | 0 | 3 | 6.000 | 0 |
| 10985 | I | U | U | U | NCY010985 | | INCYTE clone 010985 | 0 | 3 | 6.000 | 0 |
| 11052 | I | U | U | U | NCY011052 | | INCYTE clone 011052 | 0 | 3 | 6.000 | 0 |
| 11068 | I | U | U | U | NCY011068 | | INCYTE clone 011068 | 0 | 3 | 6.000 | 0 |
| 11134 | I | U | U | U | NCY011134 | | INCYTE clone 011134 | 0 | 3 | 6.000 | 0 |
| 11136 | I | U | U | U | NCY011136 | | INCYTE clone 011136 | 0 | 3 | 6.000 | 0 |
| 11191 | I | U | U | U | NCY011191 | | INCYTE clone 011191 | 0 | 3 | 6.000 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
|---|---|---|---|---|---|---|---|---|---|---|---|
| 11219 | I | U | U | U | NCY011219 | | INCYTE clone 011219 | 0 | 3 | 6.000 | 0 |
| 11386 | I | U | U | U | NCY011386 | | INCYTE clone 011386 | 0 | 3 | 6.000 | 0 |
| 11403 | I | U | U | U | NCY011403 | | INCYTE clone 011403 | 0 | 3 | 6.000 | 0 |
| 11460 | I | U | U | U | NCY011460 | | INCYTE clone 011460 | 0 | 3 | 6.000 | 0 |
| 11618 | I | U | U | U | NCY011618 | | INCYTE clone 011618 | 0 | 3 | 6.000 | 0 |
| 11686 | I | U | U | U | NCY011686 | | INCYTE clone 011686 | 0 | 3 | 6.000 | 0 |
| 12021 | I | U | U | U | NCY012021 | | INCYTE clone 012021 | 0 | 3 | 6.000 | 0 |
| 12025 | I | U | U | U | NCY012025 | | INCYTE clone 012025 | 0 | 3 | 6.000 | 0 |
| 12320 | I | U | U | U | NCY012320 | | INCYTE clone 012320 | 0 | 3 | 6.000 | 0 |
| 12330 | I | U | U | U | NCY012330 | | INCYTE clone 012330 | 0 | 3 | 6.000 | 0 |
| 12853 | I | U | U | U | NCY012853 | | INCYTE clone 012853 | 0 | 3 | 6.000 | 0 |
| 14386 | I | U | U | U | NCY014386 | | INCYTE clone 014386 | 0 | 3 | 6.000 | 0 |
| 14391 | I | U | U | U | NCY014391 | | INCYTE clone 014391 | 0 | 3 | 6.000 | 0 |
| 14795 | I | U | U | U | NCY014795 | | INCYTE clone 014795 | 0 | 3 | 6.000 | 0 |
| 11165 | E | P | C | C | HUMLIC | | Lipocortin II | 0 | 3 | 6.000 | 0 |
| 12006 | O | P | S | P | CHKHIMP3A | C | Metalloproteinase inhibitor TIMP-3 | 0 | 3 | 6.000 | 4 |
| 13363 | E | P | U | A | HUMMGC24 | | Mucin, gastric carcinoma epithelial | 0 | 3 | 6.000 | 0 |
| 11112 | O | C | C | Q | DOGOST48A | D | Oligosaccharyltransferase, 48 kDa | 0 | 3 | 6.000 | 3 |
| 10847 | E | P | U | D | HSETS23 | | Oncogene ETS2 | 0 | 3 | 6.000 | 0 |
| 11426 | E | C | U | O | HSRAB2 | | Oncogene rab-2; ras, YPT1-related ptn | 0 | 3 | 6.000 | 0 |
| 10153 | E | U | U | U | HSPM5 | | PM5 (collagenase homolog?) | 0 | 3 | 6.000 | 0 |
| 12083 | E | C | K | K | HSPGSR | | Plasma gelsolin | 0 | 3 | 6.000 | 0 |
| 11330 | H | P | U | U | HUM22SM | | Smooth muscle senescent ptn, 22 kDa | 0 | 3 | 6.000 | 3 |
| 12630 | E | P | S | S | HSTNFABX | | TNF a/b gene (noncoding) | 0 | 3 | 6.000 | 0 |
| 13104 | E | P | N | D | HUMISGF3A | | Transcription factor ISGF-3 | 0 | 3 | 6.000 | 0 |
| 11312 | E | P | E | B | HSUPARAA | | Urokinase plasminogen act surf receptg | 0 | 3 | 6.000 | 0 |
| 10513 | E | P | E | B | HUMVDAC1X | | Voltage-dep anion channel, isoform 1 | 0 | 3 | 6.000 | 0 |
| 10503 | E | U | N | D | HUMHXBP1 | | X box binding protein XBP-1 | 0 | 3 | 6.000 | 0 |
| 10199 | E | C | C | F | HUMFERL | | Ferritin, light chain | 3 | 13 | 4.333 | 0 |
| 10653 | E | P | S | P | HSTIMPR | | Metalloproteinase inhibitor TIMP-1 | 1 | 4 | 4.000 | 0 |
| 14741 | E | C | E | C | HUMHO2A | | ATPase calcium pump | 0 | 2 | 4.000 | 0 |
| 13018 | E | C | U | Z | HUMPMPCA | | ATPase, calcium pumping | 0 | 2 | 4.000 | 0 |
| 13326 | E | C | C | G | HSGSA1R | | Adenyl cyclase coupling ptn G(s)-A-S1 | 0 | 2 | 4.000 | 1 |
| 11869 | E | P | S | P | HSAMPEPN | | Aminopeptidase N, intestinal; CD13 | 0 | 2 | 4.000 | 0 |
| 10477 | E | P | S | P | HUMCATS | | Cathepsin S, elastinolytic Cys proteas | 0 | 2 | 4.000 | 0 |
| 14888 | O | S | E | K | RATCARHC | R | Clathrin, heavy chain | 0 | 2 | 4.000 | 0 |
| 11577 | E | C | Z | L | HSDOCKP | | Docking protein, signal recognition | 0 | 2 | 4.000 | 0 |
| 12893 | O | C | C | Q | CRUACAPT | S | GlcNac-1-PO4 transferase | 0 | 2 | 4.000 | 3 |
| 10826 | E | C | N | D | HSHMGY | | High mobility group protein; Y/I | 0 | 2 | 4.000 | 0 |
| 10798 | E | P | N | T | HUMSRP20 | | HnRNA splicing factor 20 (SRp20) | 0 | 2 | 4.000 | 0 |
| 12347 | I | U | U | U | NCY000942 | | INCYTE clone 000942 | 0 | 2 | 4.000 | 0 |
| 11317 | I | U | U | U | NCY001367 | | INCYTE clone 001367 | 0 | 2 | 4.000 | 0 |
| 10013 | I | U | U | U | NCY010013 | | INCYTE clone 010013 | 0 | 2 | 4.000 | 0 |
| 10018 | I | U | U | U | NCY010018 | | INCYTE clone 010018 | 0 | 2 | 4.000 | 0 |
| 10086 | I | U | U | U | NCY010086 | | INCYTE clone 010086 | 0 | 2 | 4.000 | 0 |
| 10092 | I | U | U | U | NCY010092 | | INCYTE clone 010092 | 0 | 2 | 4.000 | 0 |
| 10137 | I | U | U | U | NCY010137 | | INCYTE clone 010137 | 0 | 2 | 4.000 | 0 |
| 10213 | I | U | U | U | NCY010213 | | INCYTE clone 010213 | 0 | 2 | 4.000 | 0 |
| 10214 | I | U | U | U | NCY010214 | | INCYTE clone 010214 | 0 | 2 | 4.000 | 0 |
| 10285 | I | U | U | U | NCY010285 | | INCYTE clone 010285 | 0 | 2 | 4.000 | 0 |
| 10290 | I | U | U | U | NCY010290 | | INCYTE clone 010290 | 0 | 2 | 4.000 | 0 |
| 10291 | I | U | U | U | NCY010291 | | INCYTE clone 010291 | 0 | 2 | 4.000 | 0 |
| 10386 | I | U | U | U | NCY010386 | | INCYTE clone 010386 | 0 | 2 | 4.000 | 0 |
| 10410 | I | U | U | U | NCY010410 | | INCYTE clone 010410 | 0 | 2 | 4.000 | 0 |
| 10419 | I | U | U | U | NCY010419 | | INCYTE clone 010419 | 0 | 2 | 4.000 | 0 |
| 10459 | I | U | U | U | NCY010459 | | INCYTE clone 010459 | 0 | 2 | 4.000 | 0 |
| 10469 | I | U | U | U | NCY010469 | | INCYTE clone 010469 | 0 | 2 | 4.000 | 0 |
| 10621 | I | U | U | U | NCY010621 | | INCYTE clone 010621 | 0 | 2 | 4.000 | 0 |
| 10649 | I | U | U | U | NCY010649 | | INCYTE clone 010649 | 0 | 2 | 4.000 | 0 |
| 10863 | I | U | U | U | NCY010863 | | INCYTE clone 010863 | 0 | 2 | 4.000 | 0 |
| 10907 | I | U | U | U | NCY010907 | | INCYTE clone 010907 | 0 | 2 | 4.000 | 0 |
| 10914 | I | U | U | U | NCY010914 | | INCYTE clone 010914 | 0 | 2 | 4.000 | 0 |
| 10936 | I | U | U | U | NCY010936 | | INCYTE clone 010936 | 0 | 2 | 4.000 | 0 |
| 10982 | I | U | U | U | NCY010982 | | INCYTE clone 010982 | 0 | 2 | 4.000 | 0 |
| 11032 | I | U | U | U | NCY011032 | | INCYTE clone 011032 | 0 | 2 | 4.000 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
|---|---|---|---|---|---|---|---|---|---|---|---|
| 11041 | I | U | U | U | NCY011041 | | INCYTE clone 011041 | 0 | 2 | 4.000 | 0 |
| 11045 | I | U | U | U | NCY011045 | | INCYTE clone 011045 | 0 | 2 | 4.000 | 0 |
| 11048 | I | U | U | U | NCY011048 | | INCYTE clone 011048 | 0 | 2 | 4.000 | 0 |
| 11055 | I | U | U | U | NCY011055 | | INCYTE clone 011055 | 0 | 2 | 4.000 | 0 |
| 11059 | I | U | U | U | NCY011059 | | INCYTE clone 011059 | 0 | 2 | 4.000 | 0 |
| 11129 | I | U | U | U | NCY011129 | | INCYTE clone 011129 | 0 | 2 | 4.000 | 0 |
| 11148 | I | U | U | U | NCY011148 | | INCYTE clone 011148 | 0 | 2 | 4.000 | 0 |
| 11260 | I | U | U | U | NCY011260 | | INCYTE clone 011260 | 0 | 2 | 4.000 | 0 |
| 11316 | I | U | U | U | NCY011316 | | INCYTE clone 011316 | 0 | 2 | 4.000 | 0 |
| 11375 | I | U | U | U | NCY011375 | | INCYTE clone 011375 | 0 | 2 | 4.000 | 0 |
| 11383 | I | U | U | U | NCY011383 | | INCYTE clone 011383 | 0 | 2 | 4.000 | 0 |
| 11388 | I | U | U | U | NCY011388 | | INCYTE clone 011388 | 0 | 2 | 4.000 | 0 |
| 11390 | I | U | U | U | NCY011390 | | INCYTE clone 011390 | 0 | 2 | 4.000 | 0 |
| 11436 | I | U | U | U | NCY011436 | | INCYTE clone 011436 | 0 | 2 | 4.000 | 0 |
| 11483 | I | U | U | U | NCY011483 | | INCYTE clone 011483 | 0 | 2 | 4.000 | 0 |
| 11519 | I | U | U | U | NCY011519 | | INCYTE clone 011519 | 0 | 2 | 4.000 | 0 |
| 11520 | I | U | U | U | NCY011520 | | INCYTE clone 011520 | 0 | 2 | 4.000 | 0 |
| 11556 | I | U | U | U | NCY011556 | | INCYTE clone 011556 | 0 | 2 | 4.000 | 0 |
| 11614 | I | U | U | U | NCY011614 | | INCYTE clone 011614 | 0 | 2 | 4.000 | 0 |
| 11629 | I | U | U | U | NCY011629 | | INCYTE clone 011629 | 0 | 2 | 4.000 | 0 |
| 11695 | I | U | U | U | NCY011695 | | INCYTE clone 011695 | 0 | 2 | 4.000 | 0 |
| 11744 | I | U | U | U | NCY011744 | | INCYTE clone 011744 | 0 | 2 | 4.000 | 0 |
| 11777 | I | U | U | U | NCY011777 | | INCYTE clone 011777 | 0 | 2 | 4.000 | 0 |
| 11848 | I | U | U | U | NCY011848 | | INCYTE clone 011848 | 0 | 2 | 4.000 | 0 |
| 12058 | I | U | U | U | NCY012058 | | INCYTE clone 012058 | 0 | 2 | 4.000 | 0 |
| 12072 | I | U | U | U | NCY012072 | | INCYTE clone 012072 | 0 | 2 | 4.000 | 0 |
| 12420 | I | U | U | U | NCY012420 | | INCYTE clone 012420 | 0 | 2 | 4.000 | 0 |
| 12466 | I | U | U | U | NCY012466 | | INCYTE clone 012466 | 0 | 2 | 4.000 | 0 |
| 12548 | I | U | U | U | NCY012548 | | INCYTE clone 012548 | 0 | 2 | 4.000 | 0 |
| 12802 | I | U | U | U | NCY012802 | | INCYTE clone 012802 | 0 | 2 | 4.000 | 0 |
| 12803 | I | U | U | U | NCY012803 | | INCYTE clone 012803 | 0 | 2 | 4.000 | 0 |
| 12813 | I | U | U | U | NCY012813 | | INCYTE clone 012813 | 0 | 2 | 4.000 | 0 |
| 12824 | I | U | U | U | NCY012824 | | INCYTE clone 012824 | 0 | 2 | 4.000 | 0 |
| 12881 | I | U | U | U | NCY012881 | | INCYTE clone 012881 | 0 | 2 | 4.000 | 0 |
| 12902 | I | U | U | U | NCY012902 | | INCYTE clone 012902 | 0 | 2 | 4.000 | 0 |
| 12960 | I | U | U | U | NCY012960 | | INCYTE clone 012960 | 0 | 2 | 4.000 | 0 |
| 13027 | I | U | U | U | NCY013027 | | INCYTE clone 013027 | 0 | 2 | 4.000 | 0 |
| 13120 | I | U | U | U | NCY013120 | | INCYTE clone 013120 | 0 | 2 | 4.000 | 0 |
| 13156 | I | U | U | U | NCY013156 | | INCYTE clone 013156 | 0 | 2 | 4.000 | 0 |
| 13165 | I | U | U | U | NCY013165 | | INCYTE clone 013165 | 0 | 2 | 4.000 | 0 |
| 13174 | I | U | U | U | NCY013174 | | INCYTE clone 013174 | 0 | 2 | 4.000 | 0 |
| 13284 | I | U | U | U | NCY013284 | | INCYTE clone 013284 | 0 | 2 | 4.000 | 0 |
| 13517 | I | U | U | U | NCY013517 | | INCYTE clone 013517 | 0 | 2 | 4.000 | 0 |
| 13567 | I | U | U | U | NCY013567 | | INCYTE clone 013567 | 0 | 2 | 4.000 | 0 |
| 13690 | I | U | U | U | NCY013690 | | INCYTE clone 013690 | 0 | 2 | 4.000 | 0 |
| 13899 | I | U | U | U | NCY013899 | | INCYTE clone 013899 | 0 | 2 | 4.000 | 0 |
| 13903 | I | U | U | U | NCY013903 | | INCYTE clone 013903 | 0 | 2 | 4.000 | 0 |
| 14057 | I | U | U | U | NCY014057 | | INCYTE clone 014057 | 0 | 2 | 4.000 | 0 |
| 14130 | I | U | U | U | NCY014130 | | INCYTE clone 014130 | 0 | 2 | 4.000 | 0 |
| 14161 | I | U | U | U | NCY014161 | | INCYTE clone 014161 | 0 | 2 | 4.000 | 0 |
| 14179 | I | U | U | U | NCY014179 | | INCYTE clone 014179 | 0 | 2 | 4.000 | 0 |
| 14185 | I | U | U | U | NCY014185 | | INCYTE clone 014185 | 0 | 2 | 4.000 | 0 |
| 14308 | I | U | U | U | NCY014308 | | INCYTE clone 014308 | 0 | 2 | 4.000 | 0 |
| 14314 | I | U | U | U | NCY014314 | | INCYTE clone 014314 | 0 | 2 | 4.000 | 0 |
| 14542 | I | U | U | U | NCY014542 | | INCYTE clone 014542 | 0 | 2 | 4.000 | 0 |
| 14573 | I | U | U | U | NCY014573 | | INCYTE clone 014573 | 0 | 2 | 4.000 | 0 |
| 14853 | I | U | U | U | NCY014853 | | INCYTE clone 014853 | 0 | 2 | 4.000 | 0 |
| 12710 | E | P | U | H | HUMISG2 | | Interferon stimulated gene; ISG-54K | 0 | 2 | 4.000 | 0 |
| 10190 | E | P | E | B | HUMLAP | | Leukocyte adhesion ptn LFA-1/Mac-1 | 0 | 2 | 4.000 | 0 |
| 11167 | O | P | E | B | MMMACR | | Macrosialin; lamp/lpg glycoptn family | 0 | 2 | 4.000 | 3 |
| 10861 | O | P | U | U | RATNP25GN | R | Neuronal protein NP25 | 0 | 2 | 4.000 | 2 |
| 13085 | E | P | C | G | HSRHOG | | Oncogene rhoG GTPase, ras family membr | 0 | 2 | 4.000 | 0 |
| 13358 | E | P | S | P | HUMPAI2 | | Plasminogen activator inhibitor | 0 | 2 | 4.000 | 0 |
| 12858 | E | C | C | Y | HSPKA | | Protein kinase, cAMP-dependent | 0 | 2 | 4.000 | 0 |
| 13177 | O | U | C | Y | S90449 | | Protein phosphatase 2C | 0 | 2 | 4.000 | 1 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation  f = distribution  z = location  r = function  s = species  i = interest
1057 genes, for a total of 2151 clones

| number | d | f | z | r | entry | s | descriptor | bgfreq | rfend | ratio | i |
|---|---|---|---|---|---|---|---|---|---|---|---|
| 10508 | E | C | C | N | HSPNP | | Purine nucleoside phosphorylase | 0 | 2 | 4.000 | 0 |
| 11415 | O | C | C | T | DOGSEC61A | D | SEC61 homologue (rib-assoc ptn) | 0 | 2 | 4.000 | 0 |
| 11245 | E | U | N | D | M28372 | | Sterol DNA-binding protein | 0 | 2 | 4.000 | 0 |
| 11954 | E | U | U | U | HSHSP1 | | Synaptophysin related protein, H-Sp1 | 0 | 2 | 4.000 | 0 |
| 10786 | E | C | C | T | HUMWRSAA | | TRNA synthetase, tryptophanyl; IFP53 | 0 | 2 | 4.000 | 0 |
| 12042 | E | C | N | D | HUMTFIID | | Transcription factor IID; TATA bdg ptn | 0 | 2 | 4.000 | 0 |
| 11121 | E | C | C | T | HUMEIF2A | | Translational initiation factor eIF-2 | 0 | 2 | 4.000 | 0 |
| 13074 | E | P | K | K | HSTM30R | | Tropomyosin TM30, fibroblast | 0 | 2 | 4.000 | 0 |
| 10657 | E | C | K | K | HSVIMENT | | Vimentin; intermediate filament ptn | 0 | 2 | 4.000 | 0 |
| 12856 | E | P | C | X | HSPLE | | Pleckstrin (p47); pkc substrate | 2 | 7 | 3.500 | 0 |
| 10485 | E | P | E | B | HSMGLO | | Microglobulin, beta-2- | 1 | 3 | 3.000 | 0 |
| 10990 | E | P | N | D | HUMMAD3A | | Monocyte IkB-like activity, MAD-3 | 1 | 3 | 3.000 | 0 |
| 10927 | E | C | C | R | HSRPL6AA | | Ribosomal protein L6 | 1 | 3 | 3.000 | 0 |
| 11489 | E | C | C | Y | HUMLYN | | Tyrosine kinase, lyn B | 1 | 3 | 3.000 | 0 |
| 10293 | E | C | C | T | HSPOLYAB | | Binding protein, polyadenylate | 7 | 20 | 2.857 | 0 |
| 10392 | E | P | C | Q | HUMPKM2L | | Pyruvate kinase; thyroid hormone bnd pt | 3 | 7 | 2.333 | 0 |
| 12627 | E | P | C | S | HUMP65 | | Plastin,T-, phosphoprotein (65Kd) | 2 | 4 | 2.000 | 1 |
| 10438 | E | P | N | D | HUMYB1A | | Y box binding ptn-1/DNA binding ptn B | 2 | 4 | 2.000 | 0 |
| 11132 | E | C | E | Q | HUMSA | | Co-beta glucosidase | 1 | 2 | 2.000 | 0 |
| 12731 | E | P | C | E | HUMENOA | | Enolase, alpha (non-neuronal) | 1 | 2 | 2.000 | 0 |
| 10995 | E | P | C | E | HUMGLP | | Glutathione peroxidase; rhoh12 | 1 | 2 | 2.000 | 0 |
| 13521 | E | C | N | D | HSHMGI | | High mobility group-1 protein; HMG-1 | 1 | 2 | 2.000 | 0 |
| 13682 | E | C | U | U | HSRIBIIR | | Ribophorin II | 1 | 2 | 2.000 | 0 |
| 10694 | E | C | C | Z | HUMATPC | | ADP/ATP carrier ptn | 0 | 1 | 2.000 | 0 |
| 13320 | O | C | M | Z | M24103 | V | ADP/ATP translocase, mt, T1 & T2 | 0 | 1 | 2.000 | 0 |
| 13324 | E | U | U | U | HUMTRLALL1 | | ALL-1 gene (chromosome 4) | 0 | 1 | 2.000 | 0 |
| 14446 | E | C | C | N | HUMAMPD2 | | AMP deaminase isoform L | 0 | 1 | 2.000 | 0 |
| 11735 | E | C | M | Z | HSATPF1M | | ATP synthase F1, alpha subunit, mt | 0 | 1 | 2.000 | 0 |
| 13338 | E | C | C | N | HUMHK1A | | ATPase, Ca++ | 0 | 1 | 2.000 | 0 |
| 14468 | O | C | K | K | D12816 | V | Actin 2 | 0 | 1 | 2.000 | 0 |
| 13943 | E | P | U | O | HUMAML1BP | | Acute myeloid leukemia mRNA | 0 | 1 | 2.000 | 1 |
| 14590 | O | C | C | E | RATADCY3 | R | Adenylyl cyclase, type III | 0 | 1 | 2.000 | 0 |
| 10134 | E | C | C | Q | HSALDAR | | Aldolase A | 0 | 1 | 2.000 | 0 |
| 10202 | E | C | C | Q | HUMALDC | | Aldolase C | 0 | 1 | 2.000 | 0 |
| 13559 | E | C | C | Q | HSALRE | | Aldose reductase | 0 | 1 | 2.000 | 0 |
| 13817 | O | P | E | B | RNBCOP | R | B-COP, non-clathrin coated vessicle pt | 0 | 1 | 2.000 | 2 |
| 14967 | E | P | S | S | HSBSF2 | | B-cell stimulatory factor-2 | 0 | 1 | 2.000 | 0 |
| 10502 | E | P | E | B | HUMMAC2 | | B-gal binding lectin, 29 kDa; Mac-2 | 0 | 1 | 2.000 | 0 |
| 11066 | O | P | C | E | RATBRED | R | Biliverdin reductase | 0 | 1 | 2.000 | 3 |
| 13898 | E | C | C | L | HUMCBP | | Binding protein, 5'-cap | 0 | 1 | 2.000 | 0 |
| 14850 | O | U | C | C | MUSRCA1 | | Binding protein, ER-Ca | 0 | 1 | 2.000 | 0 |
| 14595 | O | P | U | U | MMF41RNA | M | Brain-specific cDNA clone F41 | 0 | 1 | 2.000 | 1 |
| 13029 | E | U | U | U | HSBCR | | Break point cluster cDNA | 0 | 1 | 2.000 | 0 |
| 12622 | E | C | C | E | HUMCAMPHOS | | CAMP phosphodiesterase | 0 | 1 | 2.000 | 0 |
| 11205 | E | U | U | U | HUMHDABCD | | CDNA match to three cosmids | 0 | 1 | 2.000 | 0 |
| 13826 | E | U | U | U | HSAAABMEZ | | CDNA of unknown function | 0 | 1 | 2.000 | 0 |
| 10139 | E | P | C | Y | HUMCSK2B | | Casein kinase II beta | 0 | 1 | 2.000 | 0 |
| 14582 | E | P | S | P | HUMCTSB | | Cathepsin B (homolog?) | 0 | 1 | 2.000 | 0 |
| 14965 | E | U | Z | U | HSCAVEOMR | | Caveolin; VIP21 transfer vessicle ptn | 0 | 1 | 2.000 | 0 |
| 14615 | E | P | E | B | HUMCD3621 | | Cell surface antigen CD36 | 0 | 1 | 2.000 | 0 |
| 14562 | E | P | E | B | HUMA15 | | Cell surface glycoptn A-15, CD63 famil | 0 | 1 | 2.000 | 0 |
| 11743 | O | C | M | Q | PIGCITSYN | P | Citrate synthase | 0 | 1 | 2.000 | 0 |
| 10028 | E | S | E | K | RATCARHC | R | Clathrin, heavy chain | 0 | 1 | 2.000 | 0 |
| 14762 | E | C | K | K | HUMCOL4A | | Collagen, type IV, alpha-1 | 0 | 1 | 2.000 | 0 |
| 13335 | E | P | S | P | HSCOLL1 | | Collagenase | 0 | 1 | 2.000 | 0 |
| 13843 | E | P | S | P | HUMOGCA | | Collagenase inhibitor | 0 | 1 | 2.000 | 0 |
| 12910 | H | P | U | U | HSFSCT | | Corticotropin; 5' flanking sequence | 0 | 1 | 2.000 | 0 |
| 11832 | E | U | U | U | HUMCRPR | | Cysteine-rich peptide | 0 | 1 | 2.000 | 0 |
| 10548 | O | U | N | D | RATCEBP | R | DNA binding protein C/EB; CCAAT bp | 0 | 1 | 2.000 | 1 |
| 12187 | E | C | M | D | HUMMTSSB | | DNA binding protein, single strand, mt | 0 | 1 | 2.000 | 0 |
| 14597 | E | P | U | U | HUMELP1A | | ERD-2-like protein, ELP-1 | 0 | 1 | 2.000 | 0 |
| 13665 | I | U | U | U | HUMXT01708 | | EST01708; 01817; 01669 (actin-like) | 0 | 1 | 2.000 | 0 |
| 14403 | E | P | S | S | HUMBCI | | Endonexin II;lipocortin V;vasc a-coag | 0 | 1 | 2.000 | 0 |
| 11439 | E | P | C | I | HUMFABPHA | | Fatty acid binding protein homologue | 0 | 1 | 2.000 | 1 |
| 11365 | E | P | E | B | HUMFCREA | | Fc receptor, epsilon, gamma chain | 0 | 1 | 2.000 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
|---|---|---|---|---|---|---|---|---|---|---|---|
| 12867 | E | P | E | B | HSFNRA | | Fibronectin receptor alpha subunit | 0 | 1 | 2.000 | 0 |
| 13885 | O | P | C | G | DOGRAB10 | D | GTP binding protein, brain-specific | 0 | 1 | 2.000 | 2 |
| 14198 | E | P | C | G | HUMRACB | | GTP binding protein, ras-related | 0 | 1 | 2.000 | 0 |
| 11189 | E | P | C | G | HSGTPCYI | | GTP cyclohydrolase I | 0 | 1 | 2.000 | 0 |
| 12742 | H | C | C | Q | HSG6PDGEN | | Glucose-6-phosphate dehydrogenase G6PD | 0 | 1 | 2.000 | 0 |
| 13992 | E | U | U | E | HUMGLY1 | | Glyoxalase I | 0 | 1 | 2.000 | 0 |
| 14618 | E | U | U | H | HSDNAJ | | Heat shock protein dnaJ, homolog | 0 | 1 | 2.000 | 0 |
| 12776 | H | C | N | D | HSHISH2B | | Histone H2B.1 | 0 | 1 | 2.000 | 0 |
| 10116 | E | P | E | B | HUMBAT2A | | Human leukocyte ag-B-assoc/transcr2 | 0 | 1 | 2.000 | 0 |
| 10034 | I | U | U | U | NCY000079 | | INCYTE clone 000079 | 0 | 1 | 2.000 | 0 |
| 14581 | I | U | U | U | NCY000216 | | INCYTE clone 000216 | 0 | 1 | 2.000 | 0 |
| 14834 | I | U | U | U | NCY000223 | | INCYTE clone 000223 | 0 | 1 | 2.000 | 0 |
| 10924 | I | U | U | U | NCY000526 | | INCYTE clone 000526 | 0 | 1 | 2.000 | 0 |
| 10678 | I | U | U | U | NCY000578 | | INCYTE clone 000578 | 0 | 1 | 2.000 | 0 |
| 14383 | I | U | U | U | NCY001102 | | INCYTE clone 001102 | 0 | 1 | 2.000 | 0 |
| 11215 | I | U | U | U | NCY001123 | | INCYTE clone 001123 | 0 | 1 | 2.000 | 0 |
| 14361 | I | U | U | U | NCY001234 | | INCYTE clone 001234 | 0 | 1 | 2.000 | 0 |
| 10004 | I | U | U | U | NCY001556 | | INCYTE clone 001556 | 0 | 1 | 2.000 | 0 |
| 10903 | I | U | U | U | NCY001668 | | INCYTE clone 001668 | 0 | 1 | 2.000 | 0 |
| 14219 | I | U | U | U | NCY002240 | | INCYTE clone 002240 | 0 | 1 | 2.000 | 0 |
| 10397 | I | U | U | U | NCY002293 | | INCYTE clone 002293 | 0 | 1 | 2.000 | 0 |
| 10370 | I | U | U | U | NCY010370 | | INCYTE clone 010370 | 0 | 1 | 2.000 | 0 |
| 10002 | N | | | | NCY010002 | | INCYTE unique clone #010002 | 0 | 1 | 2.000 | 0 |
| 10007 | N | | | | NCY010007 | | INCYTE unique clone #010007 | 0 | 1 | 2.000 | 0 |
| 10008 | N | | | | NCY010008 | | INCYTE unique clone #010008 | 0 | 1 | 2.000 | 0 |
| 10011 | N | | | | NCY010011 | | INCYTE unique clone #010011 | 0 | 1 | 2.000 | 0 |
| 10017 | N | | | | NCY010017 | | INCYTE unique clone #010017 | 0 | 1 | 2.000 | 0 |
| 10027 | N | | | | NCY010027 | | INCYTE unique clone #010027 | 0 | 1 | 2.000 | 0 |
| 10029 | N | | | | NCY010029 | | INCYTE unique clone #010029 | 0 | 1 | 2.000 | 0 |
| 10083 | N | | | | NCY010083 | | INCYTE unique clone #010083 | 0 | 1 | 2.000 | 0 |
| 10087 | N | | | | NCY010087 | | INCYTE unique clone #010087 | 0 | 1 | 2.000 | 0 |
| 10095 | N | | | | NCY010095 | | INCYTE unique clone #010095 | 0 | 1 | 2.000 | 0 |
| 10096 | N | | | | NCY010096 | | INCYTE unique clone #010096 | 0 | 1 | 2.000 | 0 |
| 10098 | N | | | | NCY010098 | | INCYTE unique clone #010098 | 0 | 1 | 2.000 | 0 |
| 10102 | N | | | | NCY010102 | | INCYTE unique clone #010102 | 0 | 1 | 2.000 | 0 |
| 10113 | N | | | | NCY010113 | | INCYTE unique clone #010113 | 0 | 1 | 2.000 | 0 |
| 10114 | N | | | | NCY010114 | | INCYTE unique clone #010114 | 0 | 1 | 2.000 | 0 |
| 10115 | N | | | | NCY010115 | | INCYTE unique clone #010115 | 0 | 1 | 2.000 | 0 |
| 10118 | N | | | | NCY010118 | | INCYTE unique clone #010118 | 0 | 1 | 2.000 | 0 |
| 10119 | N | | | | NCY010119 | | INCYTE unique clone #010119 | 0 | 1 | 2.000 | 0 |
| 10121 | N | | | | NCY010121 | | INCYTE unique clone #010121 | 0 | 1 | 2.000 | 0 |
| 10122 | N | | | | NCY010122 | | INCYTE unique clone #010122 | 0 | 1 | 2.000 | 0 |
| 10124 | N | | | | NCY010124 | | INCYTE unique clone #010124 | 0 | 1 | 2.000 | 0 |
| 10125 | N | | | | NCY010125 | | INCYTE unique clone #010125 | 0 | 1 | 2.000 | 0 |
| 10128 | N | | | | NCY010128 | | INCYTE unique clone #010128 | 0 | 1 | 2.000 | 0 |
| 10136 | N | | | | NCY010136 | | INCYTE unique clone #010136 | 0 | 1 | 2.000 | 0 |
| 10138 | N | | | | NCY010138 | | INCYTE unique clone #010138 | 0 | 1 | 2.000 | 0 |
| 10156 | N | | | | NCY010156 | | INCYTE unique clone #010156 | 0 | 1 | 2.000 | 0 |
| 10166 | N | | | | NCY010166 | | INCYTE unique clone #010166 | 0 | 1 | 2.000 | 0 |
| 10167 | N | | | | NCY010167 | | INCYTE unique clone #010167 | 0 | 1 | 2.000 | 0 |
| 10168 | N | | | | NCY010168 | | INCYTE unique clone #010168 | 0 | 1 | 2.000 | 0 |
| 10175 | N | | | | NCY010175 | | INCYTE unique clone #010175 | 0 | 1 | 2.000 | 0 |
| 10177 | N | | | | NCY010177 | | INCYTE unique clone #010177 | 0 | 1 | 2.000 | 0 |
| 10188 | N | | | | NCY010188 | | INCYTE unique clone #010188 | 0 | 1 | 2.000 | 0 |
| 10192 | N | | | | NCY010192 | | INCYTE unique clone #010192 | 0 | 1 | 2.000 | 0 |
| 10198 | N | | | | NCY010198 | | INCYTE unique clone #010198 | 0 | 1 | 2.000 | 0 |
| 10201 | N | | | | NCY010201 | | INCYTE unique clone #010201 | 0 | 1 | 2.000 | 0 |
| 10209 | N | | | | NCY010209 | | INCYTE unique clone #010209 | 0 | 1 | 2.000 | 0 |
| 10216 | N | | | | NCY010216 | | INCYTE unique clone #010216 | 0 | 1 | 2.000 | 0 |
| 10223 | N | | | | NCY010223 | | INCYTE unique clone #010223 | 0 | 1 | 2.000 | 0 |
| 10226 | N | | | | NCY010226 | | INCYTE unique clone #010226 | 0 | 1 | 2.000 | 0 |
| 10229 | N | | | | NCY010229 | | INCYTE unique clone #010229 | 0 | 1 | 2.000 | 0 |
| 10232 | N | | | | NCY010232 | | INCYTE unique clone #010232 | 0 | 1 | 2.000 | 0 |
| 10247 | N | | | | NCY010247 | | INCYTE unique clone #010247 | 0 | 1 | 2.000 | 0 |
| 10257 | N | | | | NCY010257 | | INCYTE unique clone #010257 | 0 | 1 | 2.000 | 0 |

TABLE 5-continued

```
01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones
```

| number | d | f | z | r | entry | s | descriptor | bgfreq | rfend | ratio | i |
|---|---|---|---|---|---|---|---|---|---|---|---|
| 10282 | N | | | | NCY010282 | | INCYTE unique clone #010282 | 0 | 1 | 2.000 | 0 |
| 10300 | N | | | | NCY010300 | | INCYTE unique clone #010300 | 0 | 1 | 2.000 | 0 |
| 10371 | N | | | | NCY010371 | | INCYTE unique clone #010371 | 0 | 1 | 2.000 | 0 |
| 10400 | N | | | | NCY010400 | | INCYTE unique clone #010400 | 0 | 1 | 2.000 | 0 |
| 10406 | N | | | | NCY010406 | | INCYTE unique clone #010406 | 0 | 1 | 2.000 | 0 |
| 10409 | N | | | | NCY010409 | | INCYTE unique clone #010409 | 0 | 1 | 2.000 | 0 |
| 10417 | N | | | | NCY010417 | | INCYTE unique clone #010417 | 0 | 1 | 2.000 | 0 |
| 10423 | N | | | | NCY010423 | | INCYTE unique clone #010423 | 0 | 1 | 2.000 | 0 |
| 10424 | N | | | | NCY010424 | | INCYTE unique clone #010424 | 0 | 1 | 2.000 | 0 |
| 10425 | N | | | | NCY010425 | | INCYTE unique clone #010425 | 0 | 1 | 2.000 | 0 |
| 10426 | N | | | | NCY010426 | | INCYTE unique clone #010426 | 0 | 1 | 2.000 | 0 |
| 10431 | N | | | | NCY010431 | | INCYTE unique clone #010431 | 0 | 1 | 2.000 | 0 |
| 10439 | N | | | | NCY010439 | | INCYTE unique clone #010439 | 0 | 1 | 2.000 | 0 |
| 10443 | N | | | | NCY010443 | | INCYTE unique clone #010443 | 0 | 1 | 2.000 | 0 |
| 10447 | N | | | | NCY010447 | | INCYTE unique clone #010447 | 0 | 1 | 2.000 | 0 |
| 10456 | N | | | | NCY010456 | | INCYTE unique clone #010456 | 0 | 1 | 2.000 | 0 |
| 10464 | N | | | | NCY010464 | | INCYTE unique clone #010464 | 0 | 1 | 2.000 | 0 |
| 10466 | N | | | | NCY010466 | | INCYTE unique clone #010466 | 0 | 1 | 2.000 | 0 |
| 10473 | N | | | | NCY010473 | | INCYTE unique clone #010473 | 0 | 1 | 2.000 | 0 |
| 10478 | N | | | | NCY010478 | | INCYTE unique clone #010478 | 0 | 1 | 2.000 | 0 |
| 10486 | N | | | | NCY010486 | | INCYTE unique clone #010486 | 0 | 1 | 2.000 | 0 |
| 10494 | N | | | | NCY010494 | | INCYTE unique clone #010494 | 0 | 1 | 2.000 | 0 |
| 10496 | N | | | | NCY010496 | | INCYTE unique clone #010496 | 0 | 1 | 2.000 | 0 |
| 10500 | N | | | | NCY010500 | | INCYTE unique clone #010500 | 0 | 1 | 2.000 | 0 |
| 10509 | N | | | | NCY010509 | | INCYTE unique clone #010509 | 0 | 1 | 2.000 | 0 |
| 10519 | N | | | | NCY010519 | | INCYTE unique clone #010519 | 0 | 1 | 2.000 | 0 |
| 10523 | N | | | | NCY010523 | | INCYTE unique clone #010523 | 0 | 1 | 2.000 | 0 |
| 10524 | N | | | | NCY010524 | | INCYTE unique clone #010524 | 0 | 1 | 2.000 | 0 |
| 10525 | N | | | | NCY010525 | | INCYTE unique clone #010525 | 0 | 1 | 2.000 | 0 |
| 10541 | N | | | | NCY010541 | | INCYTE unique clone #010541 | 0 | 1 | 2.000 | 0 |
| 10542 | N | | | | NCY010542 | | INCYTE unique clone #010542 | 0 | 1 | 2.000 | 0 |
| 10565 | N | | | | NCY010565 | | INCYTE unique clone #010565 | 0 | 1 | 2.000 | 0 |
| 10568 | N | | | | NCY010568 | | INCYTE unique clone #010568 | 0 | 1 | 2.000 | 0 |
| 10569 | N | | | | NCY010569 | | INCYTE unique clone #010569 | 0 | 1 | 2.000 | 0 |
| 10573 | N | | | | NCY010573 | | INCYTE unique clone #010573 | 0 | 1 | 2.000 | 0 |
| 10575 | N | | | | NCY010575 | | INCYTE unique clone #010575 | 0 | 1 | 2.000 | 0 |
| 10577 | N | | | | NCY010577 | | INCYTE unique clone #010577 | 0 | 1 | 2.000 | 0 |
| 10578 | N | | | | NCY010578 | | INCYTE unique clone #010578 | 0 | 1 | 2.000 | 0 |
| 10579 | N | | | | NCY010579 | | INCYTE unique clone #010579 | 0 | 1 | 2.000 | 0 |
| 10581 | N | | | | NCY010581 | | INCYTE unique clone #010581 | 0 | 1 | 2.000 | 0 |
| 10583 | N | | | | NCY010583 | | INCYTE unique clone #010583 | 0 | 1 | 2.000 | 0 |
| 10587 | N | | | | NCY010587 | | INCYTE unique clone #010587 | 0 | 1 | 2.000 | 0 |
| 10604 | N | | | | NCY010604 | | INCYTE unique clone #010604 | 0 | 1 | 2.000 | 0 |
| 10616 | N | | | | NCY010616 | | INCYTE unique clone #010616 | 0 | 1 | 2.000 | 0 |
| 10617 | N | | | | NCY010617 | | INCYTE unique clone #010617 | 0 | 1 | 2.000 | 0 |
| 10623 | N | | | | NCY010623 | | INCYTE unique clone #010623 | 0 | 1 | 2.000 | 0 |
| 10625 | N | | | | NCY010625 | | INCYTE unique clone #010625 | 0 | 1 | 2.000 | 0 |
| 10635 | N | | | | NCY010635 | | INCYTE unique clone #010635 | 0 | 1 | 2.000 | 0 |
| 10636 | N | | | | NCY010636 | | INCYTE unique clone #010636 | 0 | 1 | 2.000 | 0 |
| 10642 | N | | | | NCY010642 | | INCYTE unique clone #010642 | 0 | 1 | 2.000 | 0 |
| 10650 | N | | | | NCY010650 | | INCYTE unique clone #010650 | 0 | 1 | 2.000 | 0 |
| 10662 | N | | | | NCY010662 | | INCYTE unique clone #010662 | 0 | 1 | 2.000 | 0 |
| 10665 | N | | | | NCY910665 | | INCYTE unique clone #010665 | 0 | 1 | 2.000 | 0 |
| 10669 | N | | | | NCY010669 | | INCYTE unique clone #010669 | 0 | 1 | 2.000 | 0 |
| 10676 | N | | | | NCY010676 | | INCYTE unique clone #010676 | 0 | 1 | 2.000 | 0 |
| 10677 | N | | | | NCY010677 | | INCYTE unique clone #010677 | 0 | 1 | 2.000 | 0 |
| 10680 | N | | | | NCY010680 | | INCYTE unique clone #010680 | 0 | 1 | 2.000 | 0 |
| 10681 | N | | | | NCY010681 | | INCYTE unique clone #010681 | 0 | 1 | 2.000 | 0 |
| 10686 | N | | | | NCY010686 | | INCYTE unique clone #010686 | 0 | 1 | 2.000 | 0 |
| 10688 | N | | | | NCY010688 | | INCYTE unique clone #010688 | 0 | 1 | 2.000 | 0 |
| 10693 | N | | | | NCY010693 | | INCYTE unique clone #010693 | 0 | 1 | 2.000 | 0 |
| 10697 | N | | | | NCY010697 | | INCYTE unique clone #010697 | 0 | 1 | 2.000 | 0 |
| 10763 | N | | | | NCY010763 | | INCYTE unique clone #010763 | 0 | 1 | 2.000 | 0 |
| 10767 | N | | | | NCY010767 | | INCYTE unique clone #010767 | 0 | 1 | 2.000 | 0 |
| 10773 | N | | | | NCY010773 | | INCYTE unique clone #010773 | 0 | 1 | 2.000 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
|---|---|---|---|---|---|---|---|---|---|---|---|
| 10787 | N | | | | NCY010787 | | INCYTE unique clone #010787 | 0 | 1 | 2.000 | 0 |
| 10830 | N | | | | NCY010830 | | INCYTE unique clone #010830 | 0 | 1 | 2.000 | 0 |
| 10841 | N | | | | NCY010841 | | INCYTE unique clone #010841 | 0 | 1 | 2.000 | 0 |
| 10844 | N | | | | NCY010844 | | INCYTE unique clone #010844 | 0 | 1 | 2.000 | 0 |
| 10846 | N | | | | NCY010846 | | INCYTE unique clone #010846 | 0 | 1 | 2.000 | 0 |
| 10860 | N | | | | NCY010860 | | INCYTE unique clone #010860 | 0 | 1 | 2.000 | 0 |
| 10865 | N | | | | NCY010865 | | INCYTE unique clone #010865 | 0 | 1 | 2.000 | 0 |
| 10885 | N | | | | NCY010885 | | INCYTE unique clone #010885 | 0 | 1 | 2.000 | 0 |
| 10892 | N | | | | NCY010892 | | INCYTE unique clone #010892 | 0 | 1 | 2.000 | 0 |
| 10900 | N | | | | NCY010900 | | INCYTE unique clone #010900 | 0 | 1 | 2.000 | 0 |
| 10904 | N | | | | NCY010904 | | INCYTE unique clone #010904 | 0 | 1 | 2.000 | 0 |
| 10905 | N | | | | NCY010905 | | INCYTE unique clone #010905 | 0 | 1 | 2.000 | 0 |
| 10922 | N | | | | NCY010922 | | INCYTE unique clone #010922 | 0 | 1 | 2.000 | 0 |
| 10925 | N | | | | NCY010925 | | INCYTE unique clone #010925 | 0 | 1 | 2.000 | 0 |
| 10940 | N | | | | NCY010940 | | INCYTE unique clone #010940 | 0 | 1 | 2.000 | 0 |
| 10942 | N | | | | NCY010942 | | INCYTE unique clone #010942 | 0 | 1 | 2.000 | 0 |
| 10944 | N | | | | NCY010944 | | INCYTE unique clone #010944 | 0 | 1 | 2.000 | 0 |
| 10957 | N | | | | NCY010957 | | INCYTE unique clone #010957 | 0 | 1 | 2.000 | 0 |
| 10961 | N | | | | NCY010961 | | INCYTE unique clone #010961 | 0 | 1 | 2.000 | 0 |
| 10997 | N | | | | NCY010997 | | INCYTE unique clone #010997 | 0 | 1 | 2.000 | 0 |
| 11008 | N | | | | NCY011008 | | INCYTE unique clone #011008 | 0 | 1 | 2.000 | 0 |
| 11034 | N | | | | NCY011034 | | INCYTE unique clone #011034 | 0 | 1 | 2.000 | 0 |
| 11047 | N | | | | NCY011047 | | INCYTE unique clone #011047 | 0 | 1 | 2.000 | 0 |
| 11051 | N | | | | NCY011051 | | INCYTE unique clone #011051 | 0 | 1 | 2.000 | 0 |
| 11057 | N | | | | NCY011057 | | INCYTE unique clone #011057 | 0 | 1 | 2.000 | 0 |
| 11115 | N | | | | NCY011115 | | INCYTE unique clone #011115 | 0 | 1 | 2.000 | 0 |
| 11118 | N | | | | NCY011118 | | INCYTE unique clone #011118 | 0 | 1 | 2.000 | 0 |
| 11119 | N | | | | NCY011119 | | INCYTE unique clone #011119 | 0 | 1 | 2.000 | 0 |
| 11150 | N | | | | NCY011150 | | INCYTE unique clone #011150 | 0 | 1 | 2.000 | 0 |
| 11152 | N | | | | NCY011152 | | INCYTE unique clone #011152 | 0 | 1 | 2.000 | 0 |
| 11177 | N | | | | NCY011177 | | INCYTE unique clone #011177 | 0 | 1 | 2.000 | 0 |
| 11197 | N | | | | NCY011197 | | INCYTE unique clone #011197 | 0 | 1 | 2.000 | 0 |
| 11204 | N | | | | NCY011204 | | INCYTE unique clone #011204 | 0 | 1 | 2.000 | 0 |
| 11213 | N | | | | NCY011213 | | INCYTE unique clone #011213 | 0 | 1 | 2.000 | 0 |
| 11214 | N | | | | NCY011214 | | INCYTE unique clone #011214 | 0 | 1 | 2.000 | 0 |
| 11220 | N | | | | NCY011220 | | lNCYTE unique clone #011220 | 0 | 1 | 2.000 | 0 |
| 11230 | N | | | | NCY011230 | | INCYTE unique clone #011230 | 0 | 1 | 2.000 | 0 |
| 11237 | N | | | | NCY011237 | | INCYTE unique clone #011237 | 0 | 1 | 2.000 | 0 |
| 11250 | N | | | | NCY011250 | | INCYTE unique clone #011250 | 0 | 1 | 2.000 | 0 |
| 11263 | N | | | | NCY011263 | | INCYTE unique clone #011263 | 0 | 1 | 2.000 | 0 |
| 11264 | N | | | | NCY011264 | | INCYTE unique clone #011264 | 0 | 1 | 2.000 | 0 |
| 11268 | N | | | | NCY011268 | | INCYTE unique clone #011268 | 0 | 1 | 2.000 | 0 |
| 11270 | N | | | | NCY011270 | | INCYTE unique clone #011270 | 0 | 1 | 2.000 | 0 |
| 11275 | N | | | | NCY011275 | | INCYTE unique clone #011275 | 0 | 1 | 2.000 | 0 |
| 11293 | N | | | | NCY011293 | | INCYTE unique clone #011293 | 0 | 1 | 2.000 | 0 |
| 11318 | N | | | | NCY011318 | | INCYTE unique clone #011318 | 0 | 1 | 2.000 | 0 |
| 11322 | N | | | | NCY011322 | | INCYTE unique clone #011322 | 0 | 1 | 2.000 | 0 |
| 11324 | N | | | | NCY011324 | | INCYTE unique clone #011324 | 0 | 1 | 2.000 | 0 |
| 11325 | N | | | | NCY011325 | | INCYTE unique clone #011325 | 0 | 1 | 2.000 | 0 |
| 11332 | N | | | | NCY011332 | | INCYTE unique clone #011332 | 0 | 1 | 2.000 | 0 |
| 11333 | N | | | | NCY011333 | | INCYTE unique clone #011333 | 0 | 1 | 2.000 | 0 |
| 11338 | N | | | | NCY011338 | | INCYTE unique clone #011338 | 0 | 1 | 2.000 | 0 |
| 11339 | N | | | | NCY011339 | | INCYTE unique clone #011339 | 0 | 1 | 2.000 | 0 |
| 11340 | N | | | | NCY011340 | | INCYTE unique clone #011340 | 0 | 1 | 2.000 | 0 |
| 11348 | N | | | | NCY011348 | | INCYTE unique clone #011348 | 0 | 1 | 2.000 | 0 |
| 11378 | N | | | | NCY011378 | | INCYTE unique clone #011378 | 0 | 1 | 2.000 | 0 |
| 11391 | N | | | | NCY011391 | | INCYTE unique clone #011391 | 0 | 1 | 2.000 | 0 |
| 11392 | N | | | | NCY011392 | | INCYTE unique clone #011392 | 0 | 1 | 2.000 | 0 |
| 11398 | N | | | | NCY011398 | | INCYTE unique clone #011398 | 0 | 1 | 2.000 | 0 |
| 11408 | N | | | | NCY011408 | | INCYTE unique clone #011408 | 0 | 1 | 2.000 | 0 |
| 11413 | N | | | | NCY011413 | | INCYTE unique clone #011413 | 0 | 1 | 2.000 | 0 |
| 11425 | N | | | | NCY011425 | | INCYTE unique clone #011425 | 0 | 1 | 2.000 | 0 |
| 11435 | N | | | | NCY011435 | | INCYTE unique clone #011435 | 0 | 1 | 2.000 | 0 |
| 11441 | N | | | | NCY011441 | | INCYTE unique clone #011441 | 0 | 1 | 2.000 | 0 |
| 11442 | N | | | | NCY011442 | | INCYTE unique clone #011442 | 0 | 1 | 2.000 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
|---|---|---|---|---|---|---|---|---|---|---|---|
| 11484 | N | | | | NCY011484 | | INCYTE unique clone #011484 | 0 | 1 | 2.000 | 0 |
| 11503 | N | | | | NCY011503 | | INCYTE unique clone #011503 | 0 | 1 | 2.000 | 0 |
| 11521 | N | | | | NCY011521 | | INCYTE unique clone #011521 | 0 | 1 | 2.000 | 0 |
| 11522 | N | | | | NCY011522 | | INCYTE unique clone #011522 | 0 | 1 | 2.000 | 0 |
| 11525 | N | | | | NCY011525 | | INCYTE unique clone #011525 | 0 | 1 | 2.000 | 0 |
| 11528 | N | | | | NCY011528 | | INCYTE unique clone #011528 | 0 | 1 | 2.000 | 0 |
| 11532 | N | | | | NCY011532 | | INCYTE unique clone #011532 | 0 | 1 | 2.000 | 0 |
| 11565 | N | | | | NCY011565 | | INCYTE unique clone #011565 | 0 | 1 | 2.000 | 0 |
| 11570 | N | | | | NCY011570 | | INCYTE unique clone #011570 | 0 | 1 | 2.000 | 0 |
| 11581 | N | | | | NCY011581 | | INCYTE unique clone #011581 | 0 | 1 | 2.000 | 0 |
| 11594 | N | | | | NCY011594 | | INCYTE unique clone #011594 | 0 | 1 | 2.000 | 0 |
| 11596 | N | | | | NCY011596 | | INCYTE unique clone #011596 | 0 | 1 | 2.000 | 0 |
| 11597 | N | | | | NCY011597 | | INCYTE unique clone #011597 | 0 | 1 | 2.000 | 0 |
| 11599 | N | | | | NCY011599 | | INCYTE unique clone #011599 | 0 | 1 | 2.000 | 0 |
| 11600 | N | | | | NCY011600 | | INCYTE unique clone #011600 | 0 | 1 | 2.000 | 0 |
| 11602 | N | | | | NCY011602 | | INCYTE unique clone #011602 | 0 | 1 | 2.000 | 0 |
| 11603 | N | | | | NCY011603 | | INCYTE unique clone #011603 | 0 | 1 | 2.000 | 0 |
| 11609 | N | | | | NCY011609 | | INCYTE unique clone #011609 | 0 | 1 | 2.000 | 0 |
| 11624 | N | | | | NCY011624 | | INCYTE unique clone #011624 | 0 | 1 | 2.000 | 0 |
| 11689 | N | | | | NCY011689 | | INCYTE unique clone #011689 | 0 | 1 | 2.000 | 0 |
| 11692 | N | | | | NCY011692 | | INCYTE unique clone #011692 | 0 | 1 | 2.000 | 0 |
| 11707 | N | | | | NCY011707 | | INCYTE unique clone #011707 | 0 | 1 | 2.000 | 0 |
| 11709 | N | | | | NCY011709 | | INCYTE unique clone #011709 | 0 | 1 | 2.000 | 0 |
| 11712 | N | | | | NCY011712 | | INCYTE unique clone #011712 | 0 | 1 | 2.000 | 0 |
| 11725 | N | | | | NCY011725 | | INCYTE unique clone #011725 | 0 | 1 | 2.000 | 0 |
| 11729 | N | | | | NCY011729 | | INCYTE unique clone #011729 | 0 | 1 | 2.000 | 0 |
| 11734 | N | | | | NCY011734 | | INCYTE unique clone #011734 | 0 | 1 | 2.000 | 0 |
| 11763 | N | | | | NCY011763 | | INCYTE unique clone #011763 | 0 | 1 | 2.000 | 0 |
| 11774 | N | | | | NCY011774 | | INCYTE unique clone #011774 | 0 | 1 | 2.000 | 0 |
| 11807 | N | | | | NCY011807 | | INCYTE unique clone #011807 | 0 | 1 | 2.000 | 0 |
| 11808 | N | | | | NCY011808 | | INCYTE unique clone #011808 | 0 | 1 | 2.000 | 0 |
| 11809 | N | | | | NCY011809 | | INCYTE unique clone #011809 | 0 | 1 | 2.000 | 0 |
| 11812 | N | | | | NCY011812 | | INCYTE unique clone #011812 | 0 | 1 | 2.000 | 0 |
| 11814 | N | | | | NCY011814 | | INCYTE unique clone #011814 | 0 | 1 | 2.000 | 0 |
| 11820 | N | | | | NCY011820 | | INCYTE unique clone #011820 | 0 | 1 | 2.000 | 0 |
| 11822 | N | | | | NCY011822 | | INCYTE unique clone #011822 | 0 | 1 | 2.000 | 0 |
| 11833 | N | | | | NCY011833 | | INCYTE unique clone #011833 | 0 | 1 | 2.000 | 0 |
| 11835 | N | | | | NCY011835 | | INCYTE unique clone #011835 | 0 | 1 | 2.000 | 0 |
| 11839 | N | | | | NCY011839 | | INCYTE unique clone #011839 | 0 | 1 | 2.000 | 0 |
| 11841 | N | | | | NCY011841 | | INCYTE unique clone #011841 | 0 | 1 | 2.000 | 0 |
| 11844 | N | | | | NCY011844 | | INCYTE unique clone #011844 | 0 | 1 | 2.000 | 0 |
| 11846 | N | | | | NCY011846 | | INCYTE unique clone #011846 | 0 | 1 | 2.000 | 0 |
| 11849 | N | | | | NCY011849 | | INCYTE unique clone #011849 | 0 | 1 | 2.000 | 0 |
| 11851 | N | | | | NCY011851 | | INCYTE unique clone #011851 | 0 | 1 | 2.000 | 0 |
| 11854 | N | | | | NCY011854 | | INCYTE unique clone #011854 | 0 | 1 | 2.000 | 0 |
| 11856 | N | | | | NCY011856 | | INCYTE unique clone #011856 | 0 | 1 | 2.000 | 0 |
| 11857 | N | | | | NCY011857 | | INCYTE unique clone #011857 | 0 | 1 | 2.000 | 0 |
| 11864 | N | | | | NCY011864 | | INCYTE unique clone #011864 | 0 | 1 | 2.000 | 0 |
| 11865 | N | | | | NCY011865 | | INCYTE unique clone #011865 | 0 | 1 | 2.000 | 0 |
| 11870 | N | | | | NCY011870 | | INCYTE unique clone #011870 | 0 | 1 | 2.000 | 0 |
| 11872 | N | | | | NCY011872 | | INCYTE unique clone #011872 | 0 | 1 | 2.000 | 0 |
| 11876 | N | | | | NCY011876 | | INCYTE unique clone #011876 | 0 | 1 | 2.000 | 0 |
| 11878 | N | | | | NCY011878 | | INCYTE unique clone #011878 | 0 | 1 | 2.000 | 0 |
| 11885 | N | | | | NCY011885 | | INCYTE unique clone #011885 | 0 | 1 | 2.000 | 0 |
| 11886 | N | | | | NCY011886 | | INCYTE unique clone #011886 | 0 | 1 | 2.000 | 0 |
| 11887 | N | | | | NCY011887 | | INCYTE unique clone #011887 | 0 | 1 | 2.000 | 0 |
| 11889 | N | | | | NCY011889 | | INCYTE unique clone #011889 | 0 | 1 | 2.000 | 0 |
| 11890 | N | | | | NCY011890 | | INCYTE unique clone #011890 | 0 | 1 | 2.000 | 0 |
| 11891 | N | | | | NCY011891 | | INCYTE unique clone #011891 | 0 | 1 | 2.000 | 0 |
| 11896 | N | | | | NCY011896 | | INCYTE unique clone #011896 | 0 | 1 | 2.000 | 0 |
| 11900 | N | | | | NCY011900 | | INCYTE unique clone #011900 | 0 | 1 | 2.000 | 0 |
| 11903 | N | | | | NCY011903 | | INCYTE unique clone #011903 | 0 | 1 | 2.000 | 0 |
| 11913 | N | | | | NCY011913 | | INCYTE unique clone #011913 | 0 | 1 | 2.000 | 0 |
| 11956 | N | | | | NCY011956 | | INCYTE unique clone #011956 | 0 | 1 | 2.000 | 0 |
| 11958 | N | | | | NCY011958 | | INCYTE unique clone #011958 | 0 | 1 | 2.000 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
|---|---|---|---|---|---|---|---|---|---|---|---|
| 11978 | N | | | | NCY011978 | | INCYTE unique clone #011978 | 0 | 1 | 2.000 | 0 |
| 12019 | N | | | | NCY012019 | | INCYTE unique clone #012019 | 0 | 1 | 2.000 | 0 |
| 12032 | N | | | | NCY012032 | | INCYTE unique clone #012032 | 0 | 1 | 2.000 | 0 |
| 12033 | N | | | | NCY012033 | | INCYTE unique clone #012033 | 0 | 1 | 2.000 | 0 |
| 12063 | N | | | | NCY012063 | | INCYTE unique clone #012063 | 0 | 1 | 2.000 | 0 |
| 12065 | N | | | | NCY012065 | | INCYTE unique clone #012065 | 0 | 1 | 2.000 | 0 |
| 12067 | N | | | | NCY012067 | | INCYTE unique clone #012067 | 0 | 1 | 2.000 | 0 |
| 12073 | N | | | | NCY012073 | | INCYTE unique clone #012073 | 0 | 1 | 2.000 | 0 |
| 12076 | N | | | | NCY012076 | | INCYTE unique clone #012076 | 0 | 1 | 2.000 | 0 |
| 12080 | N | | | | NCY012080 | | INCYTE unique clone #012080 | 0 | 1 | 2.000 | 0 |
| 12084 | N | | | | NCY012084 | | INCYTE unique clone #012084 | 0 | 1 | 2.000 | 0 |
| 12186 | N | | | | NCY012186 | | INCYTE unique clone #012186 | 0 | 1 | 2.000 | 0 |
| 12212 | N | | | | NCY012212 | | INCYTE unique clone #012212 | 0 | 1 | 2.000 | 0 |
| 12231 | N | | | | NCY012231 | | INCYTE unique clone #012231 | 0 | 1 | 2.000 | 0 |
| 12247 | N | | | | NCY012247 | | INCYTE unique clone #012247 | 0 | 1 | 2.000 | 0 |
| 12249 | N | | | | NCY012249 | | INCYTE unique clone #012249 | 0 | 1 | 2.000 | 0 |
| 12291 | N | | | | NCY012291 | | INCYTE unique clone #012291 | 0 | 1 | 2.000 | 0 |
| 12335 | N | | | | NCY012335 | | INCYTE unique clone #012335 | 0 | 1 | 2.000 | 0 |
| 12336 | N | | | | NCY012336 | | INCYTE unique clone #012336 | 0 | 1 | 2.000 | 0 |
| 12353 | N | | | | NCY012353 | | INCYTE unique clone #012353 | 0 | 1 | 2.000 | 0 |
| 12356 | N | | | | NCY012356 | | INCYTE unique clone #012356 | 0 | 1 | 2.000 | 0 |
| 12364 | N | | | | NCY012364 | | INCYTE unique clone #012364 | 0 | 1 | 2.000 | 0 |
| 12386 | N | | | | NCY012386 | | INCYTE unique clone #012386 | 0 | 1 | 2.000 | 0 |
| 12410 | N | | | | NCY012410 | | INCYTE unique clone #012410 | 0 | 1 | 2.000 | 0 |
| 12411 | N | | | | NCY012411 | | INCYTE unique clone #012411 | 0 | 1 | 2.000 | 0 |
| 12423 | N | | | | NCY012423 | | INCYTE unique clone #012423 | 0 | 1 | 2.000 | 0 |
| 12426 | N | | | | NCY012426 | | INCYTE unique clone #012426 | 0 | 1 | 2.000 | 0 |
| 12437 | N | | | | NCY012437 | | INCYTE unique clone #012437 | 0 | 1 | 2.000 | 0 |
| 12440 | N | | | | NCY012440 | | INCYTE unique clone #012440 | 0 | 1 | 2.000 | 0 |
| 12477 | N | | | | NCY012477 | | INCYTE unique clone #012477 | 0 | 1 | 2.000 | 0 |
| 12496 | N | | | | NCY012496 | | INCYTE unique clone #012496 | 0 | 1 | 2.000 | 0 |
| 12498 | N | | | | NCY012498 | | INCYTE unique clone #012498 | 0 | 1 | 2.000 | 0 |
| 12502 | N | | | | NCY012502 | | INCYTE unique clone #012502 | 0 | 1 | 2.000 | 0 |
| 12503 | N | | | | NCY012503 | | INCYTE unique clone #012503 | 0 | 1 | 2.000 | 0 |
| 12517 | N | | | | NCY012517 | | INCYTE unique clone #012517 | 0 | 1 | 2.000 | 0 |
| 12519 | N | | | | NCY012519 | | INCYTE unique clone #012519 | 0 | 1 | 2.000 | 0 |
| 12530 | N | | | | NCY012530 | | INCYTE unique clone #012530 | 0 | 1 | 2.000 | 0 |
| 12541 | N | | | | NCY012541 | | INCYTE unique clone #012541 | 0 | 1 | 2.000 | 0 |
| 12547 | N | | | | NCY012547 | | INCYTE unique clone #012547 | 0 | 1 | 2.000 | 0 |
| 12566 | N | | | | NCY012566 | | INCYTE unique clone #012566 | 0 | 1 | 2.000 | 0 |
| 12568 | N | | | | NCY012568 | | INCYTE unique clone #012568 | 0 | 1 | 2.000 | 0 |
| 12569 | N | | | | NCY012569 | | INCYTE unique clone #012569 | 0 | 1 | 2.000 | 0 |
| 12583 | N | | | | NCY012583 | | INCYTE unique clone #012583 | 0 | 1 | 2.000 | 0 |
| 12621 | N | | | | NCY012621 | | INCYTE unique clone #012621 | 0 | 1 | 2.000 | 0 |
| 12636 | N | | | | NCY012636 | | INCYTE unique clone #012636 | 0 | 1 | 2.000 | 0 |
| 12638 | N | | | | NCY012638 | | INCYTE unique clone #012638 | 0 | 1 | 2.000 | 0 |
| 12643 | N | | | | NCY012643 | | INCYTE unique clone #012643 | 0 | 1 | 2.000 | 0 |
| 12662 | N | | | | NCY012662 | | INCYTE unique clone #012662 | 0 | 1 | 2.000 | 0 |
| 12669 | N | | | | NCY012669 | | INCYTE unique clone #012669 | 0 | 1 | 2.000 | 0 |
| 12679 | N | | | | NCY012679 | | INCYTE unique clone #012679 | 0 | 1 | 2.000 | 0 |
| 12702 | N | | | | NCY012702 | | INCYTE unique clone #012702 | 0 | 1 | 2.000 | 0 |
| 12705 | N | | | | NCY012705 | | INCYTE unique clone #012705 | 0 | 1 | 2.000 | 0 |
| 12748 | N | | | | NCY012748 | | INCYTE unique clone #012748 | 0 | 1 | 2.000 | 0 |
| 12757 | N | | | | NCY012757 | | INCYTE unique clone #012757 | 0 | 1 | 2.000 | 0 |
| 12786 | N | | | | NCY012786 | | INCYTE unique clone #012786 | 0 | 1 | 2.000 | 0 |
| 12808 | N | | | | NCY012808 | | INCYTE unique clone #012808 | 0 | 1 | 2.000 | 0 |
| 12810 | N | | | | NCY012810 | | INCYTE unique clone #012810 | 0 | 1 | 2.000 | 0 |
| 12828 | N | | | | NCY012828 | | INCYTE unique clone #012828 | 0 | 1 | 2.000 | 0 |
| 12830 | N | | | | NCY012830 | | INCYTE unique clone #012830 | 0 | 1 | 2.000 | 0 |
| 12843 | N | | | | NCY012843 | | INCYTE unique clone #012843 | 0 | 1 | 2.000 | 0 |
| 12844 | N | | | | NCY012844 | | INCYTE unique clone #012844 | 0 | 1 | 2.000 | 0 |
| 12845 | N | | | | NCY012845 | | INCYTE unique clone #012845 | 0 | 1 | 2.000 | 0 |
| 12851 | N | | | | NCY012851 | | INCYTE unique clone #012851 | 0 | 1 | 2.000 | 0 |
| 12852 | N | | | | NCY012852 | | INCYTE unique clone #012852 | 0 | 1 | 2.000 | 0 |
| 12854 | N | | | | NCY012854 | | INCYTE unique clone #012854 | 0 | 1 | 2.000 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
|---|---|---|---|---|---|---|---|---|---|---|---|
| 12855 | N | | | | NCY012855 | | INCYTE unique clone #012855 | 0 | 1 | 2.000 | 0 |
| 12860 | N | | | | NCY012860 | | INCYTE unique clone #012860 | 0 | 1 | 2.000 | 0 |
| 12866 | N | | | | NCY012866 | | INCYTE unique clone #012866 | 0 | 1 | 2.000 | 0 |
| 12868 | N | | | | NCY012868 | | INCYTE unique clone #012868 | 0 | 1 | 2.000 | 0 |
| 12870 | N | | | | NCY012870 | | INCYTE unique clone #012870 | 0 | 1 | 2.000 | 0 |
| 12880 | N | | | | NCY012880 | | INCYTE unique clone #012880 | 0 | 1 | 2.000 | 0 |
| 12884 | N | | | | NCY012884 | | INCYTE unique clone #012884 | 0 | 1 | 2.000 | 0 |
| 12885 | N | | | | NCY012885 | | INCYTE unique clone #012885 | 0 | 1 | 2.000 | 0 |
| 12892 | N | | | | NCY012892 | | INCYTE unique clone #012892 | 0 | 1 | 2.000 | 0 |
| 12898 | N | | | | NCY012898 | | INCYTE unique clone #012898 | 0 | 1 | 2.000 | 0 |
| 12904 | N | | | | NCY012904 | | INCYTE unique clone #012904 | 0 | 1 | 2.000 | 0 |
| 12950 | N | | | | NCY012950 | | INCYTE unique clone #012950 | 0 | 1 | 2.000 | 0 |
| 12958 | N | | | | NCY012958 | | INCYTE unique clone #012958 | 0 | 1 | 2.000 | 0 |
| 13011 | N | | | | NCY013011 | | INCYTE unique clone #013011 | 0 | 1 | 2.000 | 0 |
| 13020 | N | | | | NCY013020 | | INCYTE unique clone #013020 | 0 | 1 | 2.000 | 0 |
| 13023 | N | | | | NCY013023 | | INCYTE unique clone #013023 | 0 | 1 | 2.000 | 0 |
| 13025 | N | | | | NCY013025 | | INCYTE unique clone #013025 | 0 | 1 | 2.000 | 0 |
| 13026 | N | | | | NCY013026 | | INCYTE unique clone #013026 | 0 | 1 | 2.000 | 0 |
| 13028 | N | | | | NCY013028 | | INCYTE unique clone #013028 | 0 | 1 | 2.000 | 0 |
| 13031 | N | | | | NCY013031 | | INCYTE unique clone #013031 | 0 | 1 | 2.000 | 0 |
| 13032 | N | | | | NCY013032 | | INCYTE unique clone #013032 | 0 | 1 | 2.000 | 0 |
| 13058 | N | | | | NCY013058 | | INCYTE unique clone #013058 | 0 | 1 | 2.000 | 0 |
| 13061 | N | | | | NCY013061 | | INCYTE unique clone #013061 | 0 | 1 | 2.000 | 0 |
| 13064 | N | | | | NCY013064 | | INCYTE unique clone #013064 | 0 | 1 | 2.000 | 0 |
| 13068 | N | | | | NCY013068 | | INCYTE unique clone #013068 | 0 | 1 | 2.000 | 0 |
| 13071 | N | | | | NCY013071 | | INCYTE unique clone #013071 | 0 | 1 | 2.000 | 0 |
| 13073 | N | | | | NCY013073 | | INCYTE unique clone #013073 | 0 | 1 | 2.000 | 0 |
| 13077 | N | | | | NCY013077 | | INCYTE unique clone #013077 | 0 | 1 | 2.000 | 0 |
| 13079 | N | | | | NCY013079 | | INCYTE unique clone #013079 | 0 | 1 | 2.000 | 0 |
| 13082 | N | | | | NCY013082 | | INCYTE unique clone #013082 | 0 | 1 | 2.000 | 0 |
| 13083 | N | | | | NCY013083 | | INCYTE unique clone #013083 | 0 | 1 | 2.000 | 0 |
| 13105 | N | | | | NCY013105 | | INCYTE unique clone #013105 | 0 | 1 | 2.000 | 0 |
| 13106 | N | | | | NCY013106 | | INCYTE unique clone #013106 | 0 | 1 | 2.000 | 0 |
| 13108 | N | | | | NCY013108 | | INCYTE unique clone #013108 | 0 | 1 | 2.000 | 0 |
| 13109 | N | | | | NCY013109 | | INCYTE unique clone #013109 | 0 | 1 | 2.000 | 0 |
| 13143 | N | | | | NCY013143 | | INCYTE unique clone #013143 | 0 | 1 | 2.000 | 0 |
| 13152 | N | | | | NCY013152 | | INCYTE unique clone #013152 | 0 | 1 | 2.000 | 0 |
| 13157 | N | | | | NCY013157 | | INCYTE unique clone #013157 | 0 | 1 | 2.000 | 0 |
| 13158 | N | | | | NCY013158 | | INCYTE unique clone #013158 | 0 | 1 | 2.000 | 0 |
| 13161 | N | | | | NCY013161 | | INCYTE unique clone #013161 | 0 | 1 | 2.000 | 0 |
| 13164 | N | | | | NCY013164 | | INCYTE unique clone #013164 | 0 | 1 | 2.000 | 0 |
| 13167 | N | | | | NCY013167 | | INCYTE unique clone #013167 | 0 | 1 | 2.000 | 0 |
| 13175 | N | | | | NCY013175 | | INCYTE unique clone #013175 | 0 | 1 | 2.000 | 0 |
| 13179 | N | | | | NCY013179 | | INCYTE unique clone #013179 | 0 | 1 | 2.000 | 0 |
| 13189 | N | | | | NCY013189 | | INCYTE unique clone #013189 | 0 | 1 | 2.000 | 0 |
| 13218 | N | | | | NCY013218 | | INCYTE unique clone #013218 | 0 | 1 | 2.000 | 0 |
| 13223 | N | | | | NCY013223 | | INCYTE unique clone #013223 | 0 | 1 | 2.000 | 0 |
| 13234 | N | | | | NCY013234 | | INCYTE unique clone #013234 | 0 | 1 | 2.000 | 0 |
| 13243 | N | | | | NCY013243 | | INCYTE unique clone #013243 | 0 | 1 | 2.000 | 0 |
| 13253 | N | | | | NCY013253 | | INCYTE unique clone #013253 | 0 | 1 | 2.000 | 0 |
| 13255 | N | | | | NCY013255 | | INCYTE unique clone #013255 | 0 | 1 | 2.000 | 0 |
| 13256 | N | | | | NCY013256 | | INCYTE unique clone #013256 | 0 | 1 | 2.000 | 0 |
| 13262 | N | | | | NCY013262 | | INCYTE unique clone #013262 | 0 | 1 | 2.000 | 0 |
| 13274 | N | | | | NCY013274 | | INCYTE unique clone #013274 | 0 | 1 | 2.000 | 0 |
| 13279 | N | | | | NCY013279 | | INCYTE unique clone #013279 | 0 | 1 | 2.000 | 0 |
| 13286 | N | | | | NCY013286 | | INCYTE unique clone #013286 | 0 | 1 | 2.000 | 0 |
| 13292 | N | | | | NCY013292 | | INCYTE unique clone #013292 | 0 | 1 | 2.000 | 0 |
| 13293 | N | | | | NCY013293 | | INCYTE unique clone #013293 | 0 | 1 | 2.000 | 0 |
| 13323 | N | | | | NCY013323 | | INCYTE unique clone #013323 | 0 | 1 | 2.000 | 0 |
| 13332 | N | | | | NCY013332 | | INCYTE unique clone #013332 | 0 | 1 | 2.000 | 0 |
| 13333 | N | | | | NCY013333 | | INCYTE unique clone #013333 | 0 | 1 | 2.000 | 0 |
| 13337 | N | | | | NCY013337 | | INCYTE unique clone #013337 | 0 | 1 | 2.000 | 0 |
| 13356 | N | | | | NCY013356 | | INCYTE unique clone #013356 | 0 | 1 | 2.000 | 0 |
| 13361 | N | | | | NCY013361 | | INCYTE unique clone #013361 | 0 | 1 | 2.000 | 0 |
| 13421 | N | | | | NCY013421 | | INCYTE unique clone #013421 | 0 | 1 | 2.000 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
|---|---|---|---|---|---|---|---|---|---|---|---|
| 13433 | N | | | | NCY013433 | | INCYTE unique clone #013433 | 0 | 1 | 2.000 | 0 |
| 13443 | N | | | | NCY013443 | | INCYTE unique clone #013443 | 0 | 1 | 2.000 | 0 |
| 13454 | N | | | | NCY013454 | | INCYTE unique clone #013454 | 0 | 1 | 2.000 | 0 |
| 13478 | N | | | | NCY013478 | | INCYTE unique clone #013478 | 0 | 1 | 2.000 | 0 |
| 13485 | N | | | | NCY013485 | | INCYTE unique clone #013485 | 0 | 1 | 2.000 | 0 |
| 13490 | N | | | | NCY013490 | | INCYTE unique clone #013490 | 0 | 1 | 2.000 | 0 |
| 13494 | N | | | | NCY013494 | | INCYTE unique clone #013494 | 0 | 1 | 2.000 | 0 |
| 13508 | N | | | | NCY013508 | | INCYTE unique clone #013508 | 0 | 1 | 2.000 | 0 |
| 13522 | N | | | | NCY013522 | | INCYTE unique clone #013522 | 0 | 1 | 2.000 | 0 |
| 13535 | N | | | | NCY013535 | | INCYTE unique clone #013535 | 0 | 1 | 2.000 | 0 |
| 13543 | N | | | | NCY013543 | | INCYTE unique clone #013543 | 0 | 1 | 2.000 | 0 |
| 13553 | N | | | | NCY013553 | | INCYTE unique clone #013553 | 0 | 1 | 2.000 | 0 |
| 13563 | N | | | | NCY013563 | | INCYTE unique clone #013563 | 0 | 1 | 2.000 | 0 |
| 13565 | N | | | | NCY013565 | | INCYTE unique clone #013565 | 0 | 1 | 2.000 | 0 |
| 13585 | N | | | | NCY013585 | | INCYTE unique clone #013585 | 0 | 1 | 2.000 | 0 |
| 13666 | N | | | | NCY013666 | | INCYTE unique clone #013666 | 0 | 1 | 2.000 | 0 |
| 13691 | N | | | | NCY013691 | | INCYTE unique clone #013691 | 0 | 1 | 2.000 | 0 |
| 13714 | N | | | | NCY013714 | | INCYTE unique clone #013714 | 0 | 1 | 2.000 | 0 |
| 13716 | N | | | | NCY013716 | | INCYTE unique clone #013716 | 0 | 1 | 2.000 | 0 |
| 13719 | N | | | | NCY013719 | | INCYTE unique clone #013719 | 0 | 1 | 2.000 | 0 |
| 13726 | N | | | | NCY013726 | | INCYTE unique clone #013726 | 0 | 1 | 2.000 | 0 |
| 13727 | N | | | | NCY013727 | | INCYTE unique clone #013727 | 0 | 1 | 2.000 | 0 |
| 13728 | N | P | S | S | NCY013728 | | INCYTE unique clone #013728 | 0 | 1 | 2.000 | 0 |
| 13729 | N | U | U | U | NCY013729 | | INCYTE unique clone #013729 | 0 | 1 | 2.000 | 0 |
| 13735 | N | P | S | S | NCY013735 | | INCYTE unique clone #013735 | 0 | 1 | 2.000 | 0 |
| 13751 | N | | | | NCY013751 | | INCYTE unique clone #013751 | 0 | 1 | 2.000 | 0 |
| 13764 | N | | | | NCY013764 | | INCYTE unique clone #013764 | 0 | 1 | 2.000 | 0 |
| 13770 | N | | | | NCY013770 | | INCYTE unique clone #013770 | 0 | 1 | 2.000 | 0 |
| 13811 | N | | | | NCY013811 | | INCYTE unique clone #013811 | 0 | 1 | 2.000 | 0 |
| 13815 | N | | | | NCY013815 | | INCYTE unique clone #013815 | 0 | 1 | 2.000 | 0 |
| 13833 | N | | | | NCY013833 | | INCYTE unique clone #013833 | 0 | 1 | 2.000 | 0 |
| 13840 | N | | | | NCY013840 | | INCYTE unique clone #013840 | 0 | 1 | 2.000 | 0 |
| 13877 | N | | | | NCY013877 | | INCYTE unique clone #013877 | 0 | 1 | 2.000 | 0 |
| 13884 | N | | | | NCY013884 | | INCYTE unique clone #013884 | 0 | 1 | 2.000 | 0 |
| 13889 | N | | | | NCY013889 | | INCYTE unique clone #013889 | 0 | 1 | 2.000 | 0 |
| 13896 | N | | | | NCY013896 | | INCYTE unique clone #013896 | 0 | 1 | 2.000 | 0 |
| 13930 | N | | | | NCY013930 | | INCYTE unique clone #013930 | 0 | 1 | 2.000 | 0 |
| 13936 | N | | | | NCY013936 | | INCYTE unique clone #013936 | 0 | 1 | 2.000 | 0 |
| 13939 | N | | | | NCY013939 | | INCYTE unique clone #013939 | 0 | 1 | 2.000 | 0 |
| 13954 | N | | | | NCY013954 | | INCYTE unique clone #013954 | 0 | 1 | 2.000 | 0 |
| 13959 | N | | | | NCY013959 | | INCYTE unique clone #013959 | 0 | 1 | 2.000 | 0 |
| 13985 | N | | | | NCY013985 | | INCYTE unique clone #013985 | 0 | 1 | 2.000 | 0 |
| 13991 | N | | | | NCY013991 | | INCYTE unique clone #013991 | 0 | 1 | 2.000 | 0 |
| 13994 | N | | | | NCY013994 | | INCYTE unique clone #013994 | 0 | 1 | 2.000 | 0 |
| 14000 | N | | | | NCY014000 | | INCYTE unique clone #014000 | 0 | 1 | 2.000 | 0 |
| 14006 | N | | | | NCY014006 | | INCYTE unique clone #014006 | 0 | 1 | 2.000 | 0 |
| 14016 | N | | | | NCY014016 | | INCYTE unique clone #014016 | 0 | 1 | 2.000 | 0 |
| 14019 | N | | | | NCY014019 | | INCYTE unique clone #014019 | 0 | 1 | 2.000 | 0 |
| 14021 | N | | | | NCY014021 | | INCYTE unique clone #014021 | 0 | 1 | 2.000 | 0 |
| 14023 | N | | | | NCY014023 | | INCYTE unique clone #014023 | 0 | 1 | 2.000 | 0 |
| 14024 | N | | | | NCY014024 | | INCYTE unique clone #014024 | 0 | 1 | 2.000 | 0 |
| 14025 | N | | | | NCY014025 | | INCYTE unique clone #014025 | 0 | 1 | 2.000 | 0 |
| 14026 | N | | | | NCY014026 | | INCYTE unique clone #014026 | 0 | 1 | 2.000 | 0 |
| 14030 | N | | | | NCY014030 | | INCYTE unique clone #014030 | 0 | 1 | 2.000 | 0 |
| 14031 | N | | | | NCY014031 | | INCYTE unique clone #014031 | 0 | 1 | 2.000 | 0 |
| 14034 | N | | | | NCY014034 | | INCYTE unique clone #014034 | 0 | 1 | 2.000 | 0 |
| 14041 | N | | | | NCY014041 | | INCYTE unique clone #014041 | 0 | 1 | 2.000 | 0 |
| 14043 | N | | | | NCY014043 | | INCYTE unique clone #014043 | 0 | 1 | 2.000 | 0 |
| 14044 | N | | | | NCY014044 | | INCYTE unique clone #014044 | 0 | 1 | 2.000 | 0 |
| 14046 | N | | | | NCY014046 | | INCYTE unique clone #014046 | 0 | 1 | 2.000 | 0 |
| 14049 | N | | | | NCY014049 | | INCYTE unique clone #014049 | 0 | 1 | 2.000 | 0 |
| 14050 | N | | | | NCY014050 | | INCYTE unique clone #014050 | 0 | 1 | 2.000 | 0 |
| 14054 | N | | | | NCY014054 | | INCYTE unique clone #014054 | 0 | 1 | 2.000 | 0 |
| 14061 | N | | | | NCY014061 | | INCYTE unique clone #014061 | 0 | 1 | 2.000 | 0 |
| 14063 | N | | | | NCY014063 | | INCYTE unique clone #014063 | 0 | 1 | 2.000 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation  f = distribution  z = location  r = function  s = species  i = interest
1057 genes, for a total of 2151 clones

| number | d | f | z | r | entry | s | descriptor | bgfreq | rfend | ratio | i |
|---|---|---|---|---|---|---|---|---|---|---|---|
| 14065 | N | | | | NCY014065 | | INCYTE unique clone #014065 | 0 | 1 | 2.000 | 0 |
| 14071 | N | | | | NCY014071 | | INCYTE unique clone #014071 | 0 | 1 | 2.000 | 0 |
| 14073 | N | | | | NCY014073 | | INCYTE unique clone #014073 | 0 | 1 | 2.000 | 0 |
| 14075 | N | | | | NCY014075 | | INCYTE unique clone #014075 | 0 | 1 | 2.000 | 0 |
| 14087 | N | | | | NCY014087 | | INCYTE unique clone #014087 | 0 | 1 | 2.000 | 0 |
| 14088 | N | | | | NCY014088 | | INCYTE unique clone #014088 | 0 | 1 | 2.000 | 0 |
| 14089 | N | | | | NCY014089 | | INCYTE unique clone #014089 | 0 | 1 | 2.000 | 0 |
| 14092 | N | | | | NCY014092 | | INCYTE unique clone #014092 | 0 | 1 | 2.000 | 0 |
| 14094 | N | | | | NCY014094 | | INCYTE unique clone #014094 | 0 | 1 | 2.000 | 0 |
| 14095 | N | | | | NCY014095 | | INCYTE unique clone #014095 | 0 | 1 | 2.000 | 0 |
| 14098 | N | | | | NCY014098 | | INCYTE unique clone #014098 | 0 | 1 | 2.000 | 0 |
| 14099 | N | | | | NCY014099 | | INCYTE unique clone #014099 | 0 | 1 | 2.000 | 0 |
| 14100 | N | | | | NCY014100 | | INCYTE unique clone #014100 | 0 | 1 | 2.000 | 0 |
| 14102 | N | | | | NCY014102 | | INCYTE unique clone #014102 | 0 | 1 | 2.000 | 0 |
| 14106 | N | | | | NCY014106 | | INCYTE unique clone #014106 | 0 | 1 | 2.000 | 0 |
| 14111 | N | | | | NCY014111 | | INCYTE unique clone #014111 | 0 | 1 | 2.000 | 0 |
| 14112 | N | | | | NCY014112 | | INCYTE unique clone #014112 | 0 | 1 | 2.000 | 0 |
| 14115 | N | | | | NCY014115 | | INCYTE unique clone #014115 | 0 | 1 | 2.000 | 0 |
| 14118 | N | | | | NCY014118 | | INCYTE unique clone #014118 | 0 | 1 | 2.000 | 0 |
| 14119 | N | | | | NCY014119 | | INCYTE unique clone #014119 | 0 | 1 | 2.000 | 0 |
| 14121 | N | | | | NCY014121 | | INCYTE unique clone #014121 | 0 | 1 | 2.000 | 0 |
| 14122 | N | | | | NCY014122 | | INCYTE unique clone #014122 | 0 | 1 | 2.000 | 0 |
| 14123 | N | | | | NCY014123 | | INCYTE unique clone #014123 | 0 | 1 | 2.000 | 0 |
| 14135 | N | | | | NCY014135 | | INCYTE unique clone #014135 | 0 | 1 | 2.000 | 0 |
| 14137 | N | | | | NCY014137 | | INCYTE unique clone #014137 | 0 | 1 | 2.000 | 0 |
| 14142 | N | | | | NCY014142 | | INCYTE unique clone #014142 | 0 | 1 | 2.000 | 0 |
| 14144 | N | | | | NCY014144 | | INCYTE unique clone #014144 | 0 | 1 | 2.000 | 0 |
| 14147 | N | | | | NCY014147 | | INCYTE unique clone #014147 | 0 | 1 | 2.000 | 0 |
| 14151 | N | | | | NCY014151 | | INCYTE unique clone #014151 | 0 | 1 | 2.000 | 0 |
| 14172 | N | | | | NCY014172 | | INCYTE unique clone #014172 | 0 | 1 | 2.000 | 0 |
| 14178 | N | | | | NCY014178 | | INCYTE unique clone #014178 | 0 | 1 | 2.000 | 0 |
| 14181 | N | | | | NCY014181 | | INCYTE unique clone #014181 | 0 | 1 | 2.000 | 0 |
| 14186 | N | | | | NCY014186 | | INCYTE unique clone #014186 | 0 | 1 | 2.000 | 0 |
| 14194 | N | | | | NCY014194 | | INCYTE unique clone #014194 | 0 | 1 | 2.000 | 0 |
| 14197 | N | | | | NCY014197 | | INCYTE unique clone #014197 | 0 | 1 | 2.000 | 0 |
| 14203 | N | | | | NCY014203 | | INCYTE unique clone #014203 | 0 | 1 | 2.000 | 0 |
| 14204 | N | | | | NCY014204 | | INCYTE unique clone #014204 | 0 | 1 | 2.000 | 0 |
| 14211 | N | | | | NCY014211 | | INCYTE unique clone #014211 | 0 | 1 | 2.000 | 0 |
| 14217 | N | | | | NCY014217 | | INCYTE unique clone #014217 | 0 | 1 | 2.000 | 0 |
| 14221 | N | | | | NCY014221 | | INCYTE unique clone #014221 | 0 | 1 | 2.000 | 0 |
| 14222 | N | | | | NCY014222 | | INCYTE unique clone #014222 | 0 | 1 | 2.000 | 0 |
| 14226 | N | | | | NCY014226 | | INCYTE unique clone #014226 | 0 | 1 | 2.000 | 0 |
| 14227 | N | | | | NCY014227 | | INCYTE unique clone #014227 | 0 | 1 | 2.000 | 0 |
| 14229 | N | | | | NCY014229 | | INCYTE unique clone #014229 | 0 | 1 | 2.000 | 0 |
| 14236 | N | | | | NCY014236 | | INCYTE unique clone #014236 | 0 | 1 | 2.000 | 0 |
| 14241 | N | | | | NCY014241 | | INCYTE unique clone #014241 | 0 | 1 | 2.000 | 0 |
| 14288 | N | | | | NCY014288 | | INCYTE unique clone #014288 | 0 | 1 | 2.000 | 0 |
| 14293 | N | | | | NCY014293 | | INCYTE unique clone #014293 | 0 | 1 | 2.000 | 0 |
| 14304 | N | | | | NCY014304 | | INCYTE unique clone #014304 | 0 | 1 | 2.000 | 0 |
| 14307 | N | | | | NCY014307 | | INCYTE unique clone #014307 | 0 | 1 | 2.000 | 0 |
| 14310 | N | | | | NCY014310 | | INCYTE unique clone #014310 | 0 | 1 | 2.000 | 0 |
| 14319 | N | | | | NCY014319 | | INCYTE unique clone #014319 | 0 | 1 | 2.000 | 0 |
| 14324 | N | | | | NCY014324 | | INCYTE unique clone #014324 | 0 | 1 | 2.000 | 0 |
| 14339 | N | | | | NCY014339 | | INCYTE unique clone #014339 | 0 | 1 | 2.000 | 0 |
| 14342 | N | | | | NCY014342 | | INCYTE unique clone #014342 | 0 | 1 | 2.000 | 0 |
| 14345 | N | | | | NCY014345 | | INCYTE unique clone #014345 | 0 | 1 | 2.000 | 0 |
| 14346 | N | | | | NCY014346 | | INCYTE unique clone #014346 | 0 | 1 | 2.000 | 0 |
| 14348 | N | | | | NCY014348 | | INCYTE unique clone #014348 | 0 | 1 | 2.000 | 0 |
| 14352 | N | | | | NCY014352 | | INCYTE unique clone #014352 | 0 | 1 | 2.000 | 0 |
| 14353 | N | | | | NCY014353 | | INCYTE unique clone #014353 | 0 | 1 | 2.000 | 0 |
| 14355 | N | | | | NCY014355 | | INCYTE unique clone #014355 | 0 | 1 | 2.000 | 0 |
| 14358 | N | | | | NCY014358 | | INCYTE unique clone #014358 | 0 | 1 | 2.000 | 0 |
| 14360 | N | | | | NCY014360 | | INCYTE unique clone #014360 | 0 | 1 | 2.000 | 0 |
| 14367 | N | | | | NCY014367 | | INCYTE unique clone #014367 | 0 | 1 | 2.000 | 0 |
| 14370 | N | | | | NCY014370 | | INCYTE unique clone #014370 | 0 | 1 | 2.000 | 0 |

TABLE 5-continued

```
                      01/25/94 16:32:50
                Clone numbers 1 through 15000
                       Libraries: THP-1
                      Subtracting: HMC,
                      Designations: All
                     Sorted by ABUNDANCE
                Total clones represented: 15000
                    Total clones analyzed: 7375
                Total computation time: 31.35 minutes
d = designation f = distribution z = location r = function s = species i = interest
                   1057 genes, for a total of 2151 clones
```

| number | d | f | z | r | entry | s | descriptor | bgfreq | rfend | ratio | i |
|---|---|---|---|---|---|---|---|---|---|---|---|
| 14378 | N | | | | NCY014378 | | INCYTE unique clone #014378 | 0 | 1 | 2.000 | 0 |
| 14387 | N | | | | NCY014387 | | INCYTE unique clone #014387 | 0 | 1 | 2.000 | 0 |
| 14388 | N | | | | NCY014388 | | INCYTE unique clone #014388 | 0 | 1 | 2.000 | 0 |
| 14392 | N | | | | NCY014392 | | INCYTE unique clone #014392 | 0 | 1 | 2.000 | 0 |
| 14398 | N | | | | NCY014398 | | INCYTE unique clone #014398 | 0 | 1 | 2.000 | 0 |
| 14401 | N | | | | NCY014401 | | INCYTE unique clone #014401 | 0 | 1 | 2.000 | 0 |
| 14405 | N | | | | NCY014405 | | INCYTE unique clone #014405 | 0 | 1 | 2.000 | 0 |
| 14407 | N | | | | NCY014407 | | INCYTE unique clone #014407 | 0 | 1 | 2.000 | 0 |
| 14408 | N | | | | NCY014408 | | INCYTE unique clone #014408 | 0 | 1 | 2.000 | 0 |
| 14410 | N | | | | NCY014410 | | INCYTE unique clone #014410 | 0 | 1 | 2.000 | 0 |
| 14416 | N | | | | NCY014416 | | INCYTE unique clone #014416 | 0 | 1 | 2.000 | 0 |
| 14421 | N | | | | NCY014421 | | INCYTE unique clone #014421 | 0 | 1 | 2.000 | 0 |
| 14422 | N | | | | NCY014422 | | INCYTE unique clone #014422 | 0 | 1 | 2.000 | 0 |
| 14431 | N | | | | NCY014431 | | INCYTE unique clone #014431 | 0 | 1 | 2.000 | 0 |
| 14440 | N | | | | NCY014440 | | INCYTE unique clone #014440 | 0 | 1 | 2.000 | 0 |
| 14441 | N | | | | NCY014441 | | INCYTE unique clone #014441 | 0 | 1 | 2.000 | 0 |
| 14448 | N | | | | NCY014448 | | INCYTE unique clone #014448 | 0 | 1 | 2.000 | 0 |
| 14449 | N | | | | NCY014449 | | INCYTE unique clone #014449 | 0 | 1 | 2.000 | 0 |
| 14544 | N | | | | NCY014544 | | INCYTE unique clone #014544 | 0 | 1 | 2.000 | 0 |
| 14545 | N | | | | NCY014545 | | INCYTE unique clone #014545 | 0 | 1 | 2.000 | 0 |
| 14546 | N | | | | NCY014546 | | INCYTE unique clone #014546 | 0 | 1 | 2.000 | 0 |
| 14547 | N | | | | NCY014547 | | INCYTE unique clone #014547 | 0 | 1 | 2.000 | 0 |
| 14551 | N | | | | NCY014551 | | INCYTE unique clone #014551 | 0 | 1 | 2.000 | 0 |
| 14552 | N | | | | NCY014552 | | INCYTE unique clone #014552 | 0 | 1 | 2.000 | 0 |
| 14554 | N | | | | NCY014554 | | INCYTE unique clone #014554 | 0 | 1 | 2.000 | 0 |
| 14559 | N | | | | NCY014559 | | INCYTE unique clone #014559 | 0 | 1 | 2.000 | 0 |
| 14565 | N | | | | NCY014565 | | INCYTE unique clone #014565 | 0 | 1 | 2.000 | 0 |
| 14570 | N | | | | NCY014570 | | INCYTE unique clone #014570 | 0 | 1 | 2.000 | 0 |
| 14571 | N | | | | NCY014571 | | INCYTE unique clone #014571 | 0 | 1 | 2.000 | 0 |
| 14574 | N | | | | NCY014574 | | INCYTE unique clone #014574 | 0 | 1 | 2.000 | 0 |
| 14576 | N | | | | NCY014576 | | INCYTE unique clone #014576 | 0 | 1 | 2.000 | 0 |
| 14577 | N | | | | NCY014577 | | INCYTE unique clone #014577 | 0 | 1 | 2.000 | 0 |
| 14580 | N | | | | NCY014580 | | INCYTE unique clone #014580 | 0 | 1 | 2.000 | 0 |
| 14588 | N | | | | NCY014588 | | INCYTE unique clone #014588 | 0 | 1 | 2.000 | 0 |
| 14593 | N | | | | NCY014593 | | INCYTE unique clone #014593 | 0 | 1 | 2.000 | 0 |
| 14596 | N | | | | NCY014596 | | INCYTE unique clone #014596 | 0 | 1 | 2.000 | 0 |
| 14603 | N | | | | NCY014603 | | INCYTE unique clone #014603 | 0 | 1 | 2.000 | 0 |
| 14604 | N | | | | NCY014604 | | INCYTE unique clone #014604 | 0 | 1 | 2.000 | 0 |
| 14607 | N | | | | NCY014607 | | INCYTE unique clone #014607 | 0 | 1 | 2.000 | 0 |
| 14612 | N | | | | NCY014612 | | INCYTE unique clone #014612 | 0 | 1 | 2.000 | 0 |
| 14620 | N | | | | NCY014620 | | INCYTE unique clone #014620 | 0 | 1 | 2.000 | 0 |
| 14625 | N | | | | NCY014625 | | INCYTE unique clone #014625 | 0 | 1 | 2.000 | 0 |
| 14630 | N | | | | NCY014630 | | INCYTE unique clone #014630 | 0 | 1 | 2.000 | 0 |
| 14636 | N | | | | NCY014636 | | INCYTE unique clone #014636 | 0 | 1 | 2.000 | 0 |
| 14639 | N | | | | NCY014639 | | INCYTE unique clone #014639 | 0 | 1 | 2.000 | 0 |
| 14642 | N | | | | NCY014642 | | INCYTE unique clone #014642 | 0 | 1 | 2.000 | 0 |
| 14645 | N | | | | NCY014645 | | INCYTE unique clone #014645 | 0 | 1 | 2.000 | 0 |
| 14654 | N | | | | NCY014654 | | INCYTE unique clone #014654 | 0 | 1 | 2.000 | 0 |
| 14657 | N | | | | NCY014657 | | INCYTE unique clone #014657 | 0 | 1 | 2.000 | 0 |
| 14661 | N | | | | NCY014661 | | INCYTE unique clone #014661 | 0 | 1 | 2.000 | 0 |
| 14667 | N | | | | NCY014667 | | INCYTE unique clone #014667 | 0 | 1 | 2.000 | 0 |
| 14669 | N | | | | NCY014669 | | INCYTE unique clone #014669 | 0 | 1 | 2.000 | 0 |
| 14671 | N | | | | NCY014671 | | INCYTE unique clone #014671 | 0 | 1 | 2.000 | 0 |
| 14673 | N | | | | NCY014673 | | INCYTE unique clone #014673 | 0 | 1 | 2.000 | 0 |
| 14674 | N | | | | NCY014674 | | INCYTE unique clone #014674 | 0 | 1 | 2.000 | 0 |
| 14677 | N | | | | NCY014677 | | INCYTE unique clone #014677 | 0 | 1 | 2.000 | 0 |
| 14683 | N | | | | NCY014683 | | INCYTE unique clone #014683 | 0 | 1 | 2.000 | 0 |
| 14698 | N | | | | NCY014698 | | INCYTE unique clone #014698 | 0 | 1 | 2.000 | 0 |
| 14703 | N | | | | NCY014703 | | INCYTE unique clone #014703 | 0 | 1 | 2.000 | 0 |
| 14710 | N | | | | NCY014710 | | INCYTE unique clone #014710 | 0 | 1 | 2.000 | 0 |
| 14744 | N | | | | NCY014744 | | INCYTE unique clone #014744 | 0 | 1 | 2.000 | 0 |
| 14746 | N | | | | NCY014746 | | INCYTE unique clone #014746 | 0 | 1 | 2.000 | 0 |
| 14756 | N | | | | NCY014756 | | INCYTE unique clone #014756 | 0 | 1 | 2.000 | 0 |
| 14758 | N | | | | NCY014758 | | INCYTE unique clone #014758 | 0 | 1 | 2.000 | 0 |
| 14760 | N | | | | NCY014760 | | INCYTE unique clone #014760 | 0 | 1 | 2.000 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
|---|---|---|---|---|---|---|---|---|---|---|---|
| 14761 | N | | | | NCY014761 | | INCYTE unique clone #014761 | 0 | 1 | 2.000 | 0 |
| 14764 | N | | | | NCY014764 | | INCYTE unique clone #014764 | 0 | 1 | 2.000 | 0 |
| 14766 | N | | | | NCY014766 | | INCYTE unique clone #014766 | 0 | 1 | 2.000 | 0 |
| 14771 | N | | | | NCY014771 | | INCYTE unique clone #014771 | 0 | 1 | 2.000 | 0 |
| 14775 | N | | | | NCY014775 | | INCYTE unique clone #014775 | 0 | 1 | 2.000 | 0 |
| 14780 | N | | | | NCY014780 | | INCYTE unique clone #014780 | 0 | 1 | 2.000 | 0 |
| 14782 | N | | | | NCY014782 | | INCYTE unique clone #014782 | 0 | 1 | 2.000 | 0 |
| 14785 | N | | | | NCY014785 | | INCYTE unique clone #014785 | 0 | 1 | 2.000 | 0 |
| 14786 | N | | | | NCY014786 | | INCYTE unique clone #014786 | 0 | 1 | 2.000 | 0 |
| 14794 | N | | | | NCY014794 | | INCYTE unique clone #014794 | 0 | 1 | 2.000 | 0 |
| 14798 | N | | | | NCY014798 | | INCYTE unique clone #014798 | 0 | 1 | 2.000 | 0 |
| 14799 | N | | | | NCY014799 | | INCYTE unique clone #014799 | 0 | 1 | 2.000 | 0 |
| 14830 | N | | | | NCY014830 | | INCYTE unique clone #014830 | 0 | 1 | 2.000 | 0 |
| 14831 | N | | | | NCY014831 | | INCYTE unique clone #014831 | 0 | 1 | 2.000 | 0 |
| 14835 | N | | | | NCY014835 | | INCYTE unique clone #014835 | 0 | 1 | 2.000 | 0 |
| 14839 | N | | | | NCY014839 | | INCYTE unique clone #014839 | 0 | 1 | 2.000 | 0 |
| 14840 | N | | | | NCY014840 | | INCYTE unique clone #014840 | 0 | 1 | 2.000 | 0 |
| 14843 | N | | | | NCY014843 | | INCYTE unique clone #014843 | 0 | 1 | 2.000 | 0 |
| 14845 | N | | | | NCY014845 | | INCYTE unique clone #014845 | 0 | 1 | 2.000 | 0 |
| 14847 | N | | | | NCY014847 | | INCYTE unique clone #014847 | 0 | 1 | 2.000 | 0 |
| 14852 | N | | | | NCY014852 | | INCYTE unique clone #014852 | 0 | 1 | 2.000 | 0 |
| 14855 | N | | | | NCY014855 | | INCYTE unique clone #014855 | 0 | 1 | 2.000 | 0 |
| 14887 | N | | | | NCY014887 | | INCYTE unique clone #014887 | 0 | 1 | 2.000 | 0 |
| 14892 | N | | | | NCY014892 | | INCYTE unique clone #014892 | 0 | 1 | 2.000 | 0 |
| 14896 | N | | | | NCY014896 | | INCYTE unique clone #014896 | 0 | 1 | 2.000 | 0 |
| 14898 | N | | | | NCY014898 | | INCYTE unique clone #014898 | 0 | 1 | 2.000 | 0 |
| 14903 | N | | | | NCY014903 | | INCYTE unique clone #014903 | 0 | 1 | 2.000 | 0 |
| 14909 | N | | | | NCY014909 | | INCYTE unique clone #014909 | 0 | 1 | 2.000 | 0 |
| 14910 | N | | | | NCY014910 | | INCYTE unique clone #014910 | 0 | 1 | 2.000 | 0 |
| 14912 | N | | | | NCY014912 | | INCYTE unique clone #014912 | 0 | 1 | 2.000 | 0 |
| 14914 | N | | | | NCY014914 | | INCYTE unique clone #014914 | 0 | 1 | 2.000 | 0 |
| 14915 | N | | | | NCY014915 | | INCYTE unique clone #014915 | 0 | 1 | 2.000 | 0 |
| 14917 | N | | | | NCY014917 | | INCYTE unique clone #014917 | 0 | 1 | 2.000 | 0 |
| 14918 | N | | | | NCY014918 | | INCYTE unique clone #014918 | 0 | 1 | 2.000 | 0 |
| 14922 | N | | | | NCY014922 | | INCYTE unique clone #014922 | 0 | 1 | 2.000 | 0 |
| 14930 | N | | | | NCY014930 | | INCYTE unique clone #014930 | 0 | 1 | 2.000 | 0 |
| 14931 | N | | | | NCY014931 | | INCYTE unique clone #014931 | 0 | 1 | 2.000 | 0 |
| 14932 | N | | | | NCY014932 | | INCYTE unique clone #014932 | 0 | 1 | 2.000 | 0 |
| 14935 | N | | | | NCY014935 | | INCYTE unique clone #014935 | 0 | 1 | 2.000 | 0 |
| 14939 | N | | | | NCY014939 | | INCYTE unique clone #014939 | 0 | 1 | 2.000 | 0 |
| 14943 | N | | | | NCY014943 | | INCYTE unique clone #014943 | 0 | 1 | 2.000 | 0 |
| 14944 | N | | | | NCY014944 | | INCYTE unique clone #014944 | 0 | 1 | 2.000 | 0 |
| 14961 | N | | | | NCY014961 | | INCYTE unique clone #014961 | 0 | 1 | 2.000 | 0 |
| 14974 | N | | | | NCY014974 | | INCYTE unique clone #014974 | 0 | 1 | 2.000 | 0 |
| 14976 | N | | | | NCY014976 | | INCYTE unique clone #014976 | 0 | 1 | 2.000 | 0 |
| 14979 | N | | | | NCY014979 | | INCYTE unique clone #014979 | 0 | 1 | 2.000 | 0 |
| 14981 | N | | | | NCY014981 | | INCYTE unique clone #014981 | 0 | 1 | 2.000 | 0 |
| 14990 | N | | | | NCY014990 | | INCYTE unique clone #014990 | 0 | 1 | 2.000 | 0 |
| 14991 | N | | | | NCY014991 | | INCYTE unique clone #014991 | 0 | 1 | 2.000 | 0 |
| 14926 | E | C | C | N | HUMIMPH | | Inosine mono-PO4 dehydrogenase, type I | 0 | 1 | 2.000 | 0 |
| 10061 | O | P | C | E | DOGSMIT | D | Inositol cotransporter, Na/myo- | 0 | 1 | 2.000 | 0 |
| 11895 | E | P | U | B | HUMGFIBPA | | Insulin-like growth factor-binding ptn | 0 | 1 | 2.000 | 0 |
| 13354 | E | P | E | B | HSICAM1 | | Intercellular adhesion molecule ICAM-1 | 0 | 1 | 2.000 | 0 |
| 10097 | E | P | U | H | HUMIFNINI | | Interferon gamma inducible early resp | 0 | 1 | 2.000 | 0 |
| 11012 | E | P | S | S | HUMIL10 | | Interleukin-10 (includes intron) | 0 | 1 | 2.000 | 0 |
| 12403 | E | P | S | S | HUMIL6CSF | | Interleukin-6 | 0 | 1 | 2.000 | 0 |
| 10521 | E | U | E | B | HSKDEL | | KDEL receptor, ERD 2 | 0 | 1 | 2.000 | 0 |
| 12805 | E | P | C | K | HUMP13KIN | | Kinase P13; tyrosine kinase receptor | 0 | 1 | 2.000 | 0 |
| 10553 | O | U | C | Y | RATERK3 | R | Kinase, extracellular signal-related | 0 | 1 | 2.000 | 1 |
| 14670 | E | U | N | D | HUMHPF4 | | Kruppel related DNA binding protein 4 | 0 | 1 | 2.000 | 0 |
| 13873 | E | P | E | B | HUMCD53 | | Leukocyte surface antigen CD53 | 0 | 1 | 2.000 | 0 |
| 14108 | E | P | S | W | HUMLIPCHL | | Lipase, lysosomal, acid; cholesterase | 0 | 1 | 2.000 | 0 |
| 11733 | E | P | C | I | HUMALBP | | Lipid binding protein, adipocyte | 0 | 1 | 2.000 | 0 |
| 14083 | E | C | S | W | HUMLPL | | Lipoprotein lipase | 0 | 1 | 2.000 | 0 |
| 12109 | E | C | C | E | HUMGLYI | | Lyase, lactoyl glutathione | 0 | 1 | 2.000 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
|---|---|---|---|---|---|---|---|---|---|---|---|
| 11042 | E | P | E | B | HUMLAMP1B | | Lysosomal membrane gp-2; LAMP-2 | 0 | 1 | 2.000 | 0 |
| 11827 | E | P | E | B | HSHLDR1B | | MHC class II antigen; glycoprotein | 0 | 1 | 2.000 | 0 |
| 11246 | E | P | E | B | HUMA2MGRAP | | Macroglobulin, (alpha-2)-associated pt | 0 | 1 | 2.000 | 0 |
| 12869 | E | P | E | B | HUMA2M | | Macroglobulin, alpha-2- | 0 | 1 | 2.000 | 0 |
| 10511 | E | C | C | T | S57575 | | Macropain, HMW proteosome SU zeta | 0 | 1 | 2.000 | 0 |
| 13339 | E | C | N | K | HUMMNMP | | Major nuclear matrix protein | 0 | 1 | 2.000 | 0 |
| 14665 | E | P | S | A | HSMGSA | | Melanoma growth stim factor (MIP-2a) | 0 | 1 | 2.000 | 0 |
| 12707 | E | C | C | E | HSNMTDC | | Methylene THF dehydrogenase, NAD-dep | 0 | 1 | 2.000 | 0 |
| 12963 | O | U | E | W | CRUMEVTRSP | S | Mevalonate transporter | 0 | 1 | 2.000 | 3 |
| 14321 | E | C | E | B | HUMMCR | | Mineralocorticoid receptor | 0 | 1 | 2.000 | 0 |
| 12838 | E | P | C | Y | HUMMKK | | Mitogen activated ptn kinasekinase MAP | 0 | 1 | 2.000 | 0 |
| 13705 | O | C | M | Z | BTUBRE49 | V | NADH:ubiquinone oxidoreductase | 0 | 1 | 2.000 | 0 |
| 11030 | O | P | U | H | RATIRPRA | R | NGF:induced IFN-related ptn | 0 | 1 | 2.000 | 4 |
| 14036 | O | P | S | H | RATNIPS | R | NGF:inducible secreted protein | 0 | 1 | 2.000 | 1 |
| 11304 | O | P | U | U | M28274 | R | Neuronal protein NP25 | 0 | 1 | 2.000 | 1 |
| 14224 | E | C | N | U | HUMNUMB23 | | Nuclear protein B23 | 0 | 1 | 2.000 | 0 |
| 13904 | E | C | N | U | HUMNAP | | Nucleosome assembly protein | 0 | 1 | 2.000 | 0 |
| 14568 | E | C | U | U | HUMTB31A | | Omnipotent suppressor 45, yeast; TB3-1 | 0 | 1 | 2.000 | 0 |
| 13542 | E | U | U | Y | HSCFMS | | Oncogene fms | 0 | 1 | 2.000 | 0 |
| 10796 | E | P | U | D | HSRLF | | Oncogene myc; rlf gene | 0 | 1 | 2.000 | 0 |
| 10032 | E | P | U | O | HUMRAB5B | | Oncogene rab5b, ras-related ptn | 0 | 1 | 2.000 | 0 |
| 12672 | E | C | U | O | HSRAPB1 | | Oncogene rap 1B; ras-related | 0 | 1 | 2.000 | 0 |
| 14707 | E | U | U | G | HSRAP1A | | Oncogene rab1a, ras-related protein | 0 | 1 | 2.000 | 0 |
| 14368 | E | U | U | D | HUMCRELA | | Oncogene rel | 0 | 1 | 2.000 | 0 |
| 13353 | O | C | N | D | MMCRELM | | Oncogene rel | 0 | 1 | 2.000 | 1 |
| 13829 | E | C | C | W | HUM2OGDH | | Oxoglutarate dehydrogenase, 2- | 0 | 1 | 2.000 | 0 |
| 14309 | H | P | N | D | HSRDC1MR | | POU homeodomain ptn, nerve-specific | 0 | 1 | 2.000 | 1 |
| 11512 | E | P | C | M | HUMPAM12 | | Peptidylglycine a-amidating monooxy. | 0 | 1 | 2.000 | 0 |
| 14549 | O | C | N | D | BTPAPOLY | V | Poly (A) polymerase | 0 | 1 | 2.000 | 0 |
| 12812 | O | C | C | T | M27072 | F | Poly-A binding protein | 0 | 1 | 2.000 | 1 |
| 13069 | E | P | C | T | HUMTIA1E | | Poly-A binding protein homolog TIA-1 | 0 | 1 | 2.000 | 1 |
| 11314 | E | P | C | T | HSPROS27 | | Prosomal RNA-binding ptn PROS-27 | 0 | 1 | 2.000 | 0 |
| 14640 | E | U | U | Y | HUMG19P1A | | Protein 80-H, kinase c substrate | 0 | 1 | 2.000 | 0 |
| 11254 | E | P | U | U | HUMB12A | | Protein B12; TNF-ind endothelial 1 res | 0 | 1 | 2.000 | 0 |
| 11445 | E | C | C | Y | HUMCAMPPK | | Protein kinase, cAMP-dependent, type 1a | 0 | 1 | 2.000 | 0 |
| 10845 | O | U | U | U | MUSBRAF | M | Protein of unknown function | 0 | 1 | 2.000 | 0 |
| 13875 | O | C | C | Y | OCPP1 | B | Protein phosphatase 1 | 0 | 1 | 2.000 | 1 |
| 12494 | H | P | E | B | HSPMIPR | | Putative receptor protein PMI | 0 | 1 | 2.000 | 3 |
| 13317 | E | C | C | N | HUMDUPTPP | | Pyrophosphatase DUTP | 0 | 1 | 2.000 | 0 |
| 10947 | E | C | N | T | HSRING10 | | RING10; proteasome-related MHC gene | 0 | 1 | 2.000 | 0 |
| 11728 | E | C | N | E | HUMPOLACCB | | Replicative polymerase accessory ptn | 0 | 1 | 2.000 | 0 |
| 13319 | E | P | N | O | HUMRETBLAS | | Retinoblastoma susceptibility gene | 0 | 1 | 2.000 | 0 |
| 10271 | E | P | U | O | HUMRBS | | Retinoblastoma-associated ptn | 0 | 1 | 2.000 | 0 |
| 12764 | E | P | U | V | HSINER11 | | Retroposon SINE-R11 (endog retrovirus) | 0 | 1 | 2.000 | 0 |
| 13226 | E | P | U | V | HUMJNLTRB | | Retroviral long terminal repeat | 0 | 1 | 2.000 | 0 |
| 10606 | E | C | C | G | HUMRHOGDI | | Rho GTP dissociation inhibitor | 0 | 1 | 2.000 | 1 |
| 14886 | E | C | C | N | HSRIREM1 | | Ribonucleotide reductase M1 subunit | 0 | 1 | 2.000 | 0 |
| 14564 | E | C | C | R | HSRRN18S | | Ribosomal RNA, 18S | 0 | 1 | 2.000 | 0 |
| 14938 | E | C | C | R | HSRPS18 | | Ribosomal protein S18 | 0 | 1 | 2.000 | 0 |
| 12955 | O | P | U | U | CHKGISM22A | C | SM22-alpha; gizzard smooth muscle | 0 | 1 | 2.000 | 1 |
| 11909 | O | C | C | T | DOGSRP9A | D | Signal recognition particle SRP9 | 0 | 1 | 2.000 | 0 |
| 14763 | O | C | C | T | CFSRP68 | D | Signal recognition particle, 68kDa su | 0 | 1 | 2.000 | 0 |
| 10152 | E | P | E | B | HUMZP3 | | Sperm receptor | 0 | 1 | 2.000 | 0 |
| 13888 | H | P | E | B | HUMARC1 | | Steroid receptor, novel/transcr factor | 0 | 1 | 2.000 | 3 |
| 10256 | E | P | S | P | HUMPACE4A | | Subtilisin-like ptn PACE4 | 0 | 1 | 2.000 | 3 |
| 13680 | E | P | S | E | HSMNSODR | | Superoxide dismutase, Mn | 0 | 1 | 2.000 | 0 |
| 11706 | O | C | E | U | MUSSURF4A | M | Surfeit locus 4 protein | 0 | 1 | 2.000 | 1 |
| 12520 | O | P | U | U | MMTIS7M | M | TPA-induced sequence-7 | 0 | 1 | 2.000 | 1 |
| 11374 | E | C | C | T | HSGTS | | TRNA synthetase, glutaminyl- | 0 | 1 | 2.000 | 0 |
| 10777 | O | C | C | M | CRUSTSTA | I | TRNA synthetase, seryl- | 0 | 1 | 2.000 | 0 |
| 12675 | E | C | N | D | HSBTF3A | | Transcription factor | 0 | 1 | 2.000 | 0 |
| 10432 | E | P | E | B | HUMTFRRA | | Transferrin receptor | 0 | 1 | 2.000 | 0 |
| 11154 | E | P | S | S | HSTGFB1 | | Transforming growth factor-B1 | 0 | 1 | 2.000 | 0 |
| 10026 | E | C | C | T | HUMELF2 | | Translation initiation factor 2B | 0 | 1 | 2.000 | 0 |
| 12696 | E | P | C | Y | HSCL100 | | Tyrosine phosphatase CL 100 | 0 | 1 | 2.000 | 0 |

TABLE 5-continued

01/25/94 16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation f = distribution z = location r = function s = species i = interest
1057 genes, for a total of 2151 clones

| number | d | f | z | r | entry | s | descriptor | bgfreq | rfend | ratio | i |
|---|---|---|---|---|---|---|---|---|---|---|---|
| 13423 | E | C | C | L | HSQAE1 | | Ubiquitin activating enzyme E1 | 0 | 1 | 2.000 | 0 |
| 10858 | E | U | U | U | HUMDHAD | | Unknown transcript from cosmid DHAD | 0 | 1 | 2.000 | 0 |
| 14425 | E | C | C | N | HSNGMRNA | | Uracil DNA glycosylase | 0 | 1 | 2.000 | 0 |
| 14213 | O | U | U | U | XELXLAN | F | Xlan4 | 0 | 1 | 2.000 | 0 |
| 13456 | E | P | N | D | SSMBPROT2 | | Zn finger protein, binds MHC enhancer | 0 | 1 | 2.000 | 0 |
| 10009 | E | C | K | K | HSAC07 | | Actin, beta- | 18 | 29 | 1.611 | 0 |
| 11341 | E | P | C | I | HUMFKBP | | FK506 binding protein | 2 | 3 | 1.500 | 0 |
| 11255 | O | U | C | E | MAP5PROMR | S | Isomerase/Pi-PLc, protein disulphide- | 2 | 3 | 1.500 | 3 |
| 10019 | E | C | N | K | HUMNPM | | Nucleophosmin | 2 | 3 | 1.500 | 0 |
| 10458 | E | C | C | R | HUMRPL7A | | Ribosomal protein L7A; PLA-X; surf3 | 2 | 3 | 1.500 | 0 |
| 10901 | O | C | C | R | RNRPS5 | R | Ribosomal protein S5; EST 000HE10 | 2 | 3 | 1.500 | 0 |
| 12431 | E | P | U | U | HUMSET | | SET gene (unknown function) | 2 | 3 | 1.500 | 0 |
| 11357 | E | P | E | A | HSTRA1 | | Tumor rejection Ag; tra1 (mouse homol) | 2 | 3 | 1.500 | 0 |
| 11021 | E | C | C | Q | HSGAPDR | | Glyceraldehyde-3-phosphate dehydrogen | 3 | 4 | 1.333 | 0 |
| 10172 | E | C | C | T | HSEF1AC | | Elongation factor 1-alpha | 32 | 38 | 1.188 | 0 |
| 10024 | E | C | K | K | HSACTCGR | | Actin, cytoskeletal gamma | 7 | 7 | 1.000 | 0 |
| 10842 | O | C | M | Q | PIGMDH | P | Malate dehydrogenase | 2 | 2 | 1.000 | 0 |
| 10250 | E | P | U | U | HUMMOESIN | | Moesin (Talin/ezrin family) | 2 | 2 | 1.000 | 0 |
| 10161 | E | C | K | K | HSMRLCM | | Myosin regulatory L chain | 2 | 2 | 1.000 | 0 |
| 12798 | E | C | C | E | HUMARF2A | | ADP-ribosylation factor 2 (ARF2) | 1 | 1 | 1.000 | 0 |
| 14022 | E | C | C | N | HUMAMPD3 | | AMP deaminase AMPD3 | 1 | 1 | 1.000 | 0 |
| 14409 | O | C | K | K | CHKCAPZ | C | Actin-capping protein, alpha2 | 1 | 1 | 1.000 | 1 |
| 11705 | E | C | C | T | HSEF1G | | Elongation factor 1-gamma | 1 | 1 | 1.000 | 0 |
| 12639 | E | C | N | K | HSFIB | | Fibrillarin | 1 | 1 | 1.000 | 0 |
| 10296 | E | C | C | Q | HUMALDA | | Fructose 1,6-diPO4 aldolase A | 1 | 1 | 1.000 | 0 |
| 11855 | O | C | C | Z | BOVHATPA | V | H+ ATPase, vacuolar | 1 | 1 | 1.000 | 0 |
| 13155 | E | C | U | H | HSHSP90R | | Heat shock protein PBLy, 90 kDa | 1 | 1 | 1.000 | 1 |
| 11727 | O | C | N | D | MMH33REP | M | Histone H3.3, Replacement variant | 1 | 1 | 1.000 | 0 |
| 10014 | O | C | C | T | MMEIF4AR | M | Initiation factor eIF-4AII | 1 | 1 | 1.000 | 0 |
| 12901 | E | C | C | Q | HSLDHAR | | Lactate dehydrogenase | 1 | 1 | 1.000 | 0 |
| 11626 | E | P | C | U | HUMCD63 | | Lysosomal membrane glycoptn CD63 | 1 | 1 | 1.000 | 0 |
| 10917 | E | U | C | G | HUMRASAC | | Oncogene ras-like protein | 1 | 1 | 1.000 | 2 |
| 11852 | E | P | S | W | HUMPHPLA2 | | Phospholipase A2,14-3-3, 30 kDa, intra | 1 | 1 | 1.000 | 0 |
| 11861 | E | C | C | Q | HSPFKLA | | Phosphophosfructokinase | 1 | 1 | 1.000 | 0 |
| 14382 | E | C | C | M | HUMPYHBASA | | Prolyl-4-hydroxylase, alpha subunit | 1 | 1 | 1.000 | 0 |
| 13890 | E | C | U | D | HSRD | | RNA-binding protein RD, MHC class III | 1 | 1 | 1.000 | 0 |
| 11481 | E | C | C | R | HUMRIBPROD | | Ribosomal protein L18a | 1 | 1 | 1.000 | 0 |
| 13013 | E | P | C | E | HUMTHBP | | Thyroid hormone bp;prolyl-4-hyd'lase | 1 | 1 | 1.000 | 0 |
| 10552 | E | C | K | K | HSTROPCR | | Tropomyosin TM30, cytoskeletal | 1 | 1 | 1.000 | 0 |
| 14444 | E | U | U | U | RNUNR | R | Unr protein; linked to N-ras | 1 | 1 | 1.000 | 1 |
| 12848 | O | U | U | U | RNUNR | R | Unr protein; linked to N-ras | 1 | 1 | 1.000 | 1 |
| 10762 | E | C | U | H | HSHSC70 | | Heat shock protein hsc70 | 9 | 6 | 0.667 | 0 |
| 11845 | E | C | N | T | HUMHNRNA | | HnRNP particle C | 6 | 4 | 0.667 | 0 |
| 10081 | O | C | C | R | RRRPL8 | R | Ribosomal protein L8 | 3 | 2 | 0.667 | 0 |
| 10159 | E | C | C | R | HUMRPS7A | | Ribosomal protein S7a | 3 | 2 | 0.667 | 0 |
| 10228 | E | P | C | F | HUMFERH | | Ferritin, heavy chain | 10 | 6 | 0.600 | 0 |
| 12673 | E | C | M | H | HUMPMMPP1 | | Chaperonin/mt matrix ptn P1/HSP60 | 5 | 3 | 0.660 | 0 |
| 10449 | O | C | C | M | RATODCAC | R | Ornithine decarboxylase antizyme | 7 | 4 | 0.571 | 3 |
| 11323 | E | C | M | Z | HUMTLCA | | ADP/ATP translocase, clone pHAT8 | 2 | 1 | 0.500 | 0 |
| 11881 | O | P | C | C | MUSCAP102 | M | Cadherin-associated protein (CAP 102) | 2 | 1 | 0.500 | 2 |
| 14201 | E | C | U | H | HUMHSP90 | | Heat shock protein, 90-kDa | 2 | 1 | 0.500 | 0 |
| 10404 | E | P | E | B | HUMHLAB | | Human leukocyte antigen-ABC, class I | 2 | 1 | 0.500 | 0 |
| 10517 | E | U | U | U | HSLLREP3 | | LLrep3; repetitive DNA | 2 | 1 | 0.500 | 0 |
| 12322 | E | C | N | D | HSPTBMR | | Polypyrimidine tract-binding ptn | 2 | 1 | 0.500 | 0 |
| 13693 | E | C | N | D | HSTF2B | | Transcription initiation factor 2B | 2 | 1 | 0.500 | 0 |
| 10091 | E | C | C | R | HUMPPARP0 | | Ribosomal phosphoprotein P0, acidic | 16 | 6 | 0.375 | 0 |
| 10266 | E | C | N | D | HSH2AZ | | Histone H2A.Z | 3 | 1 | 0.333 | 0 |
| 10100 | E | C | C | R | HSRPL19 | | Ribosomal protein L19 | 3 | 1 | 0.333 | 0 |
| 10099 | E | C | C | R | HUMRPS14 | | Ribosomal protein S14 | 3 | 1 | 0.333 | 0 |
| 10564 | O | C | K | K | MMTALINR | M | Talin | 3 | 1 | 0.333 | 0 |

What is claimed is:

1. A method of analyzing a specimen containing gene transcripts, comprising the steps of:

obtaining a first mixture of mRNA;

making cDNA copies of the mRNA;

isolating a representative population of the cDNA copies and producing therefrom a first cDNA library, wherein a selected set of random primers is used in the generation of the first cDNA library;

identifying a first set of gene transcripts from the first library and determining cDNA sequences corresponding to the gene transcripts;

processing the cDNA sequences corresponding to the first gene transcripts in a programmed computer in which a database of reference transcript sequences indicative of reference cDNA sequences is stored, to generate a first identified sequence value for each of the first gene transcripts, where each said identified sequence value is indicative of a sequence annotation and a degree of match between one of the first gene transcripts and at least one of the reference cDNA sequences; and processing each said identified sequence value to generate first final data values indicative of a number of times each first identified sequence value is present in the first cDNA library.

2. The method of claim 1, wherein the first mixture of mRNA is obtained from a human cell.

3. The method of claim 1, wherein the mixture of mRNA is obtained from a combination of two or more samples.

4. The method of claim 1, wherein the mRNA obtained is partial mRNA sequences.

5. The method of claim 1, further comprising:

obtaining a second mixture of mRNA from a human cell;

making cDNA copies of the second mixture of mRNA;

isolating a representative population of cDNA copies and producing therefrom a second cDNA library, wherein a selected set of random primers is used in the generation of the second cDNA library;

identifying a second set of gene transcripts from the second library and determining cDNA sequences corresponding to the gene transcripts;

processing the cDNA sequences corresponding to the second gene transcripts in a programmed computer in which a database of reference transcript sequences indicative of reference biological sequences is stored, to generate a second identified sequence value for each of the second gene transcripts, where each said second identified sequence value is indicative of a sequence annotation and a degree of match between one of the second gene transcripts and at least one of the reference gene transcripts; and processing each said second identified sequence value to generate second final data values indicative of a number of times each second identified sequence value is present in the second cDNA library.

6. The method of claim 5, wherein the second library comprises at least 5,000 cDNAs.

7. The method of claim 5, further comprising:

processing the first final data values and the second final data values to generate ratio values of gene -transcripts, each of said ratio values indicative of differences in numbers of gene transcripts between the first mixture of mRNA and the second mixture of mRNA.

8. The method of claim 7, further comprising:

subtracting the first final data values from the second final data values to identify one or more genes that are differentially expressed.

9. The method of claim 7, wherein the first mixture of mRNA is obtained from a sample extracted from a healthy human patient and the second mixture of mRNA is obtained from a sample extracted from an unhealthy human patient.

10. The method of claim 1, wherein the first library comprises at least 5,000 cDNAs.

11. A method of producing a gene transcript image, comprising the steps of obtaining a mixture of mRNA from a biological specimen;

making cDNA copies of the mRNA, wherein the cDNA copies of mRNA are made using a selected set of random primers;

inserting the cDNA copies into a suitable vector and transfecting suitable host strain cells with the vector and growing clones, each clone representing a unique mRNA;

isolating a representative population of at least 5,000 recombinant clones;

identifying amplified cDNAs from each clone in the population by a sequence-specific method which identifies a gene from which the unique mRNA was transcribed;

determining a number of times each gene is represented within the population of clones as an indication of relative abundance; and listing genes and their relative abundance in order of abundance, thereby producing a gene transcript image comparing the gene transcript image with a gene transcript image derived from a diseased biological specimen and/or a normal biological specimen.

* * * * *